(12) United States Patent
Mc Avoy et al.

(10) Patent No.: US 7,741,548 B2
(45) Date of Patent: Jun. 22, 2010

(54) METHOD AND COMPOSITION FOR INCREASING BRANCHING AND FLOWERING RESPONSE IN PLANTS

(75) Inventors: Richard Mc Avoy, Mansfield Center, CT (US); Mariya Khodakovskaya, Raleigh, NC (US); Yi Li, Mansfield, CT (US)

(73) Assignee: University of Connecticut, Farmington, CT (US)

( * ) Notice: Subject to any disclaimer, the term of this patent is extended or adjusted under 35 U.S.C. 154(b) by 552 days.

(21) Appl. No.: 11/432,314

(22) Filed: May 10, 2006

(65) Prior Publication Data

US 2007/0083948 A1    Apr. 12, 2007

Related U.S. Application Data

(60) Provisional application No. 60/680,403, filed on May 12, 2005.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................. 800/323.2; 800/298; 800/317.3; 800/278; 800/290; 435/419; 435/320.1; 536/23.6; 536/24.1

(58) Field of Classification Search ........................ None
See application file for complete search history.

(56) References Cited

U.S. PATENT DOCUMENTS 5,177,307 A * 1/1993 Houck et al. ................. 800/278
6,204,437 B1 * 3/2001 Grierson et al. ........... 800/317.4
2003/0093836 A1   5/2003 Stevens et al.
2004/0117874 A1   6/2004 Yang et al.

OTHER PUBLICATIONS

Kasahara et al (1999, NCBI Accession No. AB025109).*
Bowie et al, Science 247:1306-1310, 1990.*
McConnell et al, Nature 411 (6838):709-713, 2001.*
Kagaya et al (1995, Mol. Gen. Genet. 248 :668-674).*
Fourgoux-Nicol et al (1999, Plant Molecular Biology 40 :857-872).*
Takei et al (2001, Journal of Biological Chemistry 276(28):26405-26410).*
Li et al (2003, J. Plant Physiology 160:1059-1063).*
Khodakovskaya et al, 2006, Plant Cell Rep 25:1181-1192.*
Sun, et al., The *Arabidopsis AtIPT8/PGA22* Gene Encodes an Isopentenyl Transferase That is Involved in De Novo Cytokinin Biosynthesis, *Plant Physiology*, 131: 167-176 (Jan. 2003).

(Continued)

*Primary Examiner*—Stuart F. Baum
(74) *Attorney, Agent, or Firm*—Hamilton, Brook, Smith & Reynolds, P.C.

(57) ABSTRACT

A unique fusion gene is disclosed which is useful for transforming a wide range of plants, resulting in a significant alteration of the plant phenotype with respect to shoot and floral tissue response, but not affecting root growth or function. The gene construct includes an ACC oxidase promoter to drive an ipt coding sequence that expresses IPT at certain stages of plant maturation and in certain tissues of the shoot. Exemplary transformations include chrysanthemum and tobacco, both of which exhibit increased branching in the vegetative shoot and increased bud count in the generative shoot.

21 Claims, 28 Drawing Sheets

OTHER PUBLICATIONS

Takei, et al., "Identification of Genes Encoding Adenylate Isopentenyltransferase, a Cytokinin Biosynthesis Enzyme, in *Arabidopsis thaliana*," *Journal of Biological Chemistry*, 276(28): 26405-26410 (Jul. 2001).

Abel, S. and Theologis, A., "Early Genes and Auxin Action," *Plant Physiol* 111:9-17 (1996).

Abel, S., et al., "*ASC4*, a Primary Indoleacetic Acid-responsive Gene Encoding 1-Aminocyclopropane-1-carboxylate Synthase in *Arabidopsis thaliana*,"*The J. of Biological Chemistry*, 270(32):19093-19099 (1995).

Ainley, W. M., et al. "Regulatable Endogenous Production of Cytokinins up to 'Toxic' Levels in Transgenic Plants and Plant Tissues," *Plant Molecular Biology*, 22:13-23, (1993).

Akiyoshi, D. E., et al., "T-DNA of Agrobacterium Tumefaciens Encodes an Enzyme of Cytokinin Biosynthesis," *Proc. Natl. Acad. Sci.* 81: 5994-5998 (1984).

Alexander, Lucille and Grierson, Don, "Ethylene Biosynthesis and Action in Tomato: A Model for Climacteric Fruit Ripening," *J of Experimental Botany*, 53(377): 2039-2055 (2002).

An, G., et al., "Transformation of Tobacco, Tomato, Potato, and *Arabidopsis thaliana* Using a Binary Ti Vector System," *Plant Physiol.*, 81: 301-305 (1986).

Barry, C. S., et al., "Differential Expression of the 1-Aminocyclopropane-1-Carboxylate Oxidase Gene Family of Tomato," *The Plant Journal*, 9(4): 525-535 (1996).

Beckman, E.P., et al., "Differential Expression of Four Genes Encoding 1-aminocyclopropane-1-carboxylate Synthase in *Lupinus albus* During Germination, and in Response to Indole-3-acetic Acid and Wounding," *Planta* 211:663-672 (2000).

Blume, B., at al., "Identification of Transposon-like Elements in Noncoding Regions of Tomato ACC Oxidase Genes," *Mol. Gen. Genet.*, 254: 297-303 (1997).

Blume, Beatrix and Grierson, Don, "Expression of ACC Oxidase Promoter-GUS Fusions in Tomato and Nicotiana Plumbaginifolia Regulated by Developmental and Environmental Stimuli," *The Plant Journal*, 12(4): 731-746 (1997).

Boyle, T. H., "BA Influences Flowering and Dry-matter partitioning in Shoots of 'Crimson Giant' Easter Cactus," *HortScience*, 30(2): 289-291 (1995).

Boyle, T.H., et al., "Influence of Photoperiod and Growth Regulators on Flowering of *Rhipsalidopsis gaertneri*," *J. Amer. Soc. Hort. Sci. 1139*(1):75-78 (1988).

Campos, K.A. and Kerbauy, G.B., "Thermoperiodic Effect on Flowering and Endogenous Hormonal Status in Dendrobium (Orchidaceae)," *J. of Plant Physiol.*, 161:1385-1387 (2004).

Chandler, S., "Commercialization of Genetically Modified Ornamental Plants," *J. Plant Biotechnology* 5(2):69-77 (2003).

Chang, H., et al., "Overproduction of Cytokinins in Petunia Flowers Transformed with $P_{SAG12}$-IPT Delays Corolla Senescene and Decreases Sensitivity to Ethylene[1]," *Plant Physiology* 132:2174-2183 (2003).

Chory, J., el al., "A Role for Cytokinins in De-Etiolation in *Arabidopsis det* Mutants Have an Altered Response to Cytokinins," *Plant Physiol.* 104:339-347 (1994).

Clark, D.G., et al., "Drought-induced Leaf Senescence and Horticultural Performance of Transgenic $P_{SAG12}$-IPT Petunias," *J. Amer. Soc. Hort. Sci. 129*(1):93-99 (2004).

Coenen, C. and Lomax, L. T., "The Diageotropica Gene Differentailly Affects Auxin and Cytokinin Responses Throughout Development in Tomato," *Plant Physiol.*, 117: 63-72 (1998).

Coenen, C. et al., "Cytokinin Inhibits a Subset of Diageotropica-Dependent Primary Auxin Responses in Tomato," *Plant Physiol.*, 131: pp. 1692-1704 (2003).

Corbesier, L., et al., "Cytokinin Levels in Leaves, Leaf Exudate and Shoot Apical Meristem of *Arabidopsis thaliana* During Floral Transition," *J. of Experimental Botany* 54(392):2511-2517 (2003).

Dewitte, W., et al., "Dynamics of Cytokinins in Apical Shoot Meristems of a Day-Neutral Tobacco During Floral Transition and Flower Formation[1]," *Plant Physiology* 119:111-121 (1999).

Gan, S. and Amasino, R. M., "Inhibition of Leaf Senescence by Autoregulated Production of Cytokinin," *Science*, 270: 1986-1988 (1995).

Gan, S. and Amasino, R. M.., "Making Sense of Senescence[1] Molecular Genetic Regulation and Manipulation of Leaf Senescence," *Plant Physiol.*, 113: 313-319, 1997.

Goldsbrough, A., et al., "Salicylic Acid-inducible Binding of a Tobacco nuclear Protein to a 10 BP Sequence which is Highly Conserved Amongst Stress-inducible Genes," *The Plant Journal*, 3(4): 563-571 (1993).

Guilfoyle, T., J., et al., "The ARF Family of transcription Factors and Their Role in Plant Hormone-responsive Transcription," *CMLS, Cell. Mol. Life Sci.*, 54:619-627 (1998).

Hobbie, L., et al., "Molecular Genetics of Auxin and Cytokinin," *Plant Molecular Biology 26*:1499-1519 (1994).

Hong, J., C., et al., "Isolation of Two Soybean G-box Binding Factors which Interact with a G-box Sequence of an Auxin-responsive Gene," *The Plant Journal*, 8(2): 199-211 (1995).

Itzhaki, H., et al., "An Ethylene-responsive Enhancer Element is Involved in the Senescence-related Expression of the Carnation Glutathione-S-transferase (GST1) Gene," *Proc. Natl. Acad. Sci.*, 91: 8925-8929 (1994).

Jacqmard, et al., "In Situ Localisation of Cytokinins in the Shoot Apical Meristem of *Sinapis alba* at Floral Transition," *Planta 214*:970-973 (2002).

Khodakovskaya, M., et al., Effects of cor15a-IPT Gene Expression on Leaf Senescence in transgenic Petunia χ hybrida and Dendranthema χ grandiflorum, *J of Experimental Botany*, 56(414): 1165-1175 (2005).

Khodakovskaya, M., et al., "Expression of IPT Gene Controlled by an Ethylene and Auxin Responsive Fragment of the LEACO1 Promoter Increases Flower Number in Transgenic Nictiana Tabacum," *Plant Cell Rep 25*: 1181-1192 (2006).

Kieber, J.J., "Cytokinins," *The Arabidopsis Book*:1-25 (2002).

Kim, J., H., et al., "IAA and $N^6$-Benzyladenine Inhibit Ethylene-Regulated Expression of ACC Oxidase and ACC Synthase Genes in Mungbean Hypocotyls," *Plant Cell Physiol.* 42(10): 1056-1061 (2001).

Klee, H., et al., "*Agrobacterium*-Mediated Plant Transformation and its Further Applications to Plant Biology," *Ann. Rev. Plant Physiol. 38*:467-486 (1987).

Lau, OL., et al. "Effect of Different Cytokinins on Ethylene Production by Mung Bean Hypocotyls in the Presence of Indole-3-Acetic Acid or Calcium Ion," *Physiol. Plant.*, 39: 1-3 (1997).

Lejeune, P., et al., "Cytokinins in Phloem and Xylem Saps of *Sinapis alba* During Floral Induction," *Plysiologia Plantarum 90*:522-528 (1994).

Li, C. and Bangerth, F., "Stimulatory Effect of Cytokinins and Interaction with IAA on the Release of Lateral Buds of Pea Plants from Apical Dominance," *J. Plant Physiol. 160*:1059-1063 (2003).

Li, Y., et al., "Altered Morphology in Transgenic Tobacco Plants That Overproduce Cytokinins in Specific Tissues and Organs," *Developmental Biology*, 153: 386-395 (1992).

Liu, Jin-Hao et al., "Differential and Wound-inducible Expression of 1-Aminocyloprpane-1-carboxylate Oxidase Genes in Sunflower Seedling," *Plant Molecular Biology*, 34: 923-933, (1997).

McCabe, M.S., et al., "Effects of $P_{SAG12}$-IPT Gene Expression on Development and Senescence in Transgenic Lettuce," *Plant Physiology 127*:505-516 (2001).

Medford, J.I., et al., "Alterations of Endogenous Cytokinins in Transgenic Plants Using a Chimeric lsopentenyl Transferase Gene," *The Plant Cell 1*:403-413 (1989).

Menkens, A.E., "The G-box: a Ubiquitous Regulatory DNA Element in Plants Bound by the GBF Family of bZIP Proteins," *TIBS 20*:506-510 (1995).

Miyawaki, K., et al., "Expression of Cytokinin Biosynthetic Isopentenyltransferase Genes in *Arabidopsis*: Tissue Specificity and Regulation by Auxin, Cytokinin, and Nitrate," *The Plant Journal 37*:128-138 (2004).

Mok, D.W.S. and Mok, M.C., "Cytokinin Metabolism and Action," *Annu. Rev. Plant Physiol. Mol. Biol. 52*:89-118 (2001).

Montgomery, J., et al., "Identification of an Ethylene-responsive Region in the Promoter of a Fruit Ripening Gene," *Proc. Natl. Acad. Sci.*, 90: 5939-5943 (1993).

Moon, H. and Callahan, A.M., "Developmental Regulation of Peach ACC Oxidase Promoter-GUS Fusions in Transgenic Tomato Fruits," *J. of Experimental Botany* 55(402):1519-1528 (2004).

Nagel, L., et al., "Cytokinin Regulation of Flower and Pod Set in Soybeans (*Glycine max* (L.) Merr.)," *Annals of Botany* 88:27-31 (2001).

Norcini, J. G., et al., "Pest Management in the U. S. Greenhouse and Nursery Industry: III. Plant Growth Regulation," *HortTechnology*, 6(3): 207-210 (1996).

Papadopoulou, E., et al., "Effect of Modified Endogenous Ethylene Production on Sex Expression, Bisexual Flower Development and Fruit Production in melon (*Cucumis melo* L.)," *Sex Plant Reprod* 18:131-142 (2005).

Remington, D. L., et al., "Contrasting Modes of Diversification in the Aux/IAA and ARF Gene Families[1]," *Plant Physiol.* 135: 1738-1752 (2004).

Roiv, Joseph et al., "Autoinhibition of Ethylene Production in Citrus Peel Discs[1] Suppression of 1-Aminocyclopropane-1-carboxylic Acid Synthesis," *Plant Physiol.*, 69: 687-690 (1982).

Romano, C.P. and Klee, H., "Hormone Manipulation in Transgenic Plants," in *Transgenic Plants: Fundamentals and Applications*, A. Hiatt, Eds. (MI: Marcel Dekken, Inc.), 23-36 (1993).

Sakakibara, H., "Cytokinins: Activity, Biosynthesis, and Translocation," *Annu. Rev. Plant Biol.* 57:431-449 (2006).

Schroeder, K.R., et al., "Response of *Nicotiana alata* to Insertion of an Autoregulated Senescence-inhibition Gene," *J. Amer. Soc. Hort. Sci* 125(5):523-530 (2001).

Smart, C., et al., "Delayed Leaf Senescence in tobacco Plants Transformed with *tmr*, a Gene for Cytokinin Production in *Agrobacterium*," *The Plant Cell*, 3: 647-656 (1991).

Smigocki, A., et al., "Cytokinin-mediated Insect Resistance in *Nicotiana* Plants Transformed with the *ipt* Gene," *Plant Molecular Biology* 23:325-335 (1993).

Smigocki, A.C., "Cytokinin Content and Tissue Distribution in Plants Transformed by a Reconstructed Isopentenyl Transferase Gene," *Plant Molecular Biology* 16:105-115 (1991).

Song, J.-D., et al., "Developmental Regulation of the Expression of 1-Aminocyclopropane-1-Carboxylic Acid (ACC) Synthase and ACC Oxidase Genes in Hypocotyls of Etiolated Mung Bean Seedlings," *Plant Science* 168:1149-1155 (2005).

Swarup, R., et al., "Auxin Cross-Talk: Integration of Signalling Pathways to Control Plant Development," *Plant Molecular Biology* 49:411-426 (2002).

Tang, X., et al., "Organization and Structure of the 1-aminocyclopropane-1-carboxylate Oxidase Gene Family from *Petunia hybrida*," *Plant Molecular Biology*, 23: 1151-1164 (1993).

Thomas, J.C., et al., "Light-Induced Expression of *ipt* from *Agrobacterium tumefaciens* Results in Cytokinin Accumulation and Osmotic Stress Symptoms in Transgenic Tobacco," *Plant Molecular Biology* 27:225-235 (1995).

Ulmasov, T., et al, "ARF1, a Transcription Factor That Binds to Auxin Response Elements," *Science* 276: 1865-1868 (1997) www.sciencemag.org.

Ulmasov, T., et al., "Activation and Repression of Transcription by Auxin-response Factors," *Proc. Natl. Acad. Sci.*, 96: 5844-5849 (1999).

Ulmasov, T., et al., "Composite Structure of Auxin Response Elements," *The Plant Cell*, 7: 1611-1623 (1995).

Ulmasov, T., et al., "Dimerization and DNA Binding of Auxin Response Factors," *The Plant Journal* (3): 309-319 (1999).

Vendrell, M., et al., "Inhibition of Ethylene Production on Banana Fruit Tissue by Ethylene Treatment," *Aust. J Biol. Sci.* 24 : 885-895 (1971).

Vogel, J. P., et al., "Isolation and Characterization of *Arabidopsis* Mutants Defective in the Induction of Ethylene Biosynthesis by Cytokinin," *Genetics* 149: 417-427 (1998).

Vogel, J. P., et al., "Recessive and Dominant Mutations in the Ethylene Biosynthetic Gene *ACS5* of *Arabidopsis* Confer Cytokinin Insensitivity and Ethylene overproduction, respectively," *Proc. Natl. Acad. Sci.*, 85: 4766-4771 (1998).

Yang, S.F. and Hoffman, N.E., "Ethylene Biosynthesis and Its Regulation in Higher Plants," *Ann. Rev. Plant Physio.* 35:155-189 (1984).

Yoshii, H., et al., "Regulation of Auxin-induced Ethylene Biosynthesis Repression of Inductive Formation of 1-aminocycloprppane-1-carb-Oxylate Synthase by Ethylene," *Plant Cell. Physiol.*, 23: 639-649 (1982).

Zauberman, G. and Fuchs, Y., "Ripening Processes in Avocados Stored in Ethylene Atmosphere in Cold Storage[1,2]," *J. Amer. Soc. Hort. Sci.*, 98(5): 477-480 (1973).

Zeroni, M., et al., "Autoinhibition of Ethylene Formation in Nonripening Stages of the fruit of Sycomore Fig (*Ficus sycomorus* L.)," *Plant Physiol.*, 57: 647-650 (1976).

Mercier, R.W., "Apoplastic invertase: a dissection of its role in photosynthate translocation and partitioning", *Cell Biology Thesis, Ph.D.*, University of Connecticut, pp. i-xi and 1-286, 1998.

Murashige, Toshio, et al., "A Revised Medium for Rapid Growth and Bio Assays with Tobacco Tissue Cultures", vol. 15, Physiolgia Plantarum, pp. 473-497, 1962.

\* cited by examiner

Typical aco-ipt plant

Typical wild-type plant with strong apical dominance

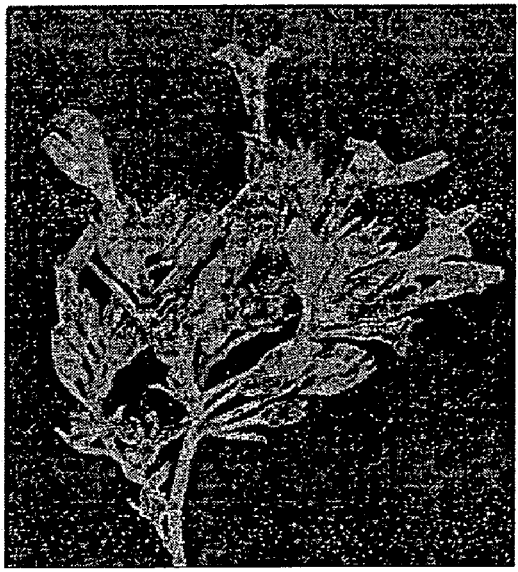
FIG. 13A  FIG. 13B
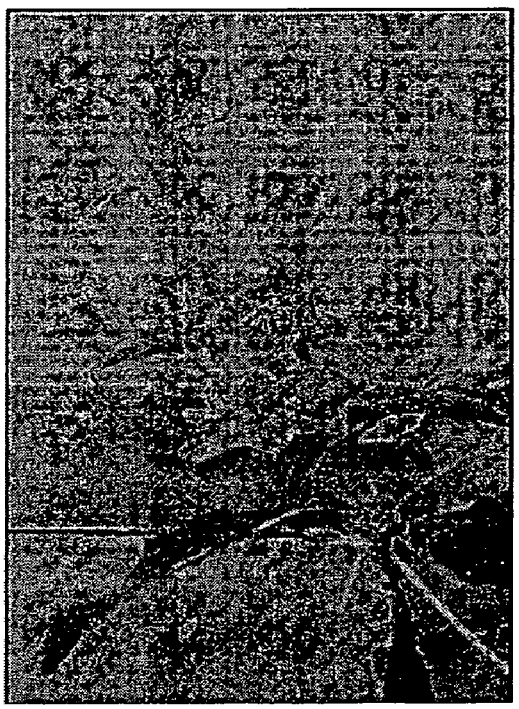
FIG. 13C  FIG. 13D

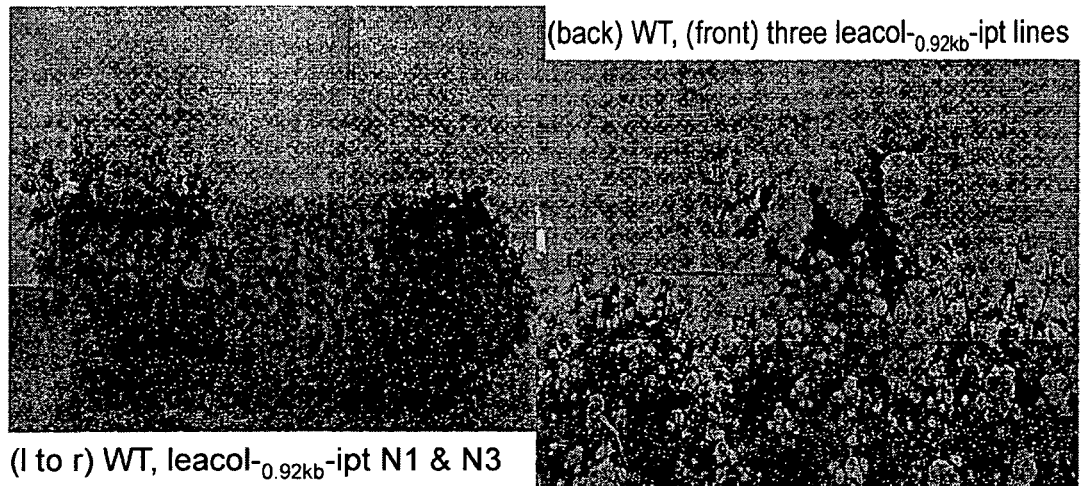
Cytokinin concentrations in wild-type & selected leacol-0.92kb-ipt lines. Note dramatic increase in flowering shoot
| Growth Phase of Shoot Tissue | Line | Cytokinin pool (*pmol/g* DW) | | |
|---|---|---|---|---|
| | | Total active | Total storage | Total deactivated |
| Vegetative | WT | 47.8 | 54.8 | 38 |
| Vegetative | Leacol-0.92kb-IPT N1 | 38.8 | 70.9 | 72.8 |
| Vegetative | Leacol-0.92kb-IPT N14 | 80.2 | 107.6 | 102.6 |
| Vegetative | Leacol-0.92kb-IPT N5 | 48.4 | 49.1 | 45 |
| Flowering | Leacol-0.92kb-IPT N5 | 185.2 | 220.2 | 2909 |
FIG. 15

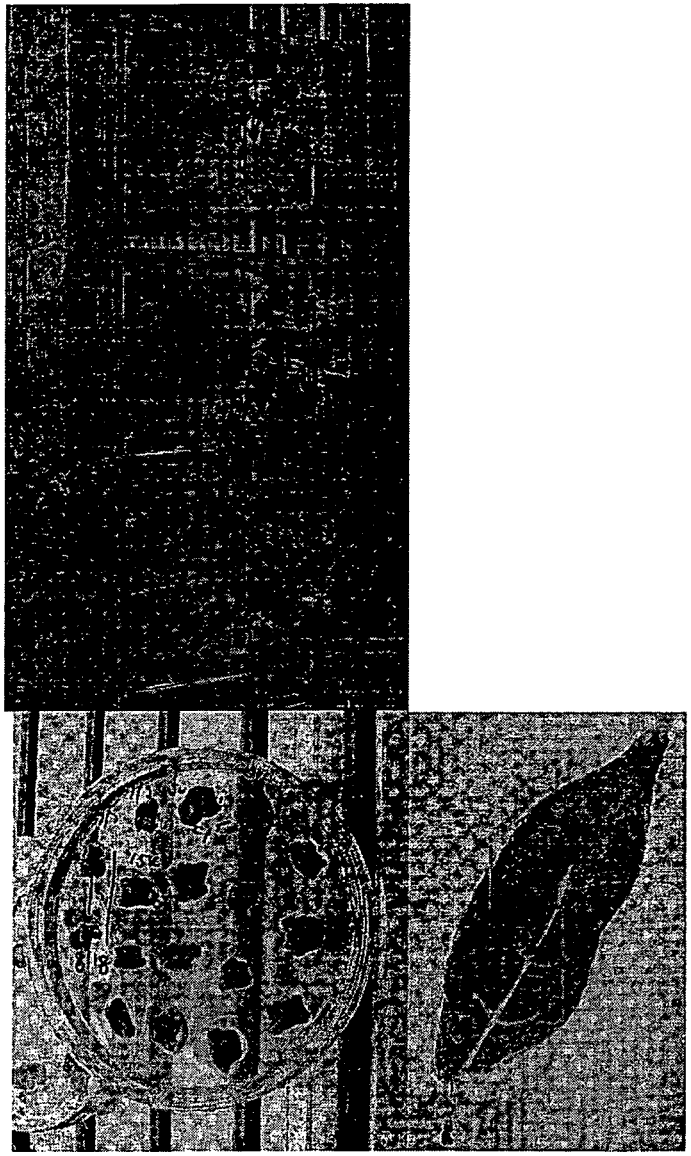

Poinsettia transformation: (top left) Stem internode explants were inoculated with *Agrobacterium* carrying the transgene of interest. TDZ was used to induce callus, which then gave rise to shoot initials. Transgenic tissue was selected using kanamycin & transgenic shoots gradually develop from the transgenic calli (top right). Leaf from 'Red Success' plant transformed with 35s-gus gene (bottom). The blue colored-stain is a visual indicator of GUS activity.

FIG. 18

SEQ ID NO: 1

5'-GGTTGAGTTGTTTCCCTCTG-3'

FIG. 19

SEQ ID NO:2

5'-GGTAAAGTGTTTTCCTAAGTG-3'

FIG. 20

SEQ ID NO:3

GGTCCAACTTGCACAGGAAAG-3'

FIG. 21

SEQ ID NO: 4

GGCTTGCCTACTGGAAGCTTA-3'

FIG. 22

SEQ ID NO:5 (ipt gene, 723 bp)

ATGGATCTGCGTCTAATTTTCGGTCCAACTTGCACAGGAAAGACGTCGACCGGGTAGCTCTTGCCCAGC
AGACTGGGCTTCCAGTCCTTTCGCTCGATCGGGTCCAATGTTGTCCTCAGCTGTCAACCGAAGCGGACG
ACCAACAGTGGAAGAACTGAAAGGAACGAGCCGTCTATACCTTGATGATCGGCCTCTGGTGAAGGGTATC
ATCGCAGCCAAGCAAGCTCATGAAACTGAAAGGCTGTATAATTATGAGCCCACGGCGGGCTTA
TTCTTGAGGGAGGATCTATCTCGTTGCTCAAGTGCATGGCCAAAGCAGTTATTGGAGTGCGGATTTTCG
TTGGCATATTATTCGCCACGAGTTAGCACACGAGGAGACCTTCATGAACGTGGCCAAGGCCAGAGTTAAG
CAGATGTTACGCCCCGCTTCAGGCCCTTTCTATTATCCAAGAGTTGGTTGATCTTTGGAAAGAGCCCTCGGC
TGAGGCGCATACTGAAAGAGATCGATGGATATCGATATCGTTGTTTGTTAGCCATGTGTTTGTTAGCCAGAACCAGATCAC
ATCCGATATGCTATTGCAGTTGACGCCAGATCGGAGGATAAGTTGATTCATGGATCGCTCAGGAGTAT
CTCATCCATGCACGCCGACAAGAACAGAAATTCCCTCGAGTTAACGCCGCTTACGACGGATTCGAAG
GTCATCCATTCGGAATGTATTAG

FIG. 23

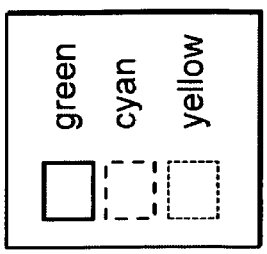

SEQ ID NO: 6 (821 bp leaco1 promoter fragment from position 1035 to position 1855 of SEQ ID NO:9)

1035 gtgaacctctcatgtattccgagtgaattggttgaggttgtttccc
1081 tctgtatttgtactctcatgtttatagtggattgc[tcatttcctt]tgtggacgtaggtc
1141 gattgaccgaaccacgtaaatcttgtctttggtatatttctcg[ttgtcttctt]ac
1201 tcgtggtctttcgaggtttgctttcgctagcttccgcgttacacctgcttattgcggtc
1261 ctaacagagttcgatgggttgaatctataaaagaaaaatatactcgtgattcacgatta
1321 tttatatgaaaatataataatattgaattccttgctatttcttatgtttacgtctt
1381 at[atttcaaa]ttattccaccaatactgacaagcccatctctaggaaattcatac
1441 aattttttttgttaactagtaaattgcagcttaaagattattgtaaaattca
1501 aggcaacttcctcaagtactacaactcattgtaacacatcccagtcctaaagt
1561 tttataaaatttgacacatgaaacatagcacaataaatttagtactatgcagccatg
1621 gcccataagccatcatgtattagtcaaaatgggtcctttcaaattgtcttgatccc
1681 aaaatcccttttgtaggtaagatggttcaacaaggaactatgaactcttaaggtagacttgg
1741 actcatagacttgtcataactgtcataaagactttggaatataataattattcatttaaatta
1801 taattctctactttaatatctctac[ata]aataccctttcaaagccctcattatt

FIG. 24

SEQ ID NO:7 (821 bp Leaco1 promoter sequence plus 97 bp of 5' UTR leader sequence from position 1035 to position 1952 of SEQ ID NO: 9)

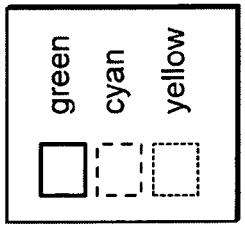

*1035gtgaacctctcatgtattccgagtgaattggttgaggttgtttccc*
*1081tctgtatttgtactctcatgtttatagtggattgc[tcatttctt]tgtggacgtaggtc*
*1141gattgaccgaaccacgttaaatctttgtctttggtatatttctcg[ttgtctttctt]ac*
*1201tcgtggtcttcgagggttgcttgctagcttccgcgtttacacctgcttattgcggtc*
*1261ctaacagagttcgatgggttgaatctataaaagaaaaatatactcgtgattcacgatta*
*1321tttatatgaaaatataaatattgaattccttgctatttcttatgtttacgtcttt*
*1381at[fatttcaaa]ttattccaccaatactgacaagccctaggccatctctaggaaaatcatac*
*1441aattttttttgttgttaactagtaaattggcagcctaaagattatgtaaaattca*
*1501aggcaacttcctcaagtactacaactacattgtaacatcccagtcaaagtgtcctaaaat*
*1561tcgtggtcttcgagggttgcttgctagcttccgcgtttacacctgcttattgcggtc*
*1621gcccataagccatcatgtattatagtcaaaatgggtccttt[tcaat]tgtcttgatccc*
*1681aaaatccctttgtaggtaagatggttcaacaaggaactatgactcttaaggtagacttgg*
*1741actccatagacttgtcataacttcataaagacttggaataataattattcatttaaata*
*1801taattctctactttaatatctttctact[atatajaatacccttcaaagccctcattatt][97bpof5'UTRleader] *tgtac*
*1861atcaaacattgatatcttcaatctttgtattcacatattctatattattcaata*
*1921cacttaggaaaaacacttaccaagaaaattaag*

FIG. 25

SEQ ID NO:8 (SEQUENCE OF CHIMERA LEACO1-$_{0.918kb}$-IPT-NOS Gene Construct with Restriction Sites) Complete Sequence:

[LEACO1-$_{0.918kb}$ promoter fragment form the L. esculentum LEACO1 gene]-[HindIII: AAGCTT]–
GTGAACCTCTCATGTATTCCGAGTGAATTGGTTGAGGTTGTTTCCCTCTGTATTTTGT
ACTCTCATGTTTATAGTGGATTGCTCATTTCCTTTGTGGACGTAGGTCGATTGACCGA
ACCACGTTAAATCTTTGTGTCTTTTGGTATATTTCTCGTTGTCTTCTTACTCGTGGTCT
TTCGAGGTTTGCTTTGCTAGCTTCCGCGTTTACACCTGCTTATTTGCGGTCCTAACAG
AGTTCGATGGGTTGAATCTATAAAAAGAAAAATATACTCGTGATTCACGATTATTTA
TATGAAAATATAATAAATATTGAATTTCCTTTGCTATTTCTTATGTTTACGTCTTTAT
ATTTCAAATTATTCCACCAATACTGACAAGCCCTAGGCCATCTCTAGGAAATTCATA
CAATTTTTTTTTGTTGTTAACTAGTTAAATTGGCAGCCTTAAAGATTATTGTAAAAT
TCAAGGCAACTTCCTCAAGTACTACAACTACATTGTAACATCCCAGTCAAAGTGTCC
TAAAATTTTATAAAATTTGACACATGAAACAATAGCACAATAAATTTTAGTACTATT
GCAGCCATGGCCCATAAGCCATCATGTATTATAGTCAAAATGGGTCCTTTTCCAATT
TGTCTTGATCCCAAAATCCCTTTGTAGGTAAGATGGTTCAACAAGGAACTATGACTC
TTAAGGTAGACTTGGACTCATAGACTTGTCATAACTCATAAAGACTTGGAATATAAT
AATTATTCATTTAAATTATAATTCTCTACTTTAATATCTTCTACTATAAATACCCTTTC
AAAGCCTCATTATTTGTACATCAAACATTGATATTCATCTCTTCAATCTTTTGTATTC
ACATATTCTATTTATTCAATACACTTAGGAAAACACTTTACCAAGAAATTAAG–[SALI:
GTCGAC]–[ipt coding sequence: 688-1410 Agrobacterium tumefaciens gene for isopentenyl
transferase, complete cds]–ATGGATCTGCGTCTAATTTTCGGTCCAACTTGCACAGGAAA
GACGTCGACCGCGGTAGCTCTTGCCCAGCAGACTGGGCTTCCAGTCCTTTCGCTCGA
TCGGGTCCAATGTTGTCCTCAGCTGTCAACCGGAAGCGGACGACCAACAGTGGAAG
AACTGAAAGGAACGAGCCGTCTATACCTTGATGATCGGCCTCTGGTGAAGGGTATC
ATCGCAGCCAAGCAAGCTCATGAAAGGCTGATGGGGGAGGTGTATAATTATGAGGC
CCACGGCGGGCTTATTCTTGAGGGAGGATCTATCTCGTTGCTCAAGTGCATGGCGCA
AAGCAGTTATTGGAGTGCGGATTTTCGTTGGCATATTATTCGCCACGAGTTAGCACA
CGAGGAGACCTTCATGAACGTGGCCAAGGCCAGAGTTAAGCAGATGTTACGCCCCG
CTTCAGGCCTTTCTATTATCCAAGAGTTGGTTGATCTTTGGAAAGAGCCTCGGCTGA
GGCGCATACTGAAAGAGATCGATGGATATCGATATGCCATGTTGTTTGTTAGCCAGA
ACCAGATCACATCCGATATGCTATTGCAGCTTGACGCAGATATGGAGGATAAGTTGA
TTCATGGGATCGCTCAGGAGTATCTCATCCATGCACGCCGACAAGAACAGAAATTCC
CTCGAGTTAACGCAGCCGCTTACGACGGATTCGAAGGTCATCCATTCGGAATGTATT
AG–[SacI: [G]AGCT[C]]–[NOS Sequence: 7501-7756 Broad host range plasmid Bin 19,
complete sequence]–CCCGATCTAGTAACATAGATGACACCGCGCGCGATAATTTATCC
TAGTTTGCGCGCTATATTTTGTTTTCTATCGCGTATTAAATGTATAATTGCGGGACTC
TAATCATAAAAACCCATCTCATAAATAACGTCATGCATTACATGTTAATTATTACAT
GCTTAACGTAATTCAACAGAAATTATATGATAATCATCGCAAGACCGGCAACAGGA
TTCAATCTTAAGAAACTTTATTGCCAAATGTTTGAACGATC–[EcoR1: GAATTC]
(SEQ ID NO:8)

Figure 26

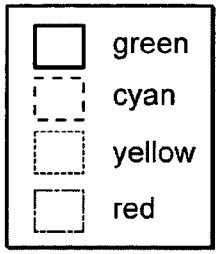
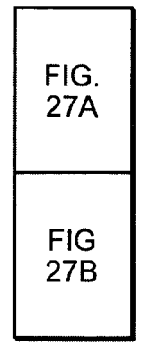

FIG. 27

SEQ ID NO: 9 leaco-1 gene sequence
```
     aaatttgata gattcagttt ttatgttttt agtgctgatt acaacattga aattctaaat
 61  ttagaattta atatttatta aatgttagtg catttataca aataacatat tacatctcaa
121  ataatat tga gtttgttaga ttttatttgc cctgatttct tatcataaat aggttttcct
181  tttaggaaaa ggttttgaat tgactattct tttttggta ggaaaaagtt taggactcta
241  taaatagagg catgttcctt ctaacttaat tagcattcac aatgtagttt taagggcttt
301  gagagttttg gttagaggga gaatttgtga acctctcatg tattccgagt gaattggttg
361  aggttgtttc cctctgtatt ttgtactctc atgtttatag tggattgc [tc atttcctt] tg
421  tggacgtagg tcgattgacc gaaccacgtt aaatttttgt gtcttttggt atatttcc [tg
481  ttcttctt] ac tcgtggtctt tcgaggtttg ctttgctagc ttccgcgttt acacctgctt
541  attttcggtc ctaacaagtg gtatcagagc cagattcaat aatggagtca ggtgtagtgg
601  ttcgataatc gatgattgaa ccaagttaga aagaggtgtt catcttgacg ggtgtagttc
661  tagccgcaac cttttgaca gtaatgaaga ttttgatgga gaaattgttt cagagaggt
721  ctctgtgttg agacataaat ttgtaaagg agattatgga gaggagaagc aagttgttga
781  agattaagta aagaaggtgg acaaatctat tttgtcagaa attcaggcca aggggagat
841  ttgttgggtt ttatttgccc tgatttttta ccataaaatag gttttccttt aaggaaaagg
901  ttttgaattg actattcttt ttttggtagg aaaaggttta ggattctata aatagaggca
961  tgttccttct aacttaatta gcattcacaa tgtagtttta agggctttga gagttttggt
1021 tagagggaga attt [start –918bp fragment] gtgaac ctctcatgta
ttccgagtga attggttgaggttgtttccc
1081 tctgtatttt gtactctcat gtttatagtg gattgc [tcat ttcctt] tgtg gacgtaggtc
1141 gattgaccga accacgttaa atctttgtgt cttttggtat atttctcg [tt gtcttctt] ac
1201 tcgtggtctt tcgaggtttg ctttgctagc ttccgcgttt acacctgctt atttgcggtc
1261 ctaacagagt tcgatgggtt gaatctataa aaagaaaaat atactcgtga ttcacgatta
1321 tttatatgaa aatataataa atattgaatt tcctttgcta tttcttatgt ttacgtcttt
1381 at [atttcaaa] ttattccacc aatactgaca agccctaggc catctctagg aaattcatac
1441 aatttttttt ttgttgttaa ctagttaaat tggcagcc ttaaagattatt gtaaaattca
1501 aggcaacttc ctcaagtact acaactacat tgtaacatcc cagtcaaagt gtcctaaaat
1561 tttataaaat ttgacacatg aaacaatagc acaataaatt ttagtactat tgcagccatg
1621 gcccataagc catcatgtat tatagtcaaa atgggtcctt tt[caaa]ttg tcttgatccc
1681 aaaatcccctt tgtaggtaag atggttcaac aaggaactat gactcttaag gtagacttgg
1741 actcatagac ttgtcataac tcataaagac ttggaatata ataattattc atttaaatta
1801 taattctcta ctttaatatc ttcta[tata]aataccctt caaagcctca ttatt [start 97bp of 5'
UTR leader sequence] tgtac
```

FIG. 27A 1861 atcaaacatt gatattcatc tcttcaatct tttgtattca catattctat ttattcaata
1921 cacttaggaa aacactttac caagaaattaag [codon initiation sequence starts]atg gagaa cttcccaatt attaacttgg
1981 aaaagctcaa tggagatgag agagccaaca ccatggaaat gatcaaagat gcttgtgaga
2041 attggggctt ctttgaggta atcataaatt acataaacat attaatatgt ttgtttcaat
2101 ttatcagtca tacttttctc tgttttaaaa ttaatgtcac tttcaatatt taataattcg
2161 catgacatgt ttataacaca acaagatata ggttacattt tgatacatta tatataactt
2221 ctgtcacacg actcaaaagt ctttcttaat ttcttgaatt caatgatcga tcaaactaag
2281 acacgtaaaa tgaaacgggg aatagtaatt ctgtttgctt atgtgatcat tgtagttggt
2341 gaaccatgga attccacatg aagtaatgga cacagtagag aaaatgacaa agggacatta
2401 caagaagtgc atggaacaga ggtttaagga actagtggca agtaagggac ttgaggctgt
2461 tcaagctgag gttactgatt tagattggga aagcactttc ttcttgcgcc atcttcctac
2521 ttctaatatc tctcaagtac ccgatcttga cgaagaatac aggtacatac atgtgtccta
2581 catattgcgt atataataaa taaacacaaa atttaagtta tatacgctga cagtataact
2641 aattataatg ttgtaccaaa tgatgcagag aggtgatgag agattttgct aaaagattgg
2701 agaaattggc tgaggagtta cttgacttac tctgtgaaaa tcttggactt gaaaaaggtt
2761 acttgaaaaa tgccttttat ggatcaaaag gtcccaactt tggtactaaa gttagcaact
2821 atccaccatg tcctaagccc gatttgatca agggactccg cgctcataca gacgcaggag
2881 gcatcatact tctgttccaa gatgacaaag tgagtggcct tcaactcctc aaagacgagc
2941 aatggatcga tgttcctccc atgcgccact ctattgtggt taaccttggt gaccaacttg
3001 aggtacaaga ttcactaagt gtgtgtgttt ttatcactat aacttagaag tagtaactaa
3061 aaatggtatt aatgaaatgt tataaaaaca ggtgatcact aacgggaagt acaagagtgt
3121 gctgcacaga gtaattgcac aaacagacgg gacacgaatg tcattagcct cattttacaa
3181 tccaggaagt gatgcagtaa tatatccagc aaaaactttg gttgaaaaag aggcagagga
3241 aagtacacaa gtgtatccaa agtttgtgtt tgatgattac atgaagttat atgctggact
3301 caagtttcaa gccaaagagc caagatttga agcaatgaag gcaatggaaa gtgatccaat
3361 tgcaagtgct tagatcccaa ttcaattaaa aaaattggtg tttgaaaaat atatttaaat
3421 atagcaatct atgtatacac attatttgct cttcttatgt atggtagaat aaagttagta
3481 ttaaaaaaga ttgtgatttg ctgcatatgt atcaaaaaga gtcctaatat ttgtatctat
3541 aaataaggtg ccttctagtg aaattataca aataataatt tggagtgtat tgttctttct
3601 catgtaattt aacttttaag tatcttactt tacaatatac tgttcactta ttgaacatat
3661 tgagtgatat attgactcaat

FIG. 27B

SEQ ID NO:10 (8 BP ethylene responsive motif)

AA/TTTCAAA     FIG. 28

SEQ ID NO:11 (10 bp TCA stress inducible motif, allowing two substitutions)

TCATCTTCTT     FIG. 29

Figure 30: Leaco1₀.₈₂₁ₖᵦ promoter sequence showing location of various motifs associated with gene response to specific hormones.

gtgaacctctcatgtattccgagtgaattggttgaggttgtttcc<u>ctctgt</u>attttgtactctcatgtttatagtggattgc<u>tcatttcc</u>tttg
tg<u>gacgt</u>aggtcgattgaccgaacc<u>acgt</u>taaatctttg<u>tgtcttt</u>tggtatatttctcgtt<u>gtcttc</u>ttac<u>tcgtggt</u>ctttcgaggtttg
ctttgctagcttccgcgtttacacctgcttatttgcggtccta<u>acagag</u>ttcgatgggttgaatctataaaaagaaaaatata<u>ctcgtg</u>
attcacgattatttatatgaaaatataataaatattgaatttcctttgctatttcttatgttt<u>acgt</u>ctttat<u>atttcaaa</u>attattccaccaatact
gacaagccctaggccatctctaggaaattcatacaattttttttttgttgttaactagttaaattggcagccttaaagattattgtaaaatt
caaggcaacttcctcaagtactacaactacattgtaacatcccagtcaaagtgtcctaaaattttataaaatttgacacatgaaacaa
tagcacaataaattttagtactattgcagccatggcccataagccatcatgtattatagtcaaaatgggtccttttc<u>caatttgtcttg</u>at
cccaaaatcccttttgtaggtaagatggttcaacaaggaactatgactcttaaggtagacttggactcatagacttgtcataactcata
aagacttggaatataataattattcatttaaattataattctctactttaatatcttctac<u>tataa</u>ataccctttcaaagcctcattatt —
[97bp of 5' UTR leader] — tgtacatcaaacattgatattcatctcttcaatcttttgtattcacatattctatttattcaatac
acttaggaaaacactttaccaagaaattaag [atg] (SEQ ID NO:12)

Auxin responsive motifs:
Reverse orientation of AuxRE=TGTCTC (SEQ ID NO:13), GAGACA (SEQ ID NO:14)
Forward orientation of AuxRE with matches in 5 of 6 bases = TGTCTt (SEQ ID NO:15)

G-Box motifs:
G-Box = CACGTG, CtCGTC (SEQ ID NO:16)
G-Box core element = ACGT (SEQ ID NO:17)

Ethylene motifs:
TCA motif TCATCTTCTT (SEQ ID NO:11) (allowing 2 substitutions) =
                                  TCATtTcCTT (SEQ ID NO:18), TtgTCTTCTT (SEQ ID NO:19)

Ethylene Responsive Element (AA/TTTCAAA (SEQ ID NO:10)) = ATTTCAAA

Figure 30

Sequence ID NO. 13.

TGTCTC

FIG. 31

Sequence ID NO. 14.

GAGACA

FIG. 32

Sequence ID NO. 15.

TGTCTt

FIG. 33

Sequence ID NO. 16.

CtCGTG

FIG. 34

Sequence ID NO. 17

ACGT

FIG. 35

METHOD AND COMPOSITION FOR INCREASING BRANCHING AND FLOWERING RESPONSE IN PLANTS

RELATED APPLICATIONS

The instant application claims the benefit of U.S. Provisional Application No. 60/680,403, filed May 12, 2005. The entire contents of the aforementioned application are hereby incorporated herein by reference.

BACKGROUND

Transgenic or recombinant plants are of increasing interest because of the potential to control phenotypic traits as well as to produce large quantities of commercially useful products. Plants have been employed to overproduce heterologous proteins and in principle can produce a wide range of products, including high value proteins and certain pharmaceuticals. Transgenic plants with visually attractive phenotypes are particularly desirable as a source of economic benefit to horticulturists and to florist retailers, while transgenic agronomic crops with enhanced production traits are of economic benefit to food producers and consumers.

Genetically modified plants for agricultural products are already on the market, including herbicide, insect and virus resistant crop plants. Some of the better-known crops engineered for herbicide resistance include soybeans, maize, rapeseed, sugar beet, rice and cotton. Maize, potatoes, tomatoes and cotton have been modified for insect resistance.

Food source plants can be engineered to improve traits that affect nutritional value; for example, elevated iron in rice and wheat, higher amino acid content in potatoes, seedless fruits and increased carotenoids in rice and tomatoes. Recent efforts have turned to produce recombinant plants with maximal desired plant product at a selected harvest time (patent publication 20030093836, May 15, 2003) or to significantly increase a desired expressed product by targeting protein product accumulation in a targeted tissue (patent publication 20040117874, Jun. 17, 2004). Of particular interest are plants engineered to increase oil production; for example, canola oil, which is considered more healthful than trans fats and oils.

Cytokinins play a role in many growth and developmental processes in plants, such as apical dominance, cell differentiation, flowering, fruit set and ripening, leaf senescence and seed germination. The effects of cytokinins on plants can be exploited for agricultural and horticultural purposes through either exogenous application of cytokinin or endogenous manipulation of cytokinin metabolism. In *Hatiora gaetneri* for example, flower bud number can be more than doubled in response to a spray application of synthetic cytokinins (Boyle, 1995). The efficacy of exogenous spray applications is limited however, because flowers and leaves do not readily absorb cytokinins and movement of cytokinins within the plant is limited.

Alternatively, it has been reported that endogenous levels of cytokinins can be modified by integrating the ipt gene into the plant genome. The ipt gene encodes the enzyme isopentenyl transferase, which catalyzes the rate-limiting step in cytokinin biosynthesis. A number of promoters, including those inducible by heat, wounding, or light, have been used to drive ipt gene expression. Unfortunately, most of the resulting ipt transgenic plants exhibit morphological abnormalities since overproduction of cytokinins interferes with so many developmental processes (Gan and Amasino, 1997).

Transgenic plants that overproduce cytokinins tend to show reduced stature, release of apical dominance, changes in vascular development, and in some cases, inhibited root growth (Ainley, et al., 1993) In one study, Li, et al. (1992) fused the ipt gene to the auxin-inducible SAUR promoter. This promoter is primarily active in elongating tissue and SAUR-ipt plants expressed elevated levels of cytokinins in these tissues. SAUR-ipt plants displayed reduced stature, increased axillary bud development, reduced root initiation and growth, and exhibited complex and variable changes in senescence.

DEFICIENCIES IN THE ART

Commercially attractive plants are an economic asset for florists and businesses related to horticulture. Plants that produce abundant foliage and flowers without use of expensive external application of chemical agents would have economic benefits by decreasing labor and materials costs. Currently, some phenotypic traits such as cytokinin-controlled bud and leaf development are managed by application of relatively expensive chemicals, adding significantly to the cost of large growers' operations. There is a need for producing desirable plant phenotypes without excessive labor costs and in a controlled manner.

In ornamental horticulture, a significant proportion of all chemical growth regulators applied by growers are used to enhance plant form and aesthetic appearance; e.g., 78% of the 41,305 pounds (active ingredient) of chemical regulators were applied to greenhouse and nursery crops in the U.S. in 1993 were used to enhance aesthetic appearance. This adds not only to expense but also to environmental concerns of exposure to chemicals with possible hormonal effects. There is a need to develop plants that develop the desired phenotypes without need to apply external agents.

Most phenotypic characteristics in plants are developed by controlled crosses, which may or may not result in commercially desirable traits. Such crosses when successful in producing a desirable phenotype may result in sterile hybrids and incur high costs because of time and manpower required for development. Thus transgenic plants exhibiting desirable phenotypes and which can be readily propagated true to type would be desirable for commercial and economic reasons.

SUMMARY OF THE INVENTION

The present invention provides methods that address several deficiencies in certain types of commercial horticultural crops by providing transgenic plants with highly desirable phenotypes. The methods take advantage of the normal endogenous controls for development in the wild-type plant. It has been shown that a plant transformed with the described expression vector is capable of altering the normal ratio of auxin to cytokinin in the plant when endogenous stimuli are generated in the plant. Expression of the transgene results in predictable phenomic response, typically observed as increased branching in the vegetative shoot and increased bud count in the generative shoot compared with the non-transgenic plant.

Cytokinins play important roles in regulating plant growth and development. In developing the present invention, the gene coding for isopentenyl transferase (ipt) was placed under the control of a 0.918 kb fragment, including the 97 bp of 5' UTR leader sequence plus the 821 bp of the untranscribed sequence, of the ACC oxidase gene promoter from *Lycopersicon esculentum* (LEACO1) and introduced into *Nicotiana tabacum* (cv. Havana), *Dendranthema×grandiflo-* rum (cv. Iridon), *Euphorbia pulcherrima* (cvs Red Success and Winter Rose Dark Red), and Creeping Bentgrass (*Agrostis palustris*).

$T_1$ generation LEACO1$_{0.821\ kb}$-ipt tobacco lines displayed a range of growth habits from plants that appeared similar to the wild type in overall stature and branching habit but produced a greater number of flower buds (lines N2 and N8) to plant lines that expressed shoot characteristics typical of constitutive cytokinin expression (lines N1 and N4). For plants at one end of the phenology spectrum, transgenic tobacco plants displayed a dramatic increase in the number of flower buds compared to non-transgenic plants. This phenotype was often observed on plants with an otherwise normal growth habit. The phenotypes associated with LEACO1$_{0.821\ kb}$-ipt transgenic chrysanthemum plants were even more varied; e.g., in one study, non-transgenic chrysanthemums averaged 2.67 laterals per plant following a mechanical pinch. In comparison, the average number of laterals per plant in 29 individual LEACO1$_{0.821\ kb}$-ipt lines covered a continuous range from 2.17 to 9.17 laterals per plant. The average number of flower buds per plant for the 29 transgenic lines ranged from 16.8 to 154.7 compared to 15.5 for the non-transgenic wild-type plant as shown by the data provided herein. This range allows transgenic lines to be selected to meet any aesthetic or production goal, from a modest increase in flower bud and branch number to a dramatic increase in flower bud and branch number.

Plants at one end of the phenology spectrum were characterized by increased lateral branch development, shorter internodes, and fewer buds on the main stem. Isolated leaves of transgenic tobacco plants showed a significantly prolonged retention of chlorophyll under dark incubation (25° C. for 20 days). Leaves of non-transformed plants senesced gradually under the same conditions.

Analysis of ipt expression indicated a marked increase in gene expression in transgenic tobacco. Experiments with LEACO1$_{0.821\ kb}$-gus transgenic tobacco plants suggested auxin and ethylene involvement in induction of LEACO1$_{0.821\ kb}$ promoter activity. The LEACO1$_{0.821\ kb}$-ipt fusion gene has potential utility for improving certain ornamental and agricultural crop species by increasing flower bud initiation and altering branching habit.

Many crops are expected to benefit from the effects observed with transformations using gene constructs such as the ipt chimera disclosed. Almost all ornamental plants are considered more aesthetically pleasing when they display a compact, well-branched phenotype with lots of flowers. Field grown grain crops are also expected to be enhanced because an increase in the number of flowers, fruits or seeds produced per plant represents increased productivity.

The present invention provides an isolated polynucleotide comprising a nucleic acid that encodes an isopentenyltransferase (IPT) and a nucleic acid encoding a heterologous promoter. The encoding nucleic acid is a fusion of the IPT gene and the promoter gene, preferably in a construct where both genes are in an open reading frame such that when IPT polypeptide is expressed in a plant, stimulation of one or more plant cytokinins occurs.

The IPT gene, ipt, employed will be an entire gene, such as a bacterial gene, preferably from *Agrobacterium tumefaciens*. Of course due to the degeneracy of the genetic code, there are numerous replacement codons that will provide a particular amino acid and thus many substitutions can be made in a coding region without changing the primary structure of the encoded polypeptide. Additionally, it is contemplated that one may "plantize" ipt codons; i.e., substitute preferred amino acid codons in order to optimize expression for a particular plant species. Certain other substitutions in the coding region may also be made, such as those that substitute like amino acids; e.g., replacing one neutral amino acid codon with another neutral amino acid codon.

Likewise, mutant ipt or truncated ipt genes are also useful, so long as the chimeric fusion with a heterologous promoter gene is capable of being transferred into a plant cell and the encoded IPT expressed in the plant.

The ipt gene need not have a sequence identical to the bacterial ipt employed to illustrate the invention. So long as substantially similar activity is present and the construct is capable of stimulating endogenous cytokinin production in a transformed plant, the ipt nucleic acid sequence can be 80%, 90%, 91%, 92%, 93%, 94%, 95%, 96%, 97%, 97%, or 99% identical to the exemplary ipt.

An important aspect of the invention is the heterologous promoter employed to construct the fusion gene. For illustration, the LEACO$_{0.821\ kb}$ promoter fragment from the LEACO1 gene was fused to ipt gene. This gene is found in tomato plants, but homologs can be found in other plants, including melon, pea, and petunia. The leaco-1 gene codes for the amino cyclopropane carboxylic acid (ACC) oxidase (ACO) system and acts to convert ACC into ethylene. The several ACO genes cloned from a number of plant species are known and include leaco-1, leaco-2, leaco-3 from tomato, ps-ACO-1 from pea, ACO1, 3 and 4 from petunia and several from melon. In the present invention, the promoter from Leaco-1 gene (SEQ ID NO: 9) can readily be replaced with similar promoters from the above mentioned leaco genes in other plants, or by heterologous promoters with identities of 75, 76, 77, 78, 79, 80, 81, 82, 83, 84, 85, 86, 87, 88, 89, 90, 91, 92, 93, 94, 95, 96, 97, 98, or 99% so long as expression of the chimera in a selected plant is capable of stimulating cytokinin production.

The invention also comprises expression vectors harboring the chimeric genes constructed from an IPT-encoding nucleic acid, e.g. SEQ ID NO:5, and a heterologous promoter such as an ACO promoter. Particular examples of promoters are those encoded by the nucleic acid sequences of SEQ ID NO: 6 and SEQ ID NO:7. The ipt gene would be expected to have similar effect at identities of at least 80-90% of SEQ ID NO:5.

In other aspects of the invention, a host plant cell comprising the described expression vectors is contemplated, including transgenic plants propagated from such plant cells. Plants from which cells may be obtained or used for transformations include tobacco, chrysanthemum, petunia, tomato, melon, pea, poinsettia, rose, canola, flowering tobacco, watermelon and bent-grass; as well as the related species that are included in the respective plant families.

In particular embodiments, the invention also includes an isolated nucleic acid sequence comprising the nucleic acid sequence selected from the group consisting of SEQ ID NO: 6-7 in open reading frame with a nucleic acid encoding a heterologous isopentenyl transferase (IPT).

Another embodiment is an isolated nucleic acid sequence encoding isopentenyl transferase (IPT) fused 5' with an ACO promoter capable of expressing the IPT in a plant. More particularly, the nucleic acid sequence is SEQ ID NO:5 fused with a nucleic acid having the sequence of SEQ ID NO: 6 (LEACO1$_{0.821\ kb}$ promoter plus the 97 bp UTR leader sequence) or SEQ ID NO:7.

Transgenic plants transformed with the disclosed LEACO1$_{0.821\ kb}$-ipt constructs are a particularly important aspect of the invention. These transformed plants exhibit significantly increased branching and flower bud numbers compared to the untransformed plants of the same species. Particularly significant results have been demonstrated with chrysanthemum and flowering tobacco and are expected to be similar in several horticulturally important plants, including poinsettia, tomato and creeping bent-grass and in agriculture plants that are used for canola oil production. Other plants include tobacco, chrysanthemum, petunia, tomato, melon, pea, poinsettia, rose, canola, flowering tobacco, and watermelon, as well as related species. Exemplary families include the Cruciferae, Cucubitaceae, Compositae, Solanaceae, Euphorbiaceae, Gramineae, Leguminosae, and Rosaceae. In the Rosaceae there are over 3200 species with many important horticultural species such as plums, peaches, cherries, apricots and almonds in the genus *Prunus*. In the Compositae, there are over 20,000 species including many of the most popular ornamental species such as chyrsanthemum, asters, sunflower, marigold and the like. The Gramineae family includes many of the world's most important grain crops including rice, wheat, oats, barley, rye, and maize. It also includes sugar cane, important structural species such as bamboo, forages used for animal feeds and many important ornamental and turf species.

The invention also includes progeny of the described transgenic plants and seeds from these plants. The progeny show the same enhanced phenotypic traits as the parent. DNA analysis shows that one or more copies of the transgene can be incorporated into plant genome. Depending on the position of incorporation, the phenotypes; e.g., increased bud number and leaf branching, may vary in different plants transformed with the same expression vector; however, it is believed that vegetative propagation of a plant with highly desirable phenotype will result in substantially identical clones, allowing elimination of plants that do not have marketable appearance or productivity.

Related aspects of the invention include methods for increasing endogenous cytokinin levels in a plant, comprising transforming a plant with a transgene comprising an isopentenyltransferase (IPT)-encoding nucleic acid fused with an aminocyclopropane carboxylic acid oxidase promoter (ACO)-encoding nucleic acid. Expression of the transgene in the plant causes increased cytokinin levels in the transformed compared with a non-transformed plant of the same species. The increased cytokinin levels modify selected phenotypic traits in the maturing transgenic plant and particularly affect readily detectable changes such as time of senescence, increased lateral branch development and increased flower bud development (e.g. more buds initiated) when compared with untransformed plants of the same species. Particularly suitable plants for transformation include tobacco, chrysanthemum, petunia, tomato, melon, pea, poinsettia, rose, canola, flowering tobacco, watermelon and bent-grass, as well as related species.

Preferred ACO promoters for use in constructing the described chimeric genes include leaco1, leaco2 and leaco3, such as promoters having the nucleic acid sequence of SEQ ID NO. 6, SEQ ID NO:7 or SEQ ID NO: 12.

The methods described for the transgenic plants of the invention will have increased levels of cytokinins where endogenous production of these cytokinins can be affected by expression of the isopentenyltransferase gene under control of an ACC oxidase gene promoter fragment. Accordingly, expression of the IPT gene will be responsive to increased levels of the auxin indoleacetic acid or ethylene pathway activity in a transformed plant.

Overall and in general therefore, the invention includes expression vectors comprising any of the described fusion polypolypeptides encoded by a chimeric gene constructed from an ipt gene and an ACO promoter sequence. Also included are host plant cells and transgenic plants harboring the disclosed expression vectors.

For commercial purposes, and of use to growers who may wish to further develop plants in the manner disclosed, a packaged kit is contemplated. Such a kit may include a $LEACO1_{0.821\ kb}$-ipt chimera comprised within a suitable transfection plasmid and directions for use of the plasmid suitable for various plant species.

BRIEF DESCRIPTION OF THE FIGURES

FIG. 13. LEACO1$_{0.821\ kb}$-ipt tobacco lines displayed morphological traits that were characterized into two distinct phenomic groups. LEACO1$_{0.821\ kb}$-ipt plants in the first group, including lines N2 and N8, displayed a relatively normal shoot morphology but with an increased number of flower buds (A) relative to the wild-type line (B). LEACO1$_{0.821\ kb}$-ipt plants in the second group, including lines N1 and N4, displayed short internodes, increased lateral branching and poor root development (D) compared to the wild type (C).

FIG. 15. Growth characteristics and cytokinin concentrations in leaco1$_{-0.821\ kb}$-ipt chrysanthemum lines. (top left) Vegetative branching habit of wild-type and leaco1$_{-0.821\ kb}$-ipt chrysanthemum. The leaco1$_{-0.821\ kb}$-ipt lines produced a highly branched, compact growth form that is most aesthetically desirable for ornamental plants. (top right) Example of the range of flowering responses for three leaco1$_{-0.821\ kb}$-ipt chrysanthemum lines (foreground) compared to the wild-type (background). The dramatic increase in branching and flower bud number associated with the leaco1$_{-0.821\ kb}$-ipt plants. (Bottom left) Root growth of leaco1$_{-0.0821\ kb}$-ipt plants was unaffected by expression of the leaco1$_{-0.821\ kb}$-ipt gene. (Bottom right) Cytokinin concentrations in the leaco1$_{-0.821\ kb}$-ipt transgenic lines reflected the dramatic changes in phenotype observed in this study. Transgenic plants with more branching in the vegetative stage (N1 & N14) showed either a higher active cytokinin pool or evidence of increased cytokinin cycling (increase storage and deactivated pools). Line number 5 appeared similar to the wild-type in the vegetative stage but produced dramatically more buds in the reproductive mode (and a corresponding big increase all cytokinin pools.

Figure 1:
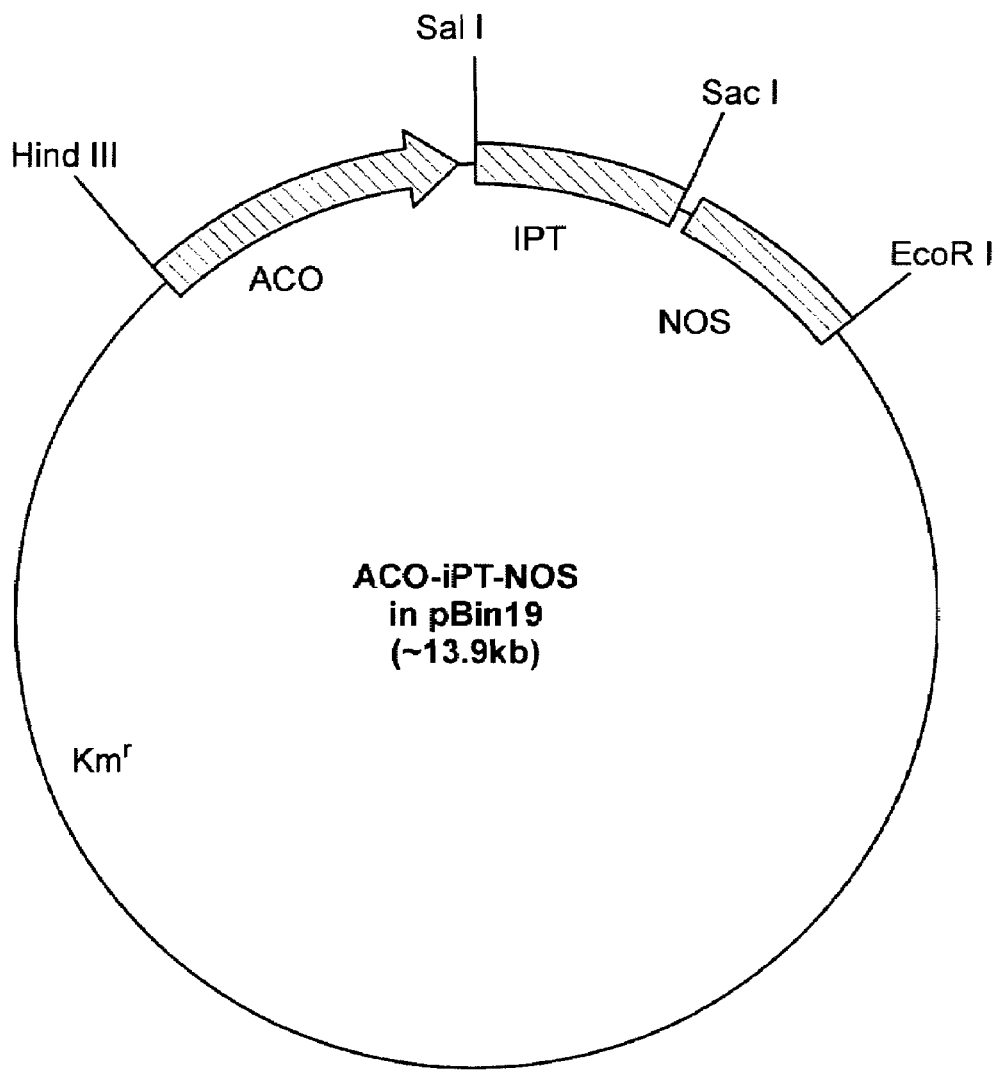
FIG. 1. Chimeric ACO-IPT construct in pBin binary vector
Figure 2:
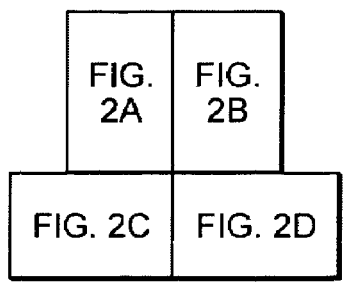
FIG. 2. Biosynthetic pathway for ethylene biosynthesis.
Figure 2A:
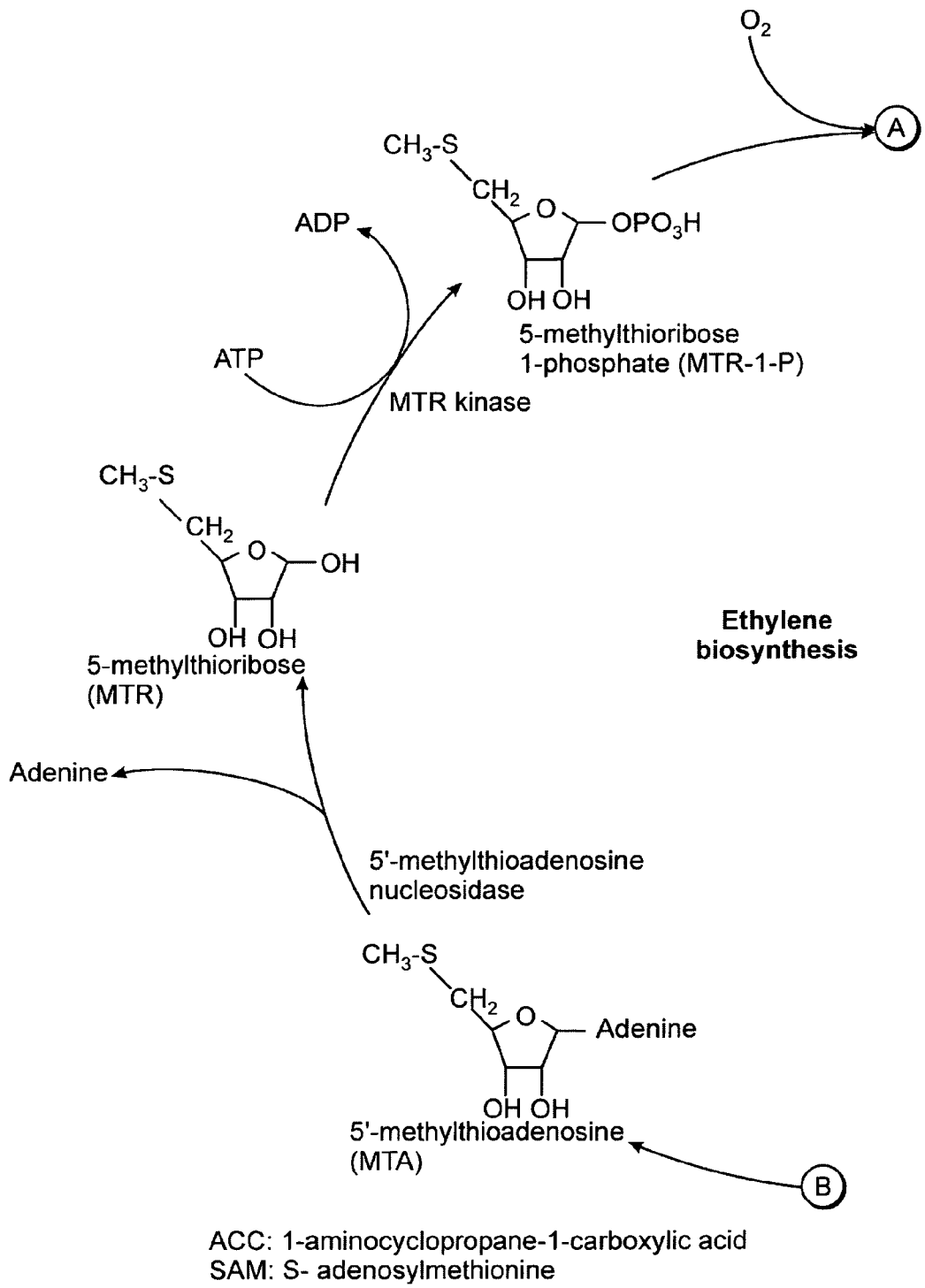
Figure 2B:
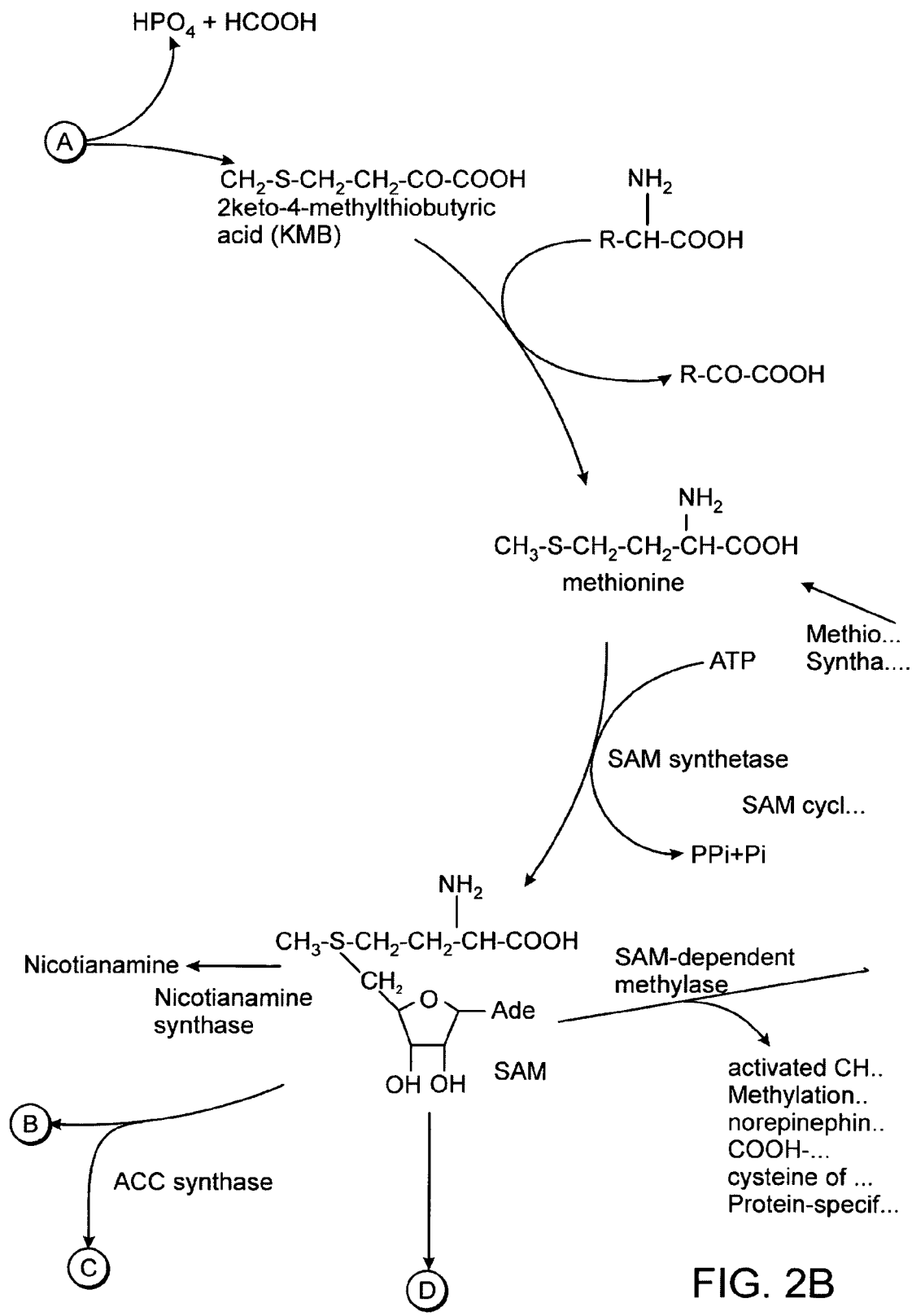
Figure 2C:
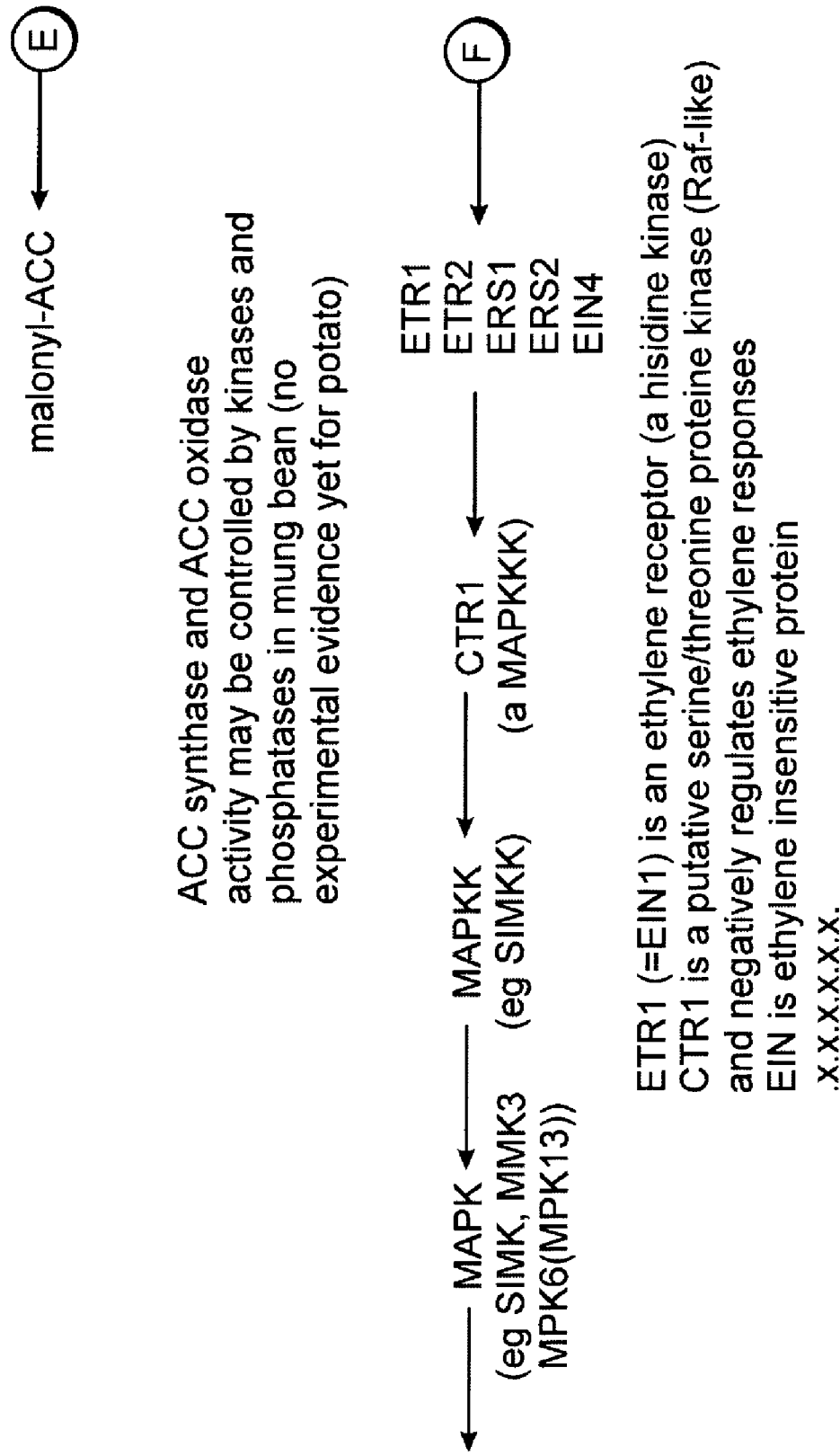
Figure 2D:
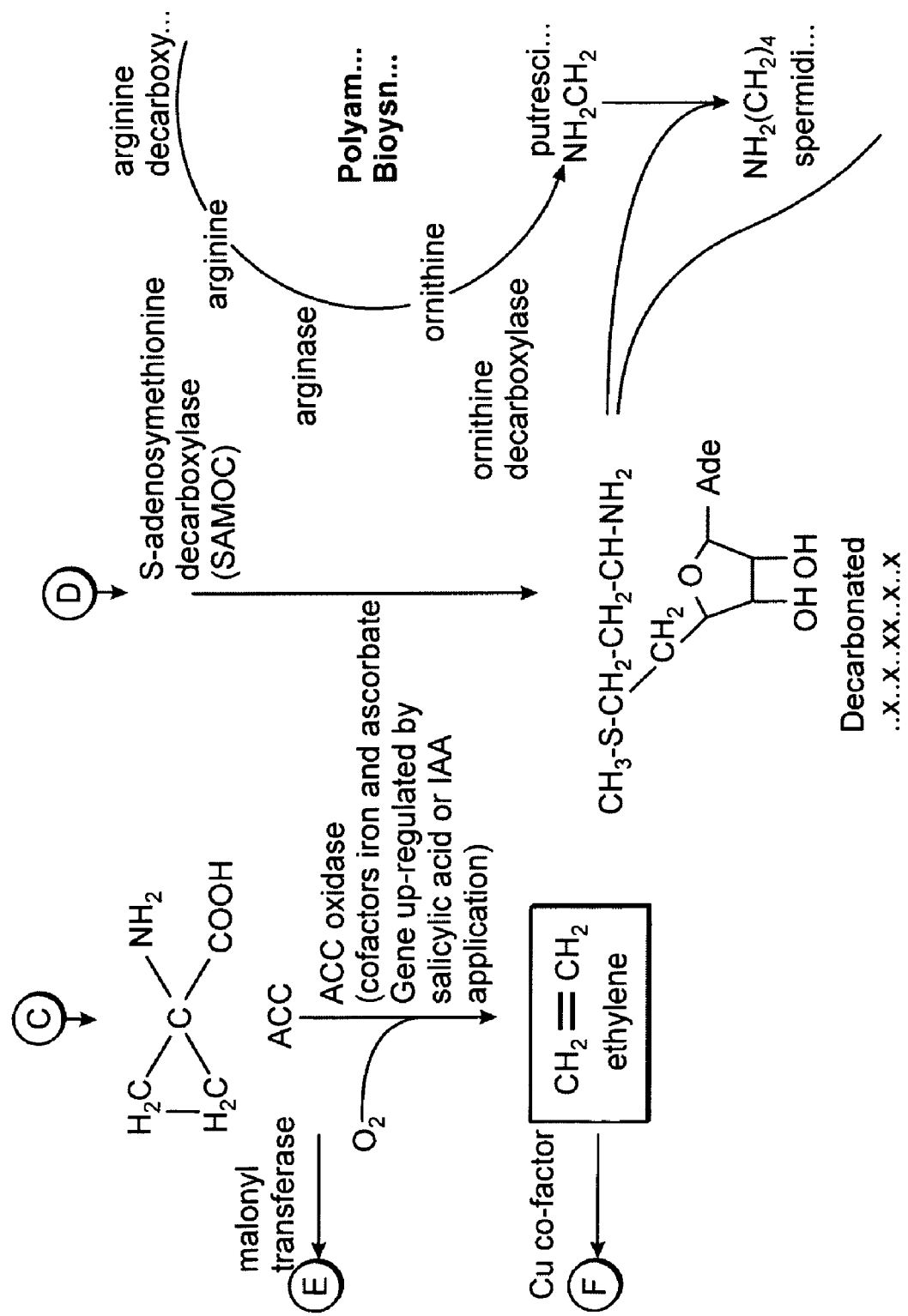
Figure 3:
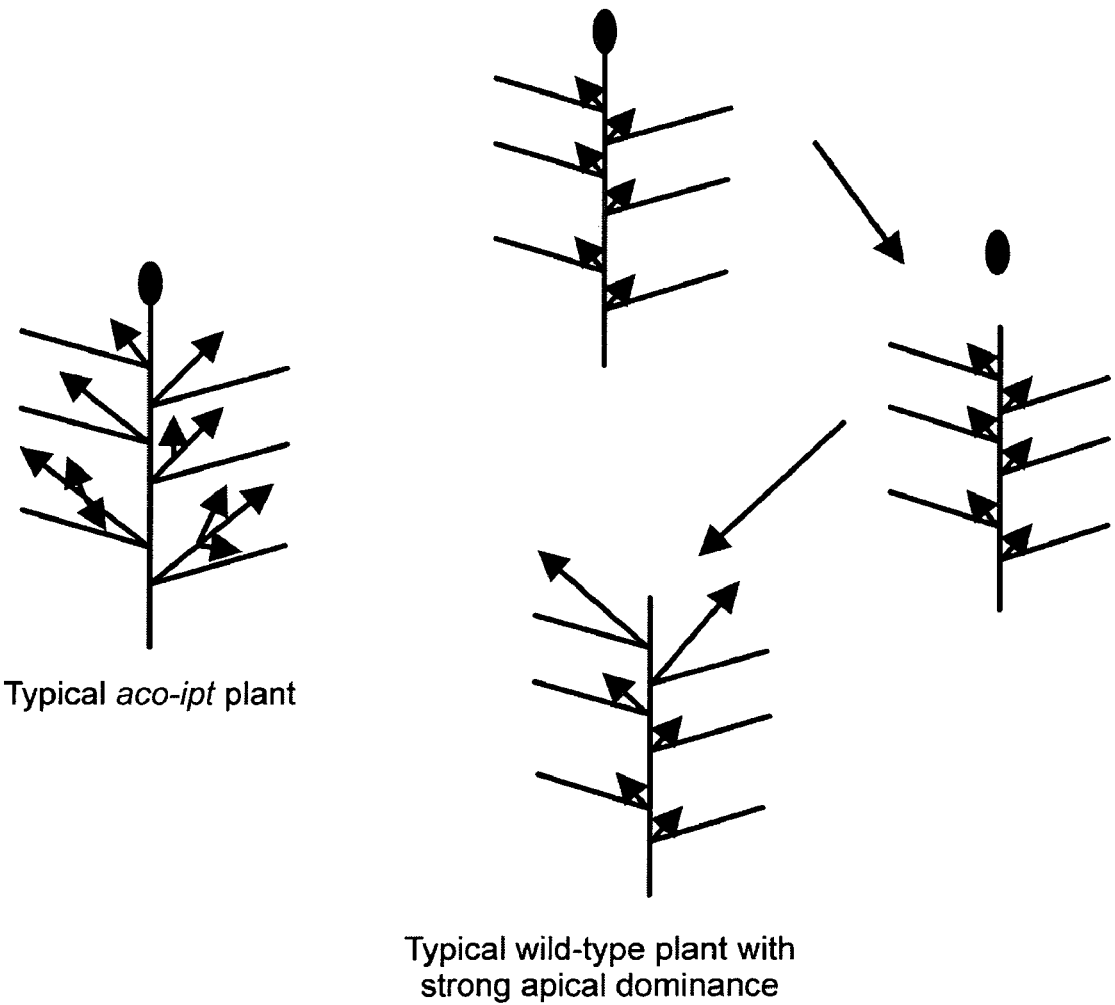
FIG. 3. Schematic diagram of typical phenotype for species with strong apical dominance shows elongation of lateral buds after removal (pinching) of apical buds in comparison with a $LEACO1_{0.821\ kb}$-ipt transgenic line from the same species. The $LEACO1_{0.821\ kb}$-ipt line exhibits increased lateral branch and bud development in the absence of apical bud removal.

A: Scheme showing the structure of the LEACO1$_{0.821\ kb}$-ipt-nos construct. From left to right: RB—right border of pBin19; P-nos nopaline synthase promoter; NPTII—neomycin phosphotransferase (nptII) gene from Tn5; T-nos—nopaline synthase terminator; LEACO1$_{0.821\ kb}$ fragment of LEACO1 promoter from tomato; U—0.97 kb 5' UTR sequence; IPT—ipt gene from *Agrobacterium tumefaciens*; LB—left border of pBin19 vector.

B: Scheme showing location of stress-responsive short motifs, TGTCTC (SEQ ID NO: 13)/GAGACA (SEQ ID NO: 14)-elements and G-box motifs in 0.821 kb fragment of LEACO1 promoter from *Lycopersicon esculentum*. Used LEACO1 promoter's fragment contained part of LTR element (between nucleotides −821 to −590 upstream from the coding start site), two 10 bp TCA motifs (↓) and an 8 bp ethylene responsive element (■). Single copies of the consensus AuxRE TGTCTC (SEQ ID NO: 13)- and the inverse AGAACA-sequences are located at −776 and −592, respectively (!). In forward orientation the TGTCTC (SEQ ID NO: 13) element (with one substitution TGTCTt (SEQ ID NO: 15)) appears at −187, −666, and −688 (✦). The G-box motif CACGTG (with one substitution CtCGTG (SEQ ID NO: 16))

appears at −552 and −656 (↕). G-box core ACGT (SEQ ID NO: 17) elements were found at −483, −703 and −726(↕).

FIG. 18. Poinsettia Transformation Protocol: (top left) Stem internode explants were inoculated with *Agrobacterium* carrying the transgene of interest. TDZ was used to induce callus, which then gave rise to shoot initials. Transgenic tissue was selected using kanamycin & transgenic shoots gradually develop from the transgenic calli (top right). Leaf from 'Red Success' plant transformed with 35s-gus gene (bottom). The blue colored-stain is a visual indicator of GUS activity in gus transgenic tissue.

FIG. 19 depicts SEQ ID NO:1.
FIG. 20 depicts SEQ ID NO:2.
FIG. 21 depicts SEQ ID NO:3.
FIG. 22 depicts SEQ ID NO:4.
FIG. 23 depicts SEQ ID NO:5.
FIG. 24 depicts SEQ ID NO:6.
FIG. 25 depicts SEQ ID NO:7.
FIG. 26 depicts SEQ ID NO:8.
FIG. 27 depicts SEQ ID NO:9.
FIG. 28 depicts SEQ ID NO:10.
FIG. 29 depicts SEQ ID NO:11.
FIG. 30. depicts SEQ ID NOS:12, 13-17, 11, 18-19 & 10, respectively in order of appearance.

FIG. 31 depicts SEQ ID NO:13, the sequence required for auxin responsive elements (AuxRE) in genes regulated by the auxin response factors. The sequence is shown in the forward orientation.

FIG. 32 depicts SEQ ID NO:14, the sequence required for auxin responsive elements (AuxRE) in genes regulated by the auxin response factors. The sequence is shown in the inverse orientation.

FIG. 33 depicts SEQ ID NO:15, the sequence required for auxin responsive elements (AuxRE) found in genes regulated by auxin response factors. The sequences are shown in the forward orientation with one substitution in position six (substituted bases in lower case letters).

FIG. 34 depicts SEQ ID NO:16, the sequence of the G-box motif, a regulatory element found in many genes including auxin responsive genes. The sequence is show in the forward orientation with one substitution in position two (substituted bases in lower case letters).

FIG. 35 depicts SEQ ID NO:17, the sequence of the G-box motif core elements. The sequence is shown in the forward orientation.

DETAILED DESCRIPTION OF THE INVENTION

The present invention provides nucleic acids, vectors and expression cassettes that are capable of modifying cytokinin production in a plant, thus enhancing certain desirable phenotypic characteristics such as increased bud number and/or branching without causing the negative effect on root growth associated with constitutive IPT expression. The novel constructs are designed to express the ipt gene product, isopentenyltransferase (IPT), under conditions that induce a transformed plant to express an endogenous plant cytokinin when the leaco1$_{-0.821\ kb}$ fragment of the LEACO1 gene promoter, fused to the ipt gene, is activated. This is accomplished by engineering a chimera, comprising at least one leaco gene promoter, or other ethylene responsive promoter, fused to an isopentenyltransferase (IPT)-encoding DNA. When plant cells are transformed with an expression vector harboring the chimeric gene, activation of the LEACO1 promoter causes upregulation of the IPT gene producing expression of the isopentenyltransferase enzyme and increased production of endogenous cytokinin in the affected plant tissue. In the present work a 821 bp fragment of leaco1 gene was selected which contained only a portion of the LTR-like element but two copies of the TCA motif and one of the 8 bp 5'-AA/TTTCAAA-3' (SEQ ID NO:10) ethylene responsive element. In addition, the promoter fragment used in our study contained multiple copies of the auxin responsive element (AuxRE) required TGTCTC-sequence (SEQ ID NO: 13) (or the inverse GAGACA-sequence (SEQ ID NO: 14), or the TGTCTt sequence (SEQ ID NO: 15) with one substitution in position six [substituted bases in lower case]) found in genes regulated by auxin response factors (Ulmasov et al. 1995). The 821 bp leaco1-fragment also contains the G-box motif (CtCGTG G-Box motif (SEQ ID NO: 16) with one substitution in the two position) and multiple copies of the ACGT G-box core element (SEQ ID NO: 17) (Guilfoyle et al. 1998; Hong et al. 1995). G-box motifs are regulatory elements found in many genes including auxin responsive genes such as GmAux28 (Hong et al. 1995). A common feature of genes in the auxin/IAA family, are regions containing multiple putative AuxREs (Remington et al. 2004). The objectives were to characterize the in situ phenotypic response of transgenic chrysanthemum and tobacco lines expressing IPT under the control of an ethylene/auxin-responsive $_{0.821}$ kb fragment of the LEACO1 promoter in the absence of an exogenous ethylene signal, and to test relative changes in LEACO1$_{0.821\ kb}$ promoter activity in response to various auxin and ethylene promoting and inhibiting agents.

Cytokinin stimulates cell division and expansion, affects lateral branch development and bud initiation, and delays whole plant senescence, post-harvest leaf deterioration, low temperature induced leaf yellowing and maintains vigor in many crop plants.

Expression of the chimeric ipt (isopentenyl transferase) gene results in the production of cytokinins. IPT is an enzyme that catalyzes the rate-limiting step in cytokinin biosynthesis. Cytokinins are phytohormones with broad effects on plant growth and development, including delayed senescence and increased branching and flower bud counts. In LEACO1$_{0.821\ kb}$-ipt chrysanthemum, increased cytokinin concentrations were closely correlated with increased branching in vegetative plants and increased flower bud counts in flowering plants. Additionally, cytokinins interact with other plant hormones such as auxins to influence lateral branch development and flower bud number. High cytokinin concentrations can also affect ethylene biosynthetic pathway activity. When the disclosed ipt gene construct is employed in accordance with the invention, the interplay of the hormones auxin and cytokinin is fairly complex in that it is mediated through the activity of the ethylene biosynthetic pathway, in turn controlled by the promoter selected for the construct (LEACO1$_{0.821\ kb}$).

The LEACO1 gene encodes the ACC oxidase enzyme in *Lycopersicon esculentum*. ACC oxidase catalyzes the conversion of 1-aminocyclopropane-1-carboxylic acid (ACC) to ethylene, the last step in the biosynthesis of this plant hormone. ACC is synthesized from S-adenosylmethionine (SAM) by the enzyme ACC synthase. Blume and Grierson (1997) reported that the ACC oxidase promoter from tomato (LEACO1) is active in response to aging, wounding, ethylene, pathogen infection and treatment with methyl jasmonate and α-amino butyric acid. The LEACO1gene is inducible in a number of organs at various stages of the plant life cycle. In addition, the ACC oxidase transcripts are reported to be spatially regulated throughout flower development (Barry, et al., 1996), and LEACO1 promoter activity detected in leaves and flowers and can be induced by external factors that stimulate ethylene pathway activity such as wounding, exogenous ethylene or pathogen infection. Khodakovskaya et al (2006) discovered that LEACO1$_{0.821\ kb}$ promoter activity increased in response to auxin and was deactivated by the auxin inhibitor TIBA.

Blume and Grierson (1997) reported that 396 bp and 1825 bp fragments in the LEACO1 promoter were sufficient to drive strong gus gene expression during both leaf and flower senescence, but that a 124 bp fragment was less effective. Based on these responses, they concluded that the essential cis-acting elements are located in the region between −396 and −124 upstream of the transcription start site. However, the 1825 bp sequence contained a repetitive element found in the tomato genome that resembles the long terminal repeats (LTRs) of copia-like retrotransposons while the 396 bp sequence did not include this element. Blume and Grierson (1997) did not test promoter response to auxin.

Further, sequences with high homology (70-75%) to the 5' flanking sequences of the ACC oxidase genes (PHACO1, PHACO3 and PHACO4) are located within 500 bp of the transcription start site. At least two different stress-responsive short motifs were present in the 1825 bp fragment but not in the 396 bp fragment. For instance, Blume and Grierson (1997) report the 10 bp TCA motif (5'-TCATCTTCTT-3') (SEQ ID NO:11) occurs seven times (allowing two substitutions) in the LEACO1 promoter between nucleotides −667 and −1447, and an 8 bp element (5'-AA/TTTCAAA-3')(SEQ ID NO:10) is present in three copies between nucleotides −473 and −1662. The TCA motif is present in the 5' upstream region of over 30 stress- and pathogen-inducible genes while the 8 bp element is reportedly necessary for ethylene-response in the carnation GST1 and the tomato E4 gene promoters.

Figure 17:
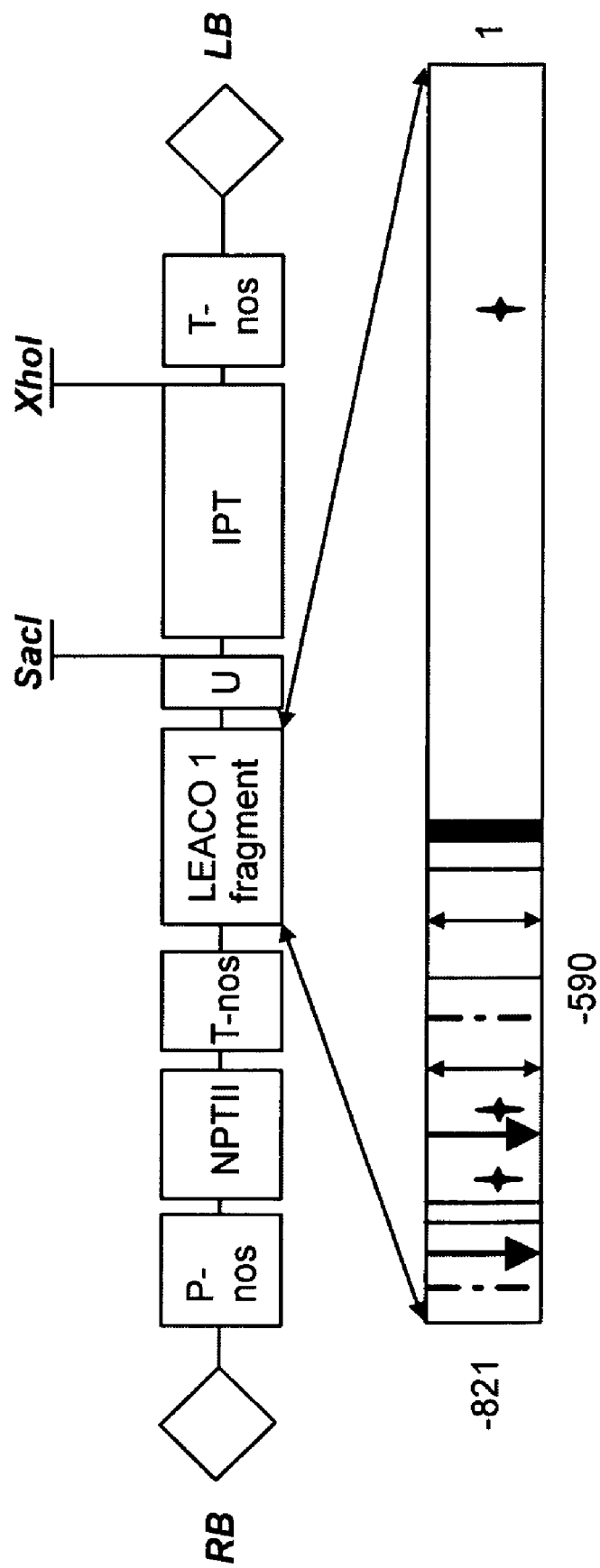
FIG. 17. Structures of used LEACO1$_{0.821\ kb}$-ipt-nos construct (A) and 0.821 kb fragment of the LEACO1 promoter (B).

In addition, the promoter fragment used in our study contained multiple copies of the auxin responsive element (AuxRE) required TGTCTC-(SEQ ID NO: 13) (or inverse GAGACA-(SEQ ID NO: 14)) sequence found in genes regulated by auxin response factors (Ulmasov et al. 1995) and G-box motifs, which are regulatory elements found in many genes including auxin responsive genes such as GmAux28 (Hong et al. 1995). In the LEACO1 gene promoter fragment used in our study, we identified single copies of the TGTCTC (SEQ ID NO: 13), and inverse GAGACA (SEQ ID NO: 14), sequences in reverse orientation as well as three copies of the sequence TGTCTC motif with one substitution in position six (TGTCTt (SEQ ID NO: 15)) in forward orientation (substituted bases in lower case). In addition, we identified two copies of the CACGTG G-Box motif with one substitution (CtCGTG (SEQ ID NO: 16)) and three copies of the ACGT (SEQ ID NO: 17) G-box core element. (FIG. 17).

The invention has been illustrated with LEACO1$_{0.821\ kb}$-ipt gene; however, as one of skill in the art will appreciate, the described construct is expected to provide similar effects using related and highly homologous ipt promoters. A sequence search of the GeneBank (Blast) for homology to the LEACO1$_{0.821\ kb}$ promoter reveals homology for several genes described many years ago, although these genes were not named because the functions were unknown. The original LEACO1 gene may be included in this group and its function described at a later time.

Homology exists in some of the ethylene responsive elements contained in the promoter fragment employed in the examples described herein (LEACO1$_{0.821\ kb}$). The RPT (two repeat) region between −1722 and −590 contains homology to the ethylene responsive promoters of the 2A11 and E4 genes. Additionally, the TCA motif is known to be present in many stress- and pathogen-responsive genes, as well as ethylene-responsive elements (ERE) found in carnation GST1 and tomato E4 gene. The fragment used in the present examples also contains a portion of a repetitive element found in the tomato genome that resembles the long terminal repeats (LTRs) of copia-like retrotransposons found in other genes. Further, sequences with high homology (70-75%) to the 5' flanking sequences of the ACC oxidase genes (PHACO1, PHACO3 and PHACO4) are located within 500 bp of the transcription start site. In the present study, a 920 bp fragment was selected that contained only a portion of the LTR-like element but two copies of the TCA motif and one of the 8 bp 5'-AA/TTTCAAA-3' (SEQ ID NO: 10) ethylene responsive element.

The promoter fragment used in our study contained multiple copies of the auxin responsive element (AuxRE) required TGTCTC-(SEQ ID NO: 13) (or inverse GAGACA-(SEQ ID NO: 14)) sequence found in genes regulated by auxin response factors (Ulmasov et al. 1995). TGTCTC (SEQ ID NO: 13)/GAGACA (SEQ ID NO: 14) AuxREs are found in many auxin response genes (Guilfoyle et al. 1998). Composite AuxREs may contain both the TGTCTC (SEQ ID NO: 13) element and a coupling element such as a G-box motif (Guilfoyle et al. 1998; Hong et al. 1995). G-box motifs are regulatory elements found in many genes including auxin responsive genes such as GmAux28 (Hong et al. 1995). A common feature of genes in the auxin/IAA family, are regions containing multiple putative AuxREs (Remington et al. 2004). These putative AuxREs contain motifs with at least five out of six nucleotides matching the consensus TGTCTC (SEQ ID NO: 13) sequence in forward or reverse orientation (Ulmasov et al. 1997; Ulmasov et al. 1999a; Ulmasov et al. 1999b; Remington et al. 2004). Ulmasov et al. (1997, 1999b) reported that the nucleotides TGTC (positions +1 to +4) of the TGTCTC (SEQ ID NO: 13) element are essential for binding auxin response factors, while substitutions at +5 are tolerated, and the importance of position +6 is variable.

Figure 12:
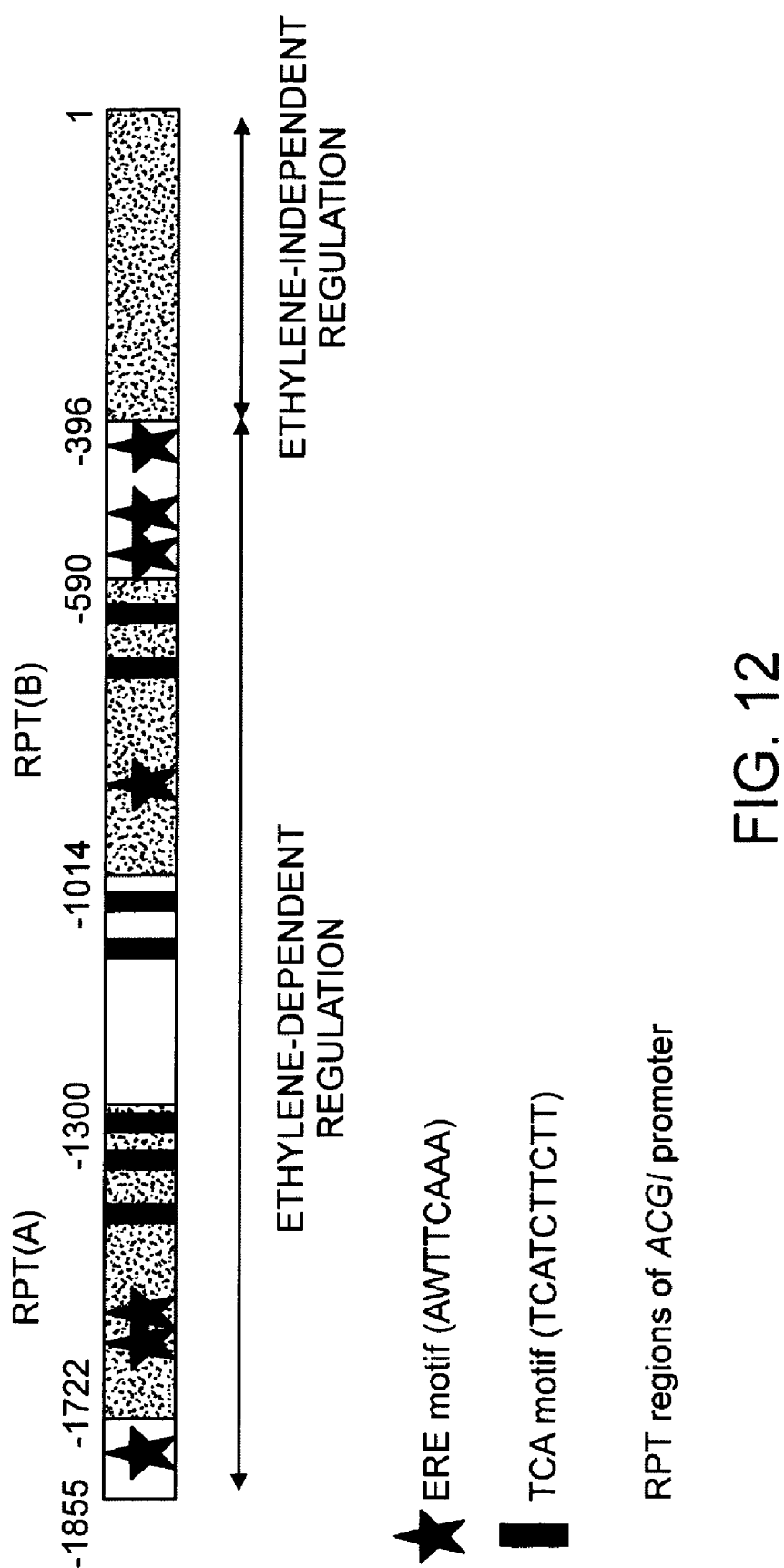
FIG. 12. Structure of the tomato ACO1 promoter. The position of the two repeat regions (RPT) which contains sequences with homology to the ethylene responsive promoters of 2A11 and E4 are shown. The position of the ethylene responsive (ERE) regions and stress related (TCA) motifs are also shown. The −1855 to −396 region of the promoter confers ethylene-dependent expression whereas the −396 region confers ethylene-independent expression of LEACO1$_{0.821\ kb}$-GUS promoter fusions.

The schematic shown in FIG. 12 (Alexander and Grierson. 2002) indicates the location of some of the key ethylene and stress response elements in the LEACO1$_{0.821\ kb}$ promoter. The schematic shown in FIG. 17 indicates the location of some of the key auxin response elements and G-Box regulatory elements in the LEACO1$_{0.821\ kb}$ promoter.

The LEACO1$_{0.821\ kb}$-gus gene was constructed. Gus is a reporter gene that allows visualization of gene expression as a blue-colored stain. This effect was used to test the effects of various hormones, hormone inhibitors, and metabolic precursors on LEACO1$_{0.821\ kb}$ promoter activity (see FIG. 14)

Tobacco, petunia, and chrysanthemum were transformed with the LEACO1$_{0.821\ kb}$-ipt. It is believed that similar transformations in a wide variety of other plants will alter phenotypes in a similar manner; e.g., increased number of flowering meristem (i.e., shoot tips) in poinsettia. A number of crop plants with the ipt gene under the control of other promoters have been transformed, including for example cold-inducible promoter, wound-inducible promoter, and auxin up regulated promoter. Crop species include rose and flowering tobacco (N. alata), canola, watermelon and tomato.

Differences in the number of gene copies in the genome of various transformed lines (FIG. 4) were found in tobacco. While gene number represents one possible explanation for phenotypic differences, a more likely cause is the insertion "position effect" in the genome (the location of the transgene in the chromosome and on which chromosome) that causes differences in the level of the ipt gene expression. Variations in expression level of the IPT gene) appear likely to be a major reason for the phenotypic variations observed. For example, chrysanthemum phenotype was closely correlated with ipt gene expression level, as indicated by mRNA concentration (FIG. 16) and cytokinin concentration in the tissue (Table 1).

Southern blot analysis of genomic DNA isolated from the wild type tobacco and LEACO1$_{0.821\ kb}$-ipt transgenic tobacco lines representing two distinct phenomic groups was performed. The DIG-labeled 0.52 kb fragment of the ipt gene from LEACO1$_{0.821\ kb}$-IPT-NOS plasmid DNA was used as a probe. One or two copies of the ipt gene were detected in lines showing either the highly branched morphology (FIG. 4C, lanes 2 and 3) or the normal shoot phenotype with increased flower bud number (FIG. 4C, lanes 4 and 5). Non-transformed wild type Nicotiana tabacum DNA (FIG. 4C, Lane 1) served as a negative control and the ipt fragment was not detected. Plasmid DNA was used as a positive control (FIG. 4C, Lane 6).

The LEACO1$_{0.821\ kb}$ promoter was used to investigate the effects of ethylene biosynthetic pathway-regulated ipt expression on the morphological development of tobacco and chrysanthemum plants grown in situ in the greenhouse and in controlled environment chambers. LEACO1$_{0.821\ kb}$-ipt transgenic tobacco lines were sorted into two distinct groups based on overall plant growth habit and flower bud initiation (FIG. 13) while transgenic chrysanthemum lines displayed a continuous array of phenotypes from ones that appeared similar to the wild-type in branch and bud number to ones with dramatic increased in both branch and bud numbers (Table 2). In tobacco, the first phenotypic group was characterized by normal shoot morphology but showed a dramatic increase in the number of flower buds (FIG. 13A), in comparison with wild-type bud count in FIG. 13B and plant form, FIG. 13C. RT-PCR revealed low expression in the vegetative plant under glasshouse conditions. In chrysanthemum, all transgenic lines showed horticulturally acceptable shoot morphology but in some lines increases in bud counts and branch number were dramatic while in other lines the changes in bud counts and branch numbers were subtle. As in tobacco, phenotypic differences were associated with a corresponding change in gene expression, as determined by both RT-PCR (FIG. 16) and tissue cytokinin concentrations (Table 1).

In tobacco, the phenotypy of some lines were characterized by a number of dramatic changes in vegetative development but little change in generative development. The lateral shoot tips appeared abnormal and flower buds may have aborted at an early stage of development (FIG. 13D). The phenotype of these plants appeared to be typical of plants that over-express IPT. For instance, the plants in these lines tended to be short with shorter internodes. Lateral shoot development was not inhibited as is typical in tobacco, and root growth was poor. Also, ipt gene expression as determined by RT-PCR analysis, was visibly higher in lines exhibited this phenotype. In addition, transgenic plants that overproduce cytokinins typically display resistance to leaf senescence under stressful conditions. Detached leaves from LEACO1$_{0.821\ kb}$-ipt plants displayed chlorophyll retention characteristics that correlated with the range of ipt expression levels associated with the two phenotypic groups. In contrast, transgenic chrysanthemum never displayed "abnormal' shoot growth, even in lines with the highest expression levels; i.e., exhibiting the most lateral branching and the highest bud counts. Further, root growth appeared normal even in LEACO1$_{0.821\ kb}$-ipt lines that displayed the more dramatic phenotypes (e.g., line N14 see FIG. 14A).

In tobacco, the increase in cytokinin concentrations in flowering LEACO1$_{0.821\ kb}$-ipt line N5 chrysanthemum supports an increase in ipt expression when plants switch from vegetative to generative development. In the N5 chrysanthemums, plants in the vegetative stage produced cytokinin concentrations similar to the wild-type but in the generative state the active cytokinin pool increased over 3-fold, the storage cytokinin pool increased over 4-fold, and the pool of deactivated cytokinin increase 65-fold (Table 1). Under generative growth conditions, a direct increase in ethylene biosynthetic pathway activity, or a change in endogenous IAA concentration that triggered an increase in ethylene pathway activity, would be expected to result in a subsequent increase in expression of the LEACO1$_{0.821\ kb}$-ipt gene. Previous reports indicated that IAA stimulates ethylene production by inducing expression of the ACC oxidase gene. Using the LEACO1$_{0.821\ kb}$-gus gene to assess LEACO1$_{0.821\ kb}$-regulated gene activity, removal of the endogenous auxin source (the shoot apex) inhibited gus gene expression. However, gus gene expression was restored by applying exogenous IAA to the excised shoot tip (FIG. 14).

Figure 14A:
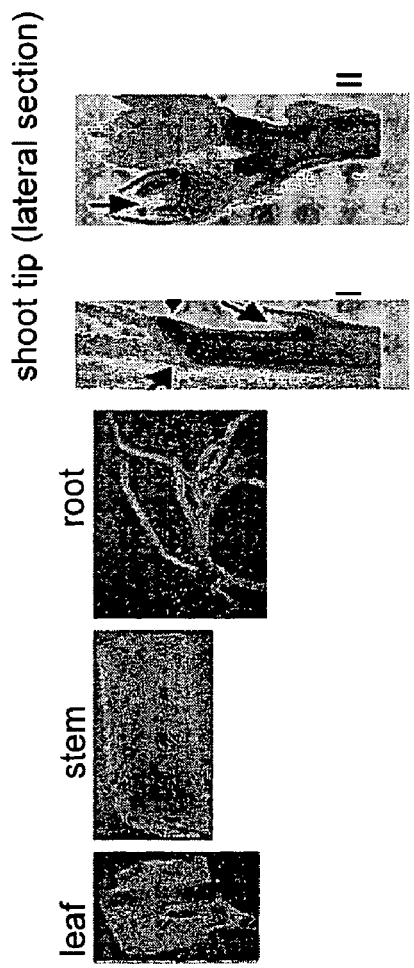
FIG. 14A-D. Tobacco seedlings transformed with the LEACO1$_{0.821\ kb}$-gus reporter gene. The blue color indicates increased expression of the LEACO1$_{0.821\ kb}$-gus gene and reduced blue color indicates a reduction in gene expression. A: gus expression in young leaf, stem and root of a LEACO1$_{0.821\ kb}$-gus transgenic seedlings (left). gus expression viewed in longitudinally sectioned shoot tips from LEACO1$_{0.821\ kb}$-gus transgenic plants (right). Note that the strongest gus expression (indicated by arrows) is found in the apical and lateral meristems in vegetative shoots (I) and surrounding the developing flower bud and in lateral meristems in generative shoots (II); B, C & D: gus-response of transgenic LEACO1$_{0.821\ kb}$-gus plants following exposure to IAA, ethephon, the IAA transport inhibitor TIBA, the biosynthetic precursor of ethylene ACC, or the ethylene biosynthesis inhibitor AOA in plants N5 and N3 with the shoot apex either intact (I) or removed (II). In the initial experiment, (B) IAA and TIBA applied in a lanolin paste, but AOA was applied in solution using a paintbrush to spread a thin film over the stem surface. IAA was applied to the shoot apex and TIBA was applied as a ring on the stem just below the shoot apex. In the following experiment (C & D), ACC, AOA, and ethephon were applied as sprays but TIBA was again applied in a lanolin paste.
Figure 14B:
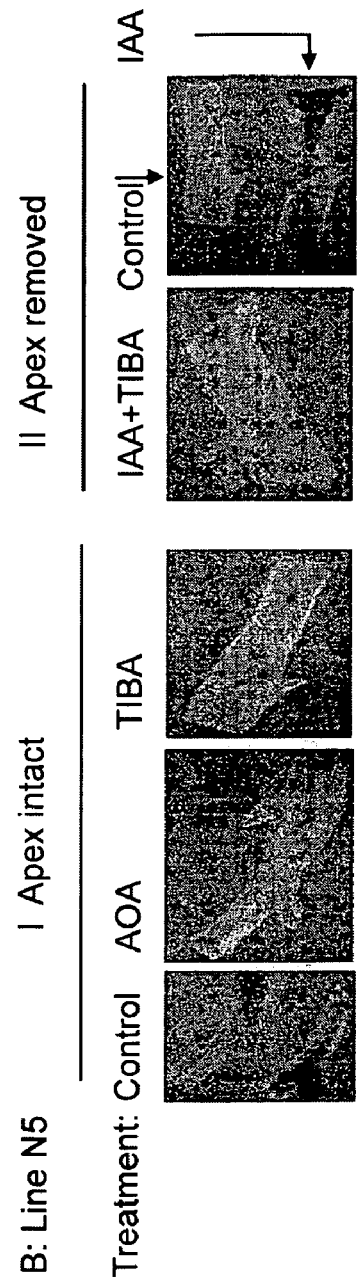
Figure 14C:
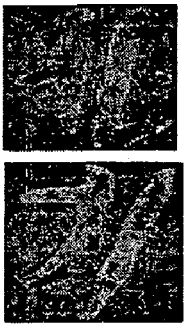
Figure 14D:

In shoots with the apex intact, the auxin transport inhibitor TIBA suppressed gus expression. Shoots with the apical bud removed continued to show gus gene expression when exposed to the ethylene pathway precursor ACC but gus gene expression was suppressed in shoots with the apical bud intact when exposed to the ethylene pathway inhibitor AOA (FIG. 14B-D). Intact shoots continued to show gus gene expression when exposed to ethephon, a compound that is degraded in the plant tissue to generate ethylene.

These data indicated that the LEACO1$_{0.821\ kb}$ promoter is induced by ethylene biosynthetic pathway activity, and also demonstrated a role for endogenous auxin in triggering LEACO1$_{0.821\ kb}$ promoter activity. Blume and Grierson (1997) reported an increase in LEACO1 promoted gus expression in plants exposed directly to ethylene. In their study, gus expression was similar when promoted by either a 396 bp or a 1825 bp fragment of the LEACO1 gene promoter. While the 1825 bp fragment contained a number of short motifs that have been reported to be important for regulating many genes involved in stress response during senescence or for ethylene response the 396 bp fragment did not include any of these short motifs. In the present study, the 821 bp fragment of LEACO1 used to drive IPT (and GUS) expression included two copies of the TCA motif and one copy of the 8 bp ethylene responsive element. In addition, five copies of the required sequence for AuxREs and five copies of the G-box regulatory element or the G-box core sequence were included.

Our observation with LEACO1$_{0.821\ kb}$-gus and LEACO1$_{0.821\ kb}$-ipt in response to the ethylene generating compound ethephon raises an interesting questions about the interplay of various plant hormones in regulating LEACO1$_{0.821\ kb}$ activity. In LEACO1$_{0.821\ kb}$-gus with intact apical buds, GUS expression remained high when plants were exposed to ethephon. While this observation did not suggest an increase in GUS expression (GUS expression was normally high in LEACO1$_{0.821\ kb}$-gus with intact apical buds, FIG. 14), ethephon certainly did not reduce GUS expression. However, when LEACO1$_{0.821\ kb}$-ipt plants were exposed to ethephon, expression of the IPT gene was suppressed (based on RT-PCR analysis, FIG. 7). One would expect ethephon to stimulate ethylene pathway activity in general, and thus increase expression in genes under the control of the LEACO1$_{0.821\ kb}$ promoter. However, Liu (1997) reported that ethephon did not affect ACC oxidase mRNA levels in sunflower hypocotyls, while in mung bean hypocotyls Kim et al. (2001) observed increased ACC oxidase transcription levels and decrease ACC synthase transcription levels in response to ethylene gas.

Simple negative feedback or autoinhibition of ethylene could explain the response observed in our study. Autoinhibition of endogenous ethylene production has been described in banana fruit tissue (Vendrell and McGlasson 1971), fruits of sycomore fig (Zeroni and Galil 1976), citrus peel discs (Riov and Yang 1982), and avocado (Zauberman and Fuchs 1973). Autoinhibition of ethylene synthesis results from the reduction in ACC availability (Riov and Yang 1982). In the case of $LEACO1_{0.821\ kb}$-ipt plants, perhaps initial increases in cytokinin concentrations upon an ethephon treatment served to stimulate ethylene biosynthesis, but additional ethylene generation could have produced a negative feedback on ethylene biosynthesis and a subsequent down regulation of the $LEACO1_{0.821\ kb}$-ipt gene. However, if autoinhibition of endogenous ethylene production were responsible for down regulating $LEACO1_{0.821\ kb}$ promoter activity, one might expect that GUS expression would decrease in the presence of ethephon as well.

The fact that 24 hours after ethephon treatment, plants carrying the $LEACO1_{0.821\ kb}$-ipt showed a marked decrease in mRNA from IPT gene expression may be explained with another more likely mechanism: autoinhibition of the $LEACO1_{0.821\ kb}$-ipt gene by increased cytokinin concentrations. Although cytokinin can induce ethylene biosynthesis in plants (Vogel et al. 1998a; Vogel et al. 1998b), it has been shown that cytokinin, an antisenescence hormone, often produces physiological effects opposite of ethylene, a senescence hormone. It is therefore possible that expression of the $LEACO1_{0.821\ kb}$-ipt gene, which leads to an increase in cytokinin concentrations in plants, may result in an inhibition of $LEACO1_{0.821\ kb}$ gene promoter activity, that is similar to the expression of the SAG12-ipt (Gan and Amasino 1995). Kim et al. (2001) found reduced ACC oxidase activity and a progressive reduction in ethylene production in mung bean hypocotyl tissue exposed to increasing concentrations of BA, and Coenen et al. (2003) reported cytokinin inhibited auxin-induced ethylene synthesis in tomato hypocotyl segments. However, it should be noted that in intact tomato seedlings, cytokinin stimulated ethylene synthesis (Coenen and Lomax 1998), and in mungbean hypocotyls exposed to the synthetic cytokinin BA, a synergistic increase in ethylene was observed in the presence of IAA (Lau et al. 1997; Yoshii and Imaseki 1982).

The observations on the effects of regulating ipt expression with a 821 bp fragment of LEACO1 promoter on plant morphology, provide another example of the interactions between hormones. The present study illustrates some of the ways that the induction of biosynthesis of one hormone in response to another can affect plant development. The data also indicate potential uses for this specific construct in commercial plant development. For example, increases in flower bud initiation and bud development, on plants that otherwise display a phenotype characterized by low bud numbers and strong apical dominance that results in few branches, are useful in a number of commercial crop plants from asexually propagated ornamental species to sexually propagated agronomic species. With asexually propagated crop species, unlike in sexually propagated species, trait stability in the primary transformants is important while stability in the seed progeny is not.

DEFINITIONS

A "transgene" refers to genetic material that is introduced, or is capable of being introduced, into cells of a host animal. Typically, once a "transgene" is introduced into the cells of the host animal, it is maintained, either transiently or permanently, by, e.g., insertion into the host genome. In preferred embodiments of the present invention, a transgene is inserted into the host genome by homologous recombination, thereby replacing the endogenous gene with the transgene. Often, a transgene contains a coding sequence, operably linked to a promoter, that encodes a protein, e.g., a marker protein that allows the detection of the transgene in the cell. "Transgenic" refers to any cell or organism that comprises a transgene.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA and nucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical."

The term "transduction" refers to the introduction of foreign DNA into cells of an organism (in vivo). The term "transfection" refers to the introduction of foreign DNA into cells in culture (in vitro).

The term "vector" commonly refers to a plasmid that can be used to transfer DNA sequences. Different vectors may have properties particularly appropriate for protein expression in the recipient.

"Expression vector" results in expression of inserted DNA when propagated in a suitable host cell such as a plant cell. As used herein, "cassette" may be used to designate a structure into which DNA or a vector may be inserted.

The term "substantial" as used herein refers to being nearly the same, as when expression is substantially the same from a homologous gene. In terms of substantial identity, at least 85% identity is intended.

Use of the terms "an", "a" and "the" and similar terms used in claiming or describing the invention are intended to be construed as including both the singular and plural, unless clearly otherwise indicated or contraindicated. The terms "including", "having" and "containing" are to be construed as open-ended in the same manner as the terms "comprising" or "comprises" are commonly accepted as including but not limiting to the explicitly set forth subject matter. The term "comprising" and the like are construed to encompass the phrases "consisting of" and "consisting essentially of".

The methods and processes described herein may be performed in any suitable order unless otherwise indicated or clearly rendered inoperable by a modification in order.

Limited and narrow interpretation of descriptive language intended to better illustrate the invention is not to be construed as limiting in any way nor to limit the scope of the invention contemplated by the inventors.

The invention, now described generally and in some detail, will be understood more readily by reference to the following examples, which are provided by way of reference and are in no manner intended to limit the scope of what the inventors regard as their invention.

EXAMPLES

Materials and Methods

Binary vector constructions. Using standard molecular cloning procedures and the primers (forward) 5'-GGT-TGAGTTGTTTCCCTCTG-3' (SEQ ID NO:1) and (reverse) 5'-GGTAAAGTGTTTTCCTAAGTG-3' (SEQ ID NO:2), a 0.918 kb fragment from the promoter region (including the 97 bp of 5' UTR leader sequence plus the 821 bp of the untranscribed sequence) of the *Lycopersicon esculentum* LEACO1 gene (referred to herein as LEACO1$_{0.821 kb}$) was synthesized by PCR reaction as described below. The LEACO1$_{0.821 kb}$ promoter fragment was cloned into the HindIII-SalI sites of the pBin19 binary vector, replacing the CaMV promoter fragment from the 35S-ipt-nos construct in this plasmid. The DNA sequence of the LEACO1$_{0.821 kb}$ promoter fragment in the established plasmid was confirmed by DNA sequence analysis (W.M. Keck Biotechnology Laboratory, Yale University, New Haven, Conn.). The binary plasmid was transferred into *Agrobacterium tumefaciens* strain LBA 4404 or EHA105 by electroporation.

To construct a gene containing gus under the control of the LEACO1$_{0.821 kb}$ fragment, the pBin19-LEACO1$_{0.821 kb}$-ipt vector was cut by SalI and SacI releasing the ipt gene. Similarly, the gus gene was released from the pUC19-gus-nos construct by digestion with SalI and SacI. Both DNA were dephosphorylated and then LEACO1$_{0.821 kb}$-nos and gus fragments were ligated together. The plasmid containing the whole LEACO1$_{0.821 kb}$-gus-nos fragment in pBin19 binary vector was transferred into *Agrobacterium tumefaciens* strain LBA 4404 by electroporation.

Transformation and production of transgenic tobacco plants. Tobacco plants were transformed using the *Agrobacterium*-mediated transformation method. Briefly, young tobacco leaves were surface-sterilized, cut into discs and co-cocultivated with *Agrobacterium tumefaciens* LBA 4404 bearing the LEACO1-ipt construct or LEACO1-gus construct. Following co-cultivation, the explants were transferred to the MS medium supplemented with 0.1 mg/l α-naphthaleneacetic acid and 1 mg/l 6-benzylaminopurine. Kanamycin at 300 mg/l was used for selection and timentin at 400 mg/l was used to suppress *Agrobacterium*. Explants were transferred on fresh medium at 2-3 week intervals until shoots began to emerge from the transgenic calli. Excised shoots were then transferred to MS medium containing 100 mg/l of kanamycin until roots developed. Finally, rooted plantlets were transferred to pots containing Metro 510 (Scotts, Co., Marysvill, Ohio, USA) and acclimated to the growth environment at 25° C. Individual, transgenic lines were then analyzed by PCR for foreign genes integration. Seeds from primary transformants $T_0$ and also from generation $T_1$ were germinated on MS agar medium containing 100 mg/l of kanamycin.

Plant DNA extraction and polymerase chain reaction (PCR) analysis. Total DNA was isolated from leaf tissue of greenhouse grown plants ($T_0$ and $T_1$ generations) using DNeasy Plant Mini Kits (Qiagen Inc., Valencia, Calif., USA) and 250 ng of DNA was subjected to PCR reaction. The primers used to detect the recombinant DNA were (i) forward primer 6'-GGTTGAGTTGTTTCCCTCTG-3' (SEQ ID NO:1) and reverse primer 6'-GGTAAAGTGTTTTC-CTAAGTG-3' (SEQ ID NO:2) specific for the 0.918 kb fragment (nucleotides −1-918) of LEACO1 promoter plus UTR leader; (ii) forward primer 5'-GGTCCAACTTGCACAG-GAAAG-3' (SEQ ID NO:3) and reverse primer 6'-GGCT-TGCCTACTGGAAGCTTA-3' (SEQ ID NO:4), specific for the 0.525 kb region of the ipt gene (full size—0.723 kb); PCR amplification was performed using a thermocycler (Gene-Amp PCR System 2700, Applied Biosystems, Inc., Foster City, Calif., USA). Cycling conditions for both genes were 3 min at 94° C., 30 cycles of 1 min at 94° C., 1 min at 58° C., and 1 min 30 sec at 72° C., and extension at 72° C. for 5 min. The reactions involved 200 ng of DNA template, 0.2 mM of dNTPs, 0.5 μM of each primer, REDTaq PCR Buffer and 1 unit of REDTaq DNA polymerase (Sigma, Saint Louis, Mo., USA). Finally, a 10 μl aliquot of PCR product was observed under UV after electrophoresis on a 1% agarose gel with ethidium bromide. A 1-kb DNA molecular marker (Gibco BRL, Carlsbad, Calif., USA) was used as a reference to determine DNA fragment size.

Southern hybridization. Genomic DNA was isolated from transgenic plants using a DNeasy Plant Maxi Kit (Qiagen Inc., Valencia, Calif., USA) following the manufacturer's protocol. A 10 □g per sample of total genomic DNA from putative transgenic and non-transformed control plants was digested overnight by restriction with HindIII at 37° C. Digested DNA of each line was separated through a 1% agarose gel prepared in 1×TAE and fragments were transferred from the agarose gel to a nylon membrane (Amersham, Chalfont St Giles, UK) and cross-linked to the membrane by UV treatment. The ipt gene probe (0.52 kb fragment of the 0.7 kb ipt gene) was prepared with a PCR DIG Probe Synthesis Kit (Roche Molecular Biochemicals, Indianapolis, Ind.) according to the manufacturer's instructions. DNA fixed on membranes was pre-hybridized with a pre-hybridizing solution at 68° C. for 3 hours, hybridized with probe at 68° C. overnight and washed by post-hybridization solution 4 times for 15 min. at 65° C. in a hybridization oven.

Solutions used for sample hybridization, pre- and post-hybridization, and buffers for the ensuing steps were prepared as previously reported by Mercier (1998). Membranes were washed for 5 min. in 50 ml of maleate buffer (0.1 M of maleic acid and 3.0 M of NaCl) at room temperature and then incubated for 1 hour in 50 ml of blocking solution (maleate buffer plus 0.5% blocking reagent (Roche Molecular Biochemicals, Indianapolis, Ind., USA). Next, membranes were incubated for 30 min. in 20 ml of blocking solution plus anti-dioxigenin-AP, Fab fragments (Roche Molecular Biochemicals, Indianapolis, Ind., USA) diluted to 1:10,000 and then washed 4 times for 10 min. in 50 ml of the maleate buffer.

As a final step, membranes were equilibrated for 5 min. in 50 ml of substrate buffer (100 mM of Tris-HCl; 100 mM of NaCl; 5 mM of $MgCl_2$) and then incubated at 37° C. for 10 min in 2 ml (sandwiched between two translucent plastic pages) of substrate buffer plus chemiluminescent substrate at a 1:100 dilution (CSPD, Roche Molecular Biochemicals, Indianapolis, Ind., USA). Membranes were exposed to autoradiographic film (Kodak X-Omart AR) for 4 hours. X-ray films were developed with an automatic film processor.

Analysis of ipt expression in leaves of tobacco. Total RNA was isolated from tobacco plants by flash freezing tissue in liquid nitrogen and then grinding in a mortar with TRI reagent (Molecular Research Center, Inc., Cincinnati, Ohio, USA). For Reverse Transcription-PCR (RT-PCR) analysis, possible DNA contamination was removed from RNA samples using a DNase treatment (DNA-free™, Ambion Inc., Austin, Tex.). The first-strand cDNA was then synthesized from 1 μg of total RNA using a RETROscript™ First Strand Synthesis Kit (Ambion Inc., Austin, Tex.) following the manufacturer's instruction. For PCR, 0.5 μL of RT-mix was used in a final volume of 25 μL. The PCR reaction for the ipt gene fragment was conducted as previously described. PCR reaction products along with RT-mix and primers to 18S RNA were used as internal standards (QuantumRNA™ 18S Internal Standards, Ambion Inc.). PCR products (10 μL) were run on a 1% agarose gel.

Plant growth conditions and morphological analysis of transgenic plants. The effect of the transgene on growth and development and number of flower buds of tobacco plants was determined as follows. Shoots from each transgenic $LEACO1_{0.821\ kb}$-ipt tobacco plant lines #2 and #4 of $T_1$ generation, and from the wild-type cultivar 'Havana' were rooted in deep 606-cell packs (Kord Products, Bramalea, Ontario, Canada) containing a Metro 510 (Scotts Co., Marysville, Ohio, USA) peat-lite medium. After six weeks, plants from each line were harvested and the following data recorded: plant height, number of nodes, leaf area per plant, number of flower buds on main stem, number of lateral branches. These parameters were used to calculate the average internode length and the average area per leaf on the upper-most lateral shoot. These data were used to determine difference in vegetative growth habit between transgenic and wild-type plants. Plants were arranged in a randomized complete block design with 10 replicated blocks. Statistical effects were determined using a two-way analysis of variance with genetic line and cold-treatment as the main effects.

The effect of the transgene on growth and development and number of flower buds of chrysanthemum plants was determined as follows. Tip cuttings from $LEACO1_{0.821\ kb}$-IPT chrysanthemum lines 1, 5, and 14, and the wild-type plant 'Iridon' were rooted in Metro 510. Rooted plants were transferred to 4" pots and moved to plant growth chambers set at 25° C. day/20° C. night temperature and lit to 300 umol/m2/s for 16-hr per day. After the plants had acclimated to the growth chamber environment, plants in one chamber were exposed to a short-day condition (10-hr of light per day) to induce flower development, the plants in the other chamber continued to grow vegetatively under long day (16-hr per day) light conditions. Plants were arranged in a replicated block array with 6-replicates per chamber.

Plants under short days were harvested and the data recorded included number of branches on each plant, length of each branch, number of flower buds on each branch, and the number of nodes on each branch. Plants under vegetative growth conditions were harvested and the following data was recorded; number of branches on each plant, length of each branch, number of side secondary branches off each primary branch, and the number of nodes on each primary branch. This experiment was repeated with new root cuttings and plants exposed to short-day (flowering) conditions. In this experiment, 18 total replicated blocks were established using three growth chambers. Each replicated block included the $LEACO1_{0.821\ kb}$-IPT chrysanthemum lines 1, 5, and 14, and the wild-type plant 'Iridon'. Five plants from each line were harvested and the following data was recorded; number of branches on each plant, length of each branch, plant fresh weight, plant dry weight, total buds per plant, total leaf area per plant, and date of first open bloom. Bloom open date and bloom senescence date was recorded over time for the remaining plants in each chamber.

A larger study was initiated in early spring (around February) using cuttings from $LEACO1_{0.821\ kb}$-IPT chrysanthemum lines 6, 10, 13, 16, 17, 19, 30, 31, 32, 33, 34, 35, 36, 37, 38, 39, 40, 41, 42, 43, 44, 45, 46, 47, 48, 49, 50, 51, 52, and the non-transgenic wild-type. Plants were grown in 608 cell packs with Metro 510. Approximately two months later, each plant was pinched to a total of five nodes, and on about two weeks later the plants were exposed to short day conditions in the greenhouse to induce flowering. Plants were harvested on after about 3.5 months later and the following parameters were recorded; numbers lateral branches per plant, length of branches, number of buds per lateral, number of nodes per branch, bud diameter at anthesis, bud diameter at the onset of senescence, and the date of bud anthesis and bud senescence. From these data the average number of buds per plant, average internode length, days from flower initiation to first anthesis, and days from anthesis to senescence were calculated.

In a follow up study, eight plants from each of 26 transgenic lines and the wild-type were grown in 5-inch pots in the greenhouse until flowering. At flowering the following data was recorded; plant fresh weight, number of lateral branches on each plant, length of each lateral branch, number of nodes on each lateral branch, total number of flower buds on each lateral branch, date of first open bloom, and bud diameter on top bud. The plant lines used in this study included LEACO1$_{0.821\ kb}$-IPT chrysanthemum lines 1, 4, 5, 6, 10, 13, 14, 16, 17, 19, 31, 32, 33, 35, 37, 38, 40, 41, 42, 43, 45, 47, 48, 49, 50, 51, 52, and the non-transgenic wild-type. Results of this study are summarized in Table 2b.

The effects of ethylene on the ipt gene expression in two transgenic tobacco plant lines (N2 and N4) was investigated by spraying plants in the greenhouse with ethephon (500 mg/l) and then sampling tissue after 1.5 days. RNA was isolated from the tissue samples, and RT-PCR analysis was conducted as previously described.

Quantification of Chlorophyll. Specific chlorophyll concentration was calculated as follows. Leaf tissue from each sample was blotted dry, weighed, and placed in a 1.5-mL Eppendorf tube. The samples were resuspended in 80% acetone, ground with a disposable pestle, and incubated in the dark for 30 min. Total chlorophyll (Chl µg mL$^{-1}$) was determined according to the equation: $20.2\ A_{645} + 8.02\ A_{663}$.

Application of chemicals and histochemical analysis of GUS activity. Individual transgenic LEACO1$_{0.821\ kb}$-gus tobacco seedlings (lines N3 and N5 of T$_1$ generation), that showed positive β-glucuronidase activity, were treated with either IAA, the ethylene synthesis inhibitor aminooxyacetic acid (AOA), the auxin transport inhibitor 2,3,5-triiodobenzoic acid (TIBA), the ethylene precursor 1-aminocyclopropane-1-carboxylic acid (ACC), or the ethylene generating compound ethephon. AOA, ACC, IAA, TIBA were from Sigma (Sigma-Aldrich, Inc., St. Louis, Mo., USA). Ethephon was from Rhone-Poulenc Ag Company (Monterey, Calif., USA). In the initial experiment, 100 mg/l IAA in lanolin was applied to the apex of an excised shoot, 2500 mg/l TIBA was applied in a lanolin ring directly below the intact apex, and 0.5 mM AOA was brushed on the stem surface below the apex.

In a second experiment, ACC ($10^{-5}$ M), ethephon (500 mg/l) and AOA were applied as sprays but TIBA was applied as previously described. ACC was applied to seedlings that had the shoot apex removed, and the other compounds were applied to plants with the apex intact. All chemicals were reapplied every 2 days, and after six days the seedlings were harvested and histochemical analysis was conducted. In both experiments, untreated seedlings with the apex intact or with the apex removed were used as control treatments.

For histochemical assays of β-glucuronidase activity, the stems of young LEACO1$_{0.821\ kb}$-gus tobacco seedlings were sectioned by hand. Stem sections were vacuum infiltrated with a staining solution containing 1 mM X-GLUC (5-bromo-4-chloro-3-indolyl-β-D-glucuronic acid) and incubated at 37° C. for 24 h. After staining, samples were rinsed with water and fixed in 70% ethanol. Each treatment was sampled in triplicate. Results of GUS-activity were documented using digital photography (Olympus 3× optical zoom and Olympus light microscope (SZH10) with 0.7× magnification).

The following examples are provided as illustrations of the invention and are in no way to be considered limiting.

Example 1

Transformation of tobacco. Tobacco plants were transformed using *Agrobacterium*-mediated transformation method. Young tobacco leaves were surface-sterilized, cut in discs and co-cocultivated with *Agrobacterium tumefaciens* LBA 4404 bearing the LEACO1$_{0.821\ kb}$-ipt construct or LEACO1$_{0.821\ kb}$-gus construct. Following co-cultivation, the explants were transferred to the MS medium (Murashige and Skoog, 1962) supplemented with 0.1 mg/l α-naphthaleneacetic acid and 1 mg/l 6-benzylaminopurine. Kanamycin at 300 mg/l was used for selection and timentin at 400 mg/l was used to suppress *Agrobacterium*. Explants were transferred on fresh medium at 2-3 week intervals until shoots began to emerge from the transgenic calli. Excised shoots were then transferred to MS medium containing 100 mg/l of kanamycin until roots developed. Finally, rooted plantlets were then transferred to pots containing Metro 510 (Scotts, Co., Marysville, Ohio) and acclimated to the greenhouse. Individual, transgenic lines were then analyzed by PCR (FIG. 4) to confirm integration of the foreign gene. Seeds from primary transformants T$_0$ and also from generation T$_1$ were germinated on MS agar medium containing 100 mg/l of kanamycin (FIG. 4).

Example 2

Transformation of petunia and chrysanthemum. Leaves of young (1 month old) petunia (cv. *Marco Polo Odyssey*) were sterilized with 10% Clorox for 15-20 min. and then rinsed 5-times with sterile water. The young, soft stems of chrysanthemum plants (cv. Iridon) were washed for 60 sec with 70% ethanol, rinsed 3-times with sterile water, and then sterilized in 5% Clorox for 8 min. before finally rinsing 5-times with sterile water. The bacterial suspension was cultured in LB medium supplemented with 50 mg/L kanamycin and 25 mg/L rifampicin. The suspension was incubated at 25° C. on a rotary shaker (220 rpm) until achieving an optical density of 0.4-0.7 (λ600 nm). The suspension was then centrifuged and the pellet re-suspended in a fresh liquid MS medium.

Leaf explants of petunia or stem segments of chrysanthemum were soaked in the infection medium for 5 min., blotted dry and kept 3 days in the dark at 22-25° C. on plates with MS medium containing 2 mg/L of N$^6$-benzyladenine (BA), 0.01 mg/L of NAA for petunia explants or 0.225 mg/L of BA, 2 mg/L of IAA for chrysanthemum explants. After 2-3 days, explants were transferred to the respective selection media containing 50 mg/L of kanamycin (for selection) and 200 mg/L of timentin (to eliminate the *Agrobacterium*). Explants were transferred to fresh medium every 2-3 weeks, until shoots developed. Excised shoots were then transferred to phytohormone-free MS medium containing 50 mg/L of kanamycin and 100 mg/L of timentin until root induction was evident. Rooted explants were transferred to a peat-based medium, Metro 510 (Scotts Co., Marysville, Ohio) and acclimated to the greenhouse.

Example 1

Protocol for Poinsettia Transformation. Poinsettia explants were transformed using *Agrobacterium*-mediated transformation method. Young poinsettia stems were harvested from the greenhouse, the leaves removed and the stems surface-sterilized in 5% chlorox solution by lightly brushing the stem surface for six minutes. Stem internode sections are then cut into segments 0.3-0.5 cm long and then cut again longitudinally (FIG. 4b). The section are plated on MS medium (with N&N vitamins and 0.1 mg/l TDZ) for a 5-day preculture period. After preculture explants are individually dipped into a broth of *Agrobacterium tumefaciens* LBA 4404 bearing the LEACO1$_{0.821\ kb}$-ipt construct or LEACO1$_{0.821\ kb}$-gus construct for 0.5 sec and then immediately blotted dry on sterile paper. The *Agrobacterium* inoculated explants are co-cultured for 2-4 days, and then plated onto selection medium [MS medium (Murashige and Skoog, 1962) supplemented with 0.1 mg/l TDZ and N&N vitamins] containing kanamycin and timentin at 400 mg/l. For the poinsettia cultivar 'Red Success' a kanamycin concentration 9-10 mg/l is used for selection. For the poinsettia cultivar 'Winter Rose Dark Red' a kanamycin concentration 0.5-1 mg/l is used for selection. Explants were transferred on fresh medium at 2-3 week intervals until a callus mass forms and begins to produce shoot initials. The shoots are then excised, transferred to hormone free media until root initials form. Finally, rooted plantlets were then transferred to pots containing Metro 510 (Scotts, Co., Marysville, Ohio) and acclimated to the greenhouse.

Cytokinin levels in the vegetative shoots of wild-type compared with the transformed plants are shown in Table 1. Growth characteristics of transgenic chrysanthemum plants are illustrated in FIG. 15.

Z, trans-zeatin; Z9R, zeatin 9-riboside; Z9ROG, zeatin 9-riboside O-glucoside; ZMP, zeatin monophosphate; ZOG, trans-zeatin O-glucoside; Z7G, trans-zeatin-7-glucoside; Z9G, trans-zeatin-9-glucoside; DHZ, dihydrozeatin; DHZOG, dihydrozeatin O-glucoside; DHZ7G-1, dihydrozeatin-7-glucoside-1; DHZ7G-2, dihydrozeatin-7-glucoside-2; DHZ9G, dihydrozeatin-9-glucoside; DHZ9R, dihydrozeatin-9-riboside; DHZ9ROG, dihydrozeatin riboside-O-glucoside, iP, Isopenenyl adenine; iP7G, Isopenenyl adenine-7-glucoside; iP9G, Isopenenyl adenine-9-glucoside; iPR, Isopentenyl adenosine; iP7R, Isopentenyl adenosine 7-riboside; iPMP, isopentenyl monophosphate.

Table 2 shows phenotypic characteristics of chrysanthemum transformants compared with wild-type flowering performance of leaco1$_{0.821\ kb}$-ipt chrysanthemum lines under greenhouse conditions. Plants were grown in the greenhouse in 2004 in 608 cell packs. Transgenic plants showed a wide range of branching and flowering phenotypes. Relative to control, some transgenic lines produced only 10% more flower buds but most lines (19 out or 29) showed a 50% (or greater) increase in bud count. Further, five transgenic lines produced an 8 to 10 fold increase in flower buds relative to the wild-type plant. The LEACO1$_{-0.821\ kb}$-ipt gene similarly influenced branch development. Of the 29 transgenic lines tested in this study, 12 displayed an increase in branching habit ranging from 130% to over 340% of the number pro-

TABLE 1

Cytokinin concentrations in wild-type and transgenic LEACO1$_{0.821kb}$-ipt chrysanthemum plants (lines, 1, 5, 14).

| Genetic line | Cytokinin types (amount in pmol g$^{-1}$ DW) | | | | | |
|---|---|---|---|---|---|---|
| | Total active[1] | Total storage[2] | Total deactivated[3] | Total Mono-phosphate forms[4] | Cis-form pool (active)[5] | Cis-form pool (storage)[6] |
| | Vegetative shoots | | | | | |
| Wild type | 47.8 ± 10.1 | 55 ± 8.5 | 38.0 ± 8 | 75.7 ± 15.1 | 20.5 ± 7.8 | 856 ± 55 |
| LEACO1$_{0.821kb}$-ipt N1 | 29.8 ± 5 | 75 ± 31 | 66.5 ± 38 | 45.7 ± 16.3 | 12.1 ± 2.9 | 920 ± 126 |
| LEACO1$_{0.821kb}$-ipt N14 | 75.1 ± 28.5 | 108 ± 28 | 89.2 ± 29 | 46.2 ± 19.9 | 44.5 ± 2.1 | 1189 ± 143 |
| LEACO1$_{0.821kb}$-ipt N5 | 41 ± 9.6 | 51 ± 0.7 | 44.2 ± 2.2 | 72.9 ± 13.9 | 12.3 ± 3.6 | 847 ± 80 |
| | Generative shoots | | | | | |
| LEACO1$_{0.821kb}$-ipt N5 | 187 ± 40.6 | 167 ± 28 | 2979 ± 411 | 15.4 ± 7.1 | 162.1 ± 49.9 | 539 ± 43.8 |
| | Statistical effects | | | | | |
| | P ≦ 0.001 | P ≦ 0.01 | P ≦ 0.0001 | P = 0.08 | P ≦ 0.01 | P ≦ 0.01 |

Figure 16:
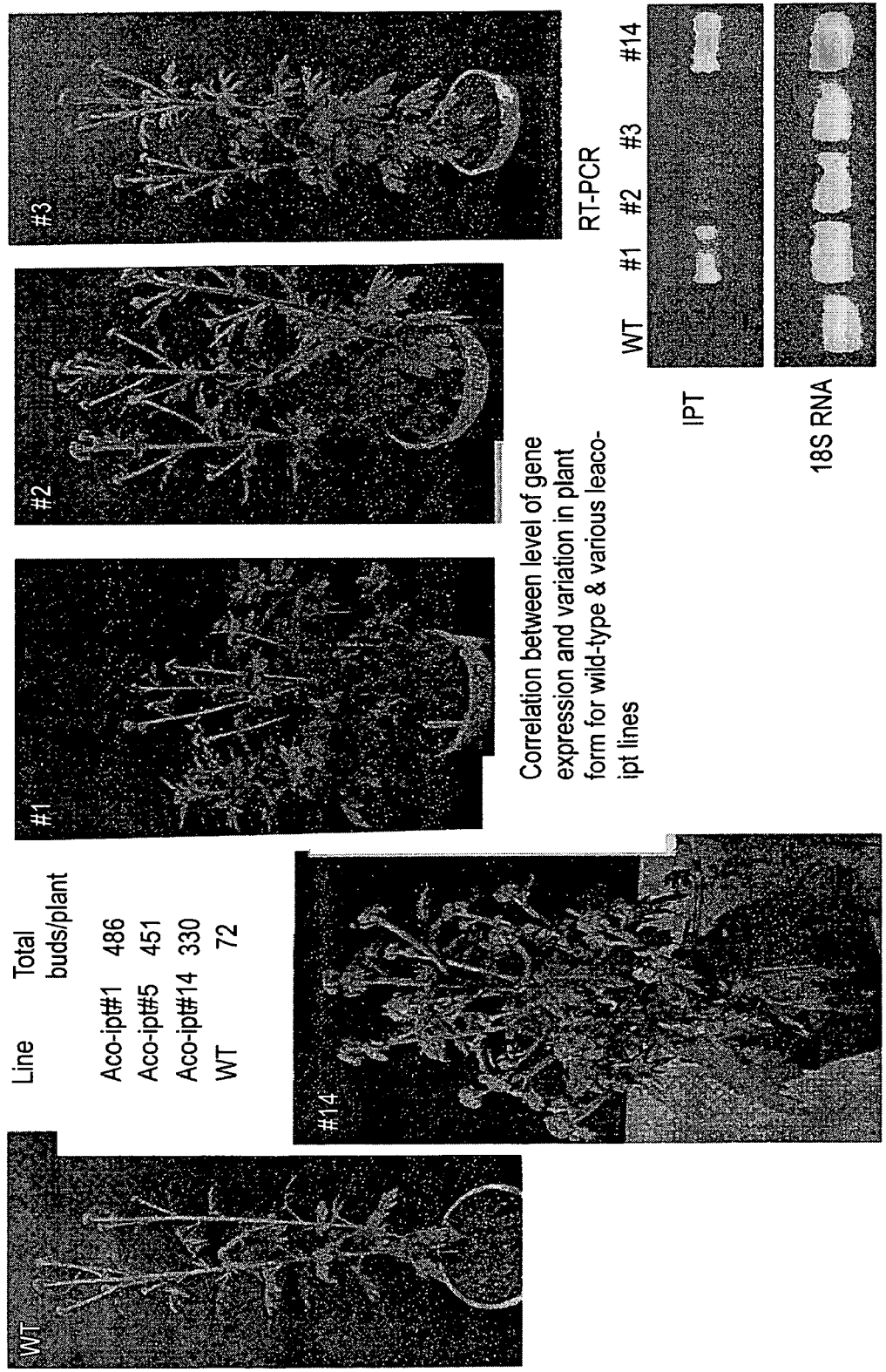
FIG. 16. Growth habit wild-type and selected leaco1$_{-0.821\ kb}$-ipt chrysanthemum lines. (lower right) RT-PCR analysis shows a strong correlation between the intensity of the mRNA signal and the increase in branching and flower bud number in the leaco1$_{0.821\ kb}$-ipt plants. Note that line #3 that has a phenotype similar to the wild-type shows no mRNA transcript (does not express the ipt gene) while line #14 shows a dramatic increase in bud and branch number, a corresponding high level of gene expression (mRNA) and high cytokinin concentrations (see FIG. 15, bottom center). Bud counts for wildtype plants and selected transgenic lines grown in the growth chamber.

Active pool: Z, DHZ, Z9R, DHZ9R, iP, iPR, iP9R
Storage pool: ZOG, DHZOG, Z9ROG, DHZ9ROG
Deactivated pool: Z7G, DHZ7G-1, DHZ7G-2, Z9G, DHZ9G, iP7G, iP9G
Total Mono-phosphate forms ZMP, iPMP
Cis-form pool (active): c-Z, c-Z9R
[6]Cis-form (Storage) c-ZOG, c-Z9ROG duced by the wild-type line. Correlation between level of gene expression and variation in plant form for wild-type and several LEACO1$_{-0.821\ kb}$-ipt lines is illustrated in FIG. 16.

Table 3 shows phenotypic characteristics of chrysanthemum transformants compared with wild-type flowering performance of leaco1$_{-0.821\ kb}$-ipt chrysanthemum lines under greenhouse conditions. Plants were grown in the greenhouse in 2005 in 5-inch pots. As in Table 2, the 27 lines tested showed a wide range of branching and flowering phenotypes

TABLE 2

Leaco1-IPT Chrysanthemum lines: Flowering performance evaluation 2004
Sort Basis: Average NO# buds per plant

| Genetic line | Average NO# buds per plant | Average NO# laterals per plant | Average lateral length (cm) | Average NO# buds per lateral | Average internode length (mm) | Average diameter buds at anthesis (mm) | Average diameter buds at senescence (mm) | Days from initiation to anthesis | Days from anthesis to senescence | Percent (%) relative total bud count per plant (relative to wild-type) |
|---|---|---|---|---|---|---|---|---|---|---|
| Wild-type | 15.5 | 2.67 | 18.7 | 5.8 | 10.5 | 18.7 | 57.0 | 53.7 | 33.3 | 100 |
| leaco1-ipt 36 | 16.8 | 2.83 | 25.3 | 5.9 | 11.8 | 18.7 | 47.0 | 65.0 | 38.0 | 109 |
| leaco1-ipt 51 | 19.0 | 2.50 | 17.9 | 7.6 | 10.2 | 18.3 | 45.3 | 57.0 | 42.3 | 123 |
| leaco1-ipt 44 | 19.3 | 2.50 | 17.5 | 7.7 | 10.6 | 19.0 | 50.0 | 57.7 | 41.3 | 125 |
| leaco1-ipt 50 | 20.8 | 2.17 | 18.9 | 9.6 | 10.8 | 19.7 | 46.3 | 62.3 | 40.7 | 134 |
| leaco1-ipt 43 | 21.0 | 2.50 | 20.3 | 8.4 | 12.8 | 19.7 | 49.3 | 56.0 | 37.0 | 135 |
| leaco1-ipt 49 | 21.2 | 2.17 | 18.0 | 9.8 | 10.6 | 20.3 | 44.3 | 57.0 | 38.0 | 137 |
| leaco1-ipt 30 | 21.3 | 3.17 | 25.7 | 6.7 | 12.5 | 18.3 | 53.3 | 56.3 | 41.0 | 138 |
| leaco1-ipt 46 | 21.8 | 3.50 | 16.1 | 6.2 | 9.5 | 19.7 | 51.0 | 58.3 | 34.3 | 141 |
| leaco1-ipt 34 | 23.0 | 3.00 | 24.1 | 7.7 | 11.8 | 18.7 | 58.0 | 55.0 | 41.0 | 148 |
| leaco1-ipt 40 | 24.0 | 3.00 | 23.3 | 8.0 | 11.4 | 14.0 | 54.0 | 55.7 | 38.3 | 155 |
| leaco1-ipt 47 | 24.0 | 3.17 | 18.2 | 7.6 | 11.1 | 26.7 | 50.3 | 62.0 | 40.0 | 155 |
| leaco1-ipt 52 | 24.0 | 3.83 | 14.0 | 6.3 | 8.4 | 20.0 | 41.0 | 63.7 | 39.0 | 155 |
| leaco1-ipt 41 | 24.5 | 3.17 | 23.0 | 7.7 | 10.8 | 17.3 | 53.3 | 56.7 | 41.3 | 158 |
| leaco1-ipt 35 | 24.8 | 3.17 | 25.2 | 7.8 | 11.3 | 18.3 | 52.0 | 56.7 | 38.3 | 160 |
| leaco1-ipt 42 | 24.8 | 4.00 | 22.0 | 6.2 | 9.4 | 20.0 | 43.7 | 71.7 | 32.0 | 160 |
| leaco1-ipt 33 | 25.0 | 3.33 | 25.6 | 7.5 | 12.3 | 18.3 | 53.3 | 57.0 | 37.7 | 161 |
| leaco1-ipt 31 | 29.5 | 3.67 | 24.3 | 8.0 | 12.2 | 19.0 | 44.3 | 66.0 | 34.3 | 190 |
| leaco1-ipt 37 | 29.8 | 3.17 | 24.1 | 9.4 | 11.4 | 15.3 | 44.0 | 59.7 | 43.3 | 192 |
| leaco1-ipt 32 | 30.0 | 3.33 | 23.2 | 9.0 | 11.4 | 19.3 | 50.0 | 64.7 | 33.7 | 194 |
| leaco1-ipt 38 | 31.3 | 3.50 | 21.8 | 9.0 | 11.1 | 19.0 | 47.0 | 66.7 | 34.0 | 202 |
| leaco1-ipt 48 | 32.8 | 3.17 | 16.3 | 10.4 | 10.0 | 19.3 | 51.7 | 58.7 | 38.7 | 212 |
| leaco1-ipt 45 | 54.0 | 4.50 | 14.6 | 12.0 | 8.8 | 22.3 | 27.7 | 73.7 | 36.3 | 348 |
| leaco1-ipt 6 | 70.3 | 5.00 | 16.4 | 14.1 | 10.5 | 18.3 | 27.7 | 69.0 | 31.7 | 454 |
| leaco1-ipt 19 | 136.3 | 6.17 | 17.5 | 22.1 | 10.5 | 16.5 | 22.5 | 75.0 | 34.0 | 880 |
| leaco1-ipt 10 | 136.3 | 7.50 | 14.6 | 18.2 | 8.3 | 18.5 | 26.5 | 83.5 | 28.0 | 880 |
| leaco1-ipt 17 | 142.3 | 5.50 | 16.6 | 25.9 | 9.0 | 16.0 | 25.3 | 74.7 | 35.3 | 918 |
| leaco1-ipt 13 | 153.2 | 9.17 | 13.8 | 16.7 | 8.3 | 14.5 | 20.0 | 78.5 | 32.5 | 988 |
| leaco1-ipt 16 | 154.7 | 6.83 | 15.2 | 22.6 | 8.6 | 16.0 | 21.0 | 73.0 | 35.0 | 998 |

TABLE 3

Phenotypic traits of wild type and leaco1$_{-0.821kb}$-IPT transgenic chrysanthemum (*Dendranthemum X grandiflorum* cv. Iridon) lines that exhibit a range of flowering and branching characteristics.

| Genotype (*Dendranthemum X grandiflorum*) | Line | Shoot fresh weight (g) | Lateral shoots per plant (#) | Total flower buds per plant (#) | Shoot length top lateral (cm) | Internode length on top lateral (cm) | Flower buds on top lateral (#) | Number of flower buds per lateral (#) | Time from start of short-days until bloom (days) |
|---|---|---|---|---|---|---|---|---|---|
| | | | | Means ± (se) | | | | | |
| Cultivar 'Iridon' | WT | 87.0 (4.9) | 2.9 (0.1) | 23.1 (1.5) | 23.2 (0.5) | 1.26 (0.03) | 9.6 (0.9) | 8.2 (0.6) | 50.6 (1.3) |
| leaco1$_{-0.821kb}$-IPT | N1 | 71.8 (4.2) | 5.5 (0.3) | 154.6 (7.7) | 20.7 (0.6) | 1.02 (0.02) | 46.0 (2.0) | 28.3 (1.2) | 62.9 (1.6) |
| leaco1$_{-0.821kb}$-IPT | N4 | 56.9 (3.9) | 2.9 (0.1) | 24.6 (1.6) | 17.9 (0.4) | 0.94 (0.02) | 9.6 (0.5) | 8.6 (0.5) | 53.6 (1.0) |
| leaco1$_{-0.821kb}$-IPT | N5 | 67.3 (2.6) | 4.1 (0.4) | 88.0 (5.3) | 22.7 (0.5) | 1.18 (0.03) | 32.9 (2.0) | 21.9 (1.3) | 56.9 (1.2) |
| leaco1$_{-0.821kb}$-IPT | N6 | 59.2 (4.5) | 3.6 (0.3) | 77.4 (7.7) | 21.8 (0.9) | 1.20 (0.03) | 29.9 (3.7) | 21.4 (1.8) | 57.3 (1.1) |
| leaco1$_{-0.821kb}$-IPT | N10 | 58.6 (4.8) | 5.3 (0.3) | 153.1 (7.6) | 18.5 (0.4) | 0.99 (0.03) | 46.5 (3.6) | 29.5 (1.3) | 65.4 (1.7) |
| leaco1$_{-0.821kb}$-IPT | N13 | 74.7 (2.5) | 5.5 (0.3) | 166.0 (7.0) | 20.1 (0.3) | 1.04 (0.03) | 52.9 (2.2) | 30.6 (1.4) | 60.3 (0.9) |
| leaco1$_{-0.821kb}$-IPT | N14 | 62.6 (5.3) | 5.8 (0.2) | 148.5 (9.4) | 19.6 (0.5) | 1.04 (0.02) | 43.3 (4.1) | 26.1 (2.1) | 57.8 (1.2) |
| leaco1$_{-0.821kb}$-IPT | N16 | 68.7 (5.1) | 5.1 (0.2) | 158.4 (10.0) | 20.4 (0.7) | 1.07 (0.04) | 50.8 (4.1) | 31.2 (2.3) | 63.3 (0.9) |
| leaco1$_{-0.821kb}$-IPT | N17 | 70.7 (3.0) | 6.3 (0.3) | 156.4 (7.7) | 19.8 (0.5) | 1.06 (0.03) | 46.5 (3.2) | 25.2 (1.4) | 59.9 (1.5) |
| leaco1$_{-0.821kb}$-IPT | N19 | 79.0 (4.6) | 6.5 (0.2) | 184.9 (11.1) | 19.7 (0.5) | 1.05 (0.04) | 48.6 (2.8) | 28.5 (1.4) | 62.8 (1.5) |
| leaco1$_{-0.821kb}$-IPT | N31 | 104.4 (6.4) | 4.1 (0.2) | 38.5 (2.5) | 25.3 (0.7) | 1.23 (0.03) | 12.4 (0.7) | 9.5 (0.6) | 56.5 (1.0) |
| leaco1$_{-0.821kb}$-IPT | N32 | 89.8 (5.8) | 3.3 (0.2) | 32.3 (2.5) | 24.7 (0.4) | 1.25 (0.03) | 11.6 (1.2) | 9.9 (0.6) | 55.8 (0.6) |
| leaco1$_{-0.821kb}$-IPT | N33 | 89.6 (4.1) | 3.1 (0.1) | 26.0 (1.6) | 26.9 (0.5) | 1.21 (0.01) | 9.8 (0.7) | 8.4 (0.7) | 52.8 (1.0) |
| leaco1$_{-0.821kb}$-IPT | N35 | 90.3 (4.3) | 3.4 (0.3) | 26.6 (1.8) | 27.9 (0.5) | 1.34 (0.02) | 9.0 (0.8) | 8.0 (0.5) | 53.1 (0.6) |
| leaco1$_{-0.821kb}$-IPT | N37 | 106.5 (6.8) | 4.1 (0.4) | 37.1 (3.2) | 23.8 (0.4) | 1.16 (0.02) | 11.3 (0.9) | 9.3 (0.8) | 54.0 (1.1) |
| leaco1$_{-0.821kb}$-IPT | N38 | 89.1 (6.4) | 3.6 (0.3) | 34.6 (2.2) | 24.4 (0.6) | 1.17 (0.02) | 11.6 (0.9) | 10.0 (1.1) | 54.4 (0.5) |

TABLE 3-continued

Phenotypic traits of wild type and leaco1$_{-0.821kb}$-IPT transgenic chrysanthemum (*Dendranthemum X grandiflorum* cv. Iridon) lines that exhibit a range of flowering and branching characteristics.

| Genotype (*Dendranthemum X grandiflorum*) | Line | Shoot fresh weight (g) | Lateral shoots per plant (#) | Total flower buds per plant (#) | Shoot length top lateral (cm) | Internode length on top lateral (cm) | Flower buds on top lateral (#) | Number of flower buds per lateral (#) | Time from start of short-days until bloom (days) |
|---|---|---|---|---|---|---|---|---|---|
| leaco1$_{-0.821kb}$-IPT | N40 | 87.8 (3.1) | 3.1 (0.1) | 23.3 (0.9) | 26.3 (0.6) | 1.27 (0.04) | 8.5 (0.6) | 7.5 (0.4) | 50.1 (0.8) |
| leaco1$_{-0.821kb}$-IPT | N41 | 82.2 (4.4) | 3.3 (0.2) | 23.3 (1.4) | 25.6 (0.3) | 1.26 (0.02) | 8.0 (0.4) | 7.2 (0.4) | 51.4 (0.8) |
| leaco1$_{-0.821kb}$-IPT | N42 | 68.5 (3.8) | 3.6 (0.2) | 29.0 (2.7) | 23.2 (0.5) | 1.04 (0.01) | 8.5 (0.8) | 8.0 (0.7) | 57.4 (1.3) |
| leaco1$_{-0.821kb}$-IPT | N43 | 62.7 (3.6) | 3.1 (0.1) | 26.1 (1.9) | 23.9 (0.7) | 1.34 (0.05) | 9.5 (0.8) | 8.3 (0.4) | 53.0 (1.3) |
| leaco1$_{-0.821kb}$-IPT | N45 | 64.1 (3.8) | 2.9 (0.5) | 38.4 (2.4) | 21.8 (0.5) | 1.05 (0.03) | 16.4 (2.0) | 14.1 (1.6) | 56.6 (1.3) |
| leaco1$_{-0.821kb}$-IPT | N47 | 65.7 (2.8) | 3.0 (0.2) | 26.5 (1.4) | 26.8 (0.5) | 1.36 (0.02) | 11.4 (0.8) | 9.0 (0.7) | 54.4 (0.4) |
| leaco1$_{-0.821kb}$-IPT | N48 | 65.8 (3.5) | 2.8 (0.2) | 30.9 (2.5) | 21.6 (0.3) | 1.07 (0.02) | 14.9 (1.4) | 11.4 (0.8) | 51.4 (0.6) |
| leaco1$_{-0.821kb}$-IPT | N49 | 59.7 (3.7) | 2.9 (0.1) | 28.0 (2.2) | 21.6 (0.3) | 1.08 (0.02) | 11.5 (1.1) | 9.9 (0.8) | 52.4 (0.9) |
| leaco1$_{-0.821kb}$-IPT | N50 | 57.1 (3.5) | 2.3 (0.2) | 31.0 (2.2) | 21.8 (0.4) | 1.08 (0.03) | 16.5 (0.8) | 14.0 (0.9) | 55.3 (0.6) |
| leaco1$_{-0.821kb}$-IPT | N52 | 59.4 (3.5) | 3.1 (0.2) | 22.0 (1.7) | 17.7 (0.4) | 0.96 (0.02) | 8.3 (0.7) | 7.1 (0.4) | 52.4 (0.3) |
| Statistical Effects | | | | | P-values | | | | | |
| Between lines | | $P \leq 0.0001$ | $P \leq 0.0001$ | $P \leq 0.0001$ | $P \leq 0.0001$ | $P \leq 0.0001$ | $P \leq 0.0001$ | $P \leq 0.0001$ | $P \leq 0.0001$ |
| | | | | F-value (critical F-value = 1.55) | | | | | |
| df(between lines) = 26 Total df = 215 | | 12.5 | 29.0 | 150.3 | 34.5 | 20.8 | 79.6 | 70.1 | 17.3 |

Example 3

Figure 11:
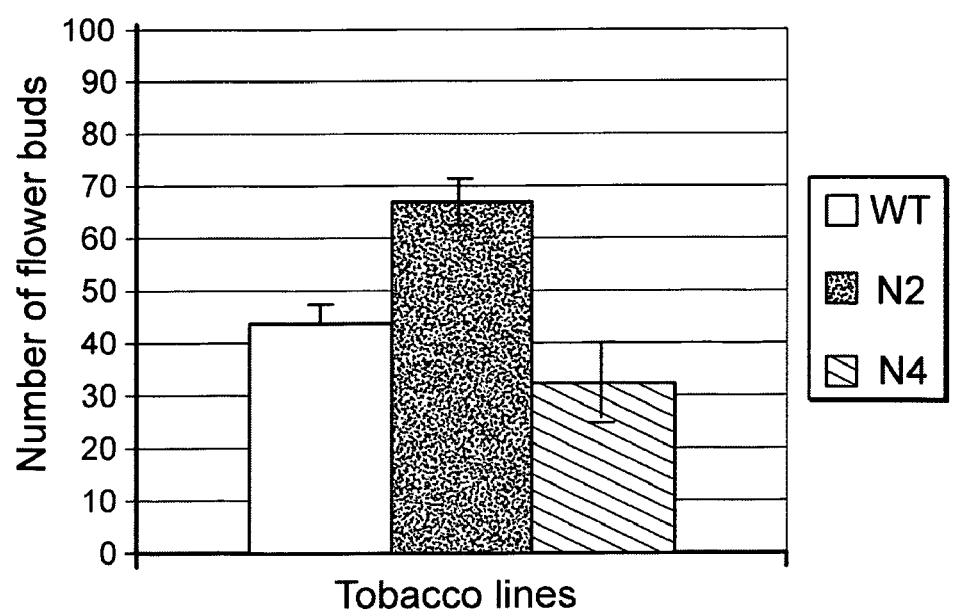
FIG. 11. Flower bud number in tobacco wild-type and LEACO1$_{0.821\ kb}$-ipt transgenic lines N2 and N4 (T$_2$ generation).

Stability of tobacco transformants. The stability of the transgene in the first ($T_1$) and second ($T_2$) seed-generations of tobacco was assessed. Results are shown in Table 3 for the $T_1$-generation & in FIG. 11 for the $T_2$-generation. Basically, the phenotype observed in the primary transformant was also observed in the seed generations.

$T_1$ generation LEACO1$_{0.821\ kb}$-ipt tobacco lines displayed growth habits that could be separated into one of two distinct phenotypic groups. One transgenic line from each group was selected to characterize these two basic phenotypes (Table 3). One phenotype, typified by LEACO1$_{0.821\ kb}$-ipt lines N2 and N8, appeared similar to the wild type in overall stature and branching habit but produced a greater number of flower buds (Table 3 and FIG. 13).

The tobacco phenotype, typified by LEACO1$_{0.821\ kb}$-ipt lines N1 and N4, displayed a more compact branching habit with fewer flower buds than either the wild type line or the transgenic lines (N2 and N8) (Table 3 and FIG. 13). Southern hybridization analysis of genomic DNA digested with HindIII confirmed the integration of the ipt gene into the genome of the $T_1$ transgenic lines that exhibited distinct phenotypic characteristics, while no signals was detected in the wild type plants (FIG. 4C).

The increase in flower bud initiation associated with one LEACO1$_{0.821\ kb}$-ipt phenotype was found to be stable in successive seed generations. For example, the trend toward increased flower bud numbers in transgenic line N2 also was observed in the $T_2$ seed generation. In a separate experiment, the average number of flowers per plant in the wild type was 44±3.1. In comparison, transgenic tobacco plants of the $T_2$ generation averaged from 84.5±6.4 flowers per plant in line N2 to only 34.3±5.5 flowers per plant in line N4.

In chrysanthemum the primary means of propagation is asexual through the use of vegetative shoot tip cuttings. A wide range of flower bud increases were observed with transgenic plants producing flower bud counts ranging 109% of the wild-type to up to 998% of the wild-type. The observed increases in bud number were consistent in repeated growth chamber and greenhouse studies. Phenotypic differences were correlated with the level of ipt expression in each transgenic line (FIG. 16). The studies were conducted with plants that were asexually propagated from the primary transformant (parent plant).

Figure 7:
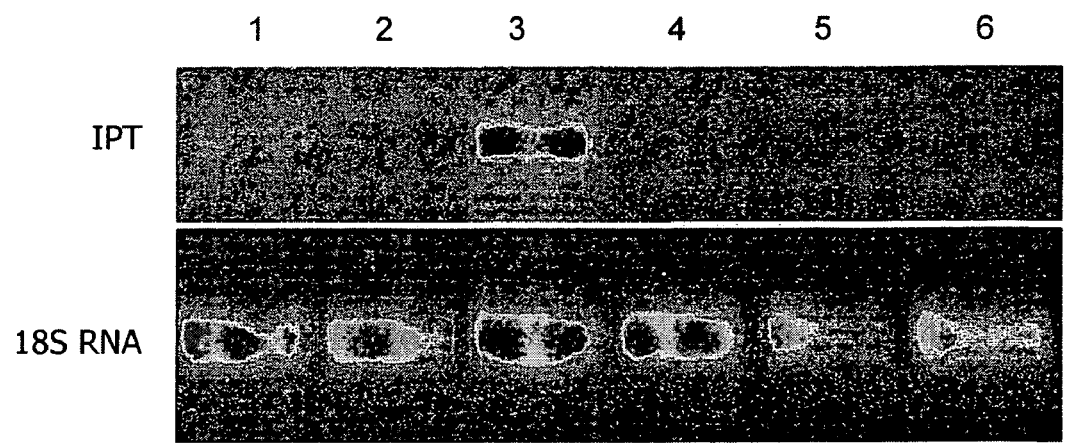
FIG. 7. Ethephon suppressed ipt expression in $LEACO1_{0.821\ kb}$-ipt tobacco lines. RT-PCR analysis was used to detect changes in ipt expression in transgenic lines after treatment with the ethylene-generating compound ethephon. Lane 1: $LEACO1_{0.821\ kb}$-ipt (line N2) without ethephon treatment; Lane 2: $LEACO1_{0.821\ kb}$-ipt (line N2) 24 h after ethephon treatment; Lane 3: $LEACO1_{0.821\ kb}$-ipt (line N4) without ethephon treatment; Lane 4: $LEACO1_{0.821\ kb}$-ipt (line N4) 24 h after ethephon treatment; Lane 5: wild type tobacco without ethephon treatment; Lane 6: wild type tobacco 24 h after ethephon treatment.

RT-PCR analysis with total RNAs extracted from the leaves of wild type and transgenic lines N2 and N4 growing under normal glasshouse conditions, and the same lines treated with the ethylene-releasing compound ethephon, showed differential levels of expression (FIG. 7). The 0.52 fragment of the ipt cDNA derived from mRNA was amplified in both transgenic lines under normal greenhouse conditions but the level of expression was much higher in the line (N4) that showed the more extreme cytokinin phenotype. Gene expression was not detected in wild type plants or in transgenic lines sprayed with ethephon (500 mg/L). These data demonstrate that the range of phenotypes observed in the various LEACO1$_{0.821\ kb}$-ipt tobacco lines corresponded with the level of ipt expression and that ipt expression could be suppressed by exogenous application of ethephon. A similar response was noted in transgenic chrysanthemum plants exposed to an ethephon spray.

Although both petunia and chrysanthemum were transformed with the LEACO1$_{0.821\ kb}$-ipt gene, seed generation plants were not assessed. The cultivar lines used to transform in these crops were sterile, asexually propagated lines (this is typical of many ornamental plants). Seed production is possible but requires a special long period of time. With many ornamental crops, once a commercially valuable phenotype is identified, the individual line is propagated asexually.

Example 4

Establishment and molecular analysis of transgenic plants of *Nicotiana tabacum* harboring the LEACO1$_{0.821\ kb}$-ipt and LEACO1$_{0.821\ kb}$-gus fragments. The ipt gene positioned under the transcriptional control of a 0.821 kb fragment of LEACO1 promoter was introduced to wild-type tobacco plants by *Agrobacterium* transformation. More than 30 kanamycin-resistant, putative transformants were regenerated, transferred to pots and successfully acclimated to glasshouse conditions.

Figure 4A:
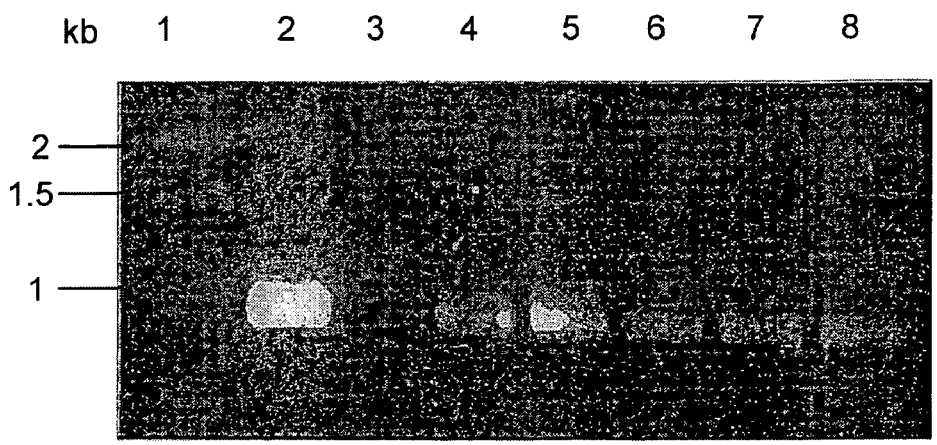
FIG. 4. PCR analysis of putative transgenic $LEACO1_{0.821\ kb}$-ipt tobacco plants and Southern blot analysis of genomic DNA isolated from tobacco plants. As expected, transgenic plants carried the 0.918 kb fragment comprised of the 0.821 kb LEACO1 promoter plus the 97 bp UTR leader sequence (A) and also showed a 0.52 kb fragment of the ipt gene (B). Lane 1: 1-kb ladder; Lane 2: Positive control (plasmid $LEACO1_{0.821\ kb}$-ipt-nos); Lane 3: Negative control (wild type tobacco); Lanes 4-8: Putative transgenic tobacco lines. Southern blot analysis (C) of genomic DNA isolated from the wild type tobacco and $LEACO1_{0.821\ kb}$-ipt transgenic tobacco lines ($T_1$ generation) representing both of the distinct phenotypic groups. The DIG-labeled 0.52 kb fragment of the ipt gene from $LEACO1_{0.821\ kb}$-ipt-nos plasmid DNA was used as a probe. Two copies of the ipt gene were detected in some lines (such as N1 and N4, in lanes 2 and 3 respectively) while a single copy of the gene was detected in other lines that produced a distinct phenotypic characteristic (lines N2 and N8 in lanes 4 and 5 respectively). Non-transformed wild type *Nicotiana tabacum* DNA (Lane 1) served as a negative control and the ipt fragment was not detected. Plasmid DNA was used as a positive control (Lane 6).
Figure 4B:
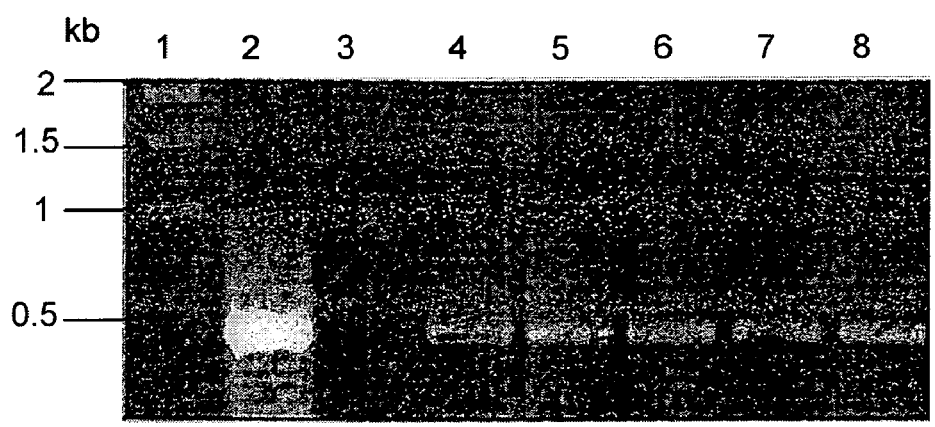
Figure 4C:
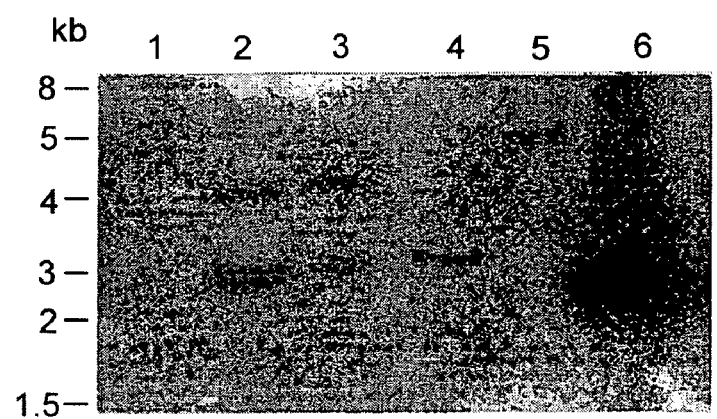
Figure 5:
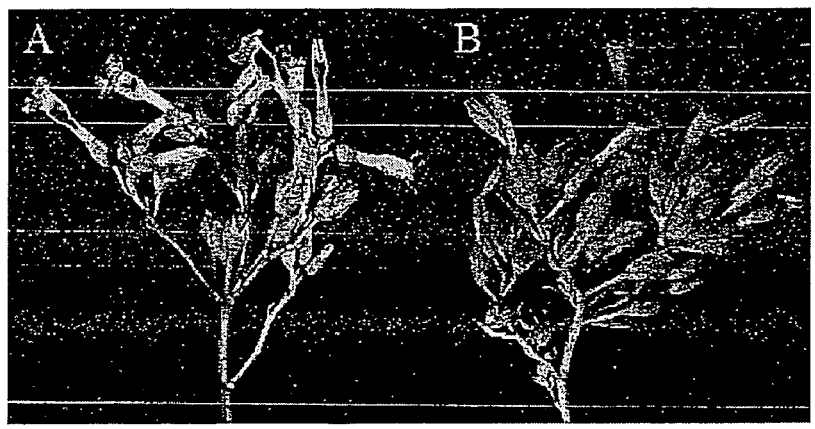
FIG. 5. Number of flower buds in wild-type (FIG. 5A) and transformed by the $LEACO1_{0.821\ kb}$ construct (FIG. 5B) in tobacco plants.
Figure 6:
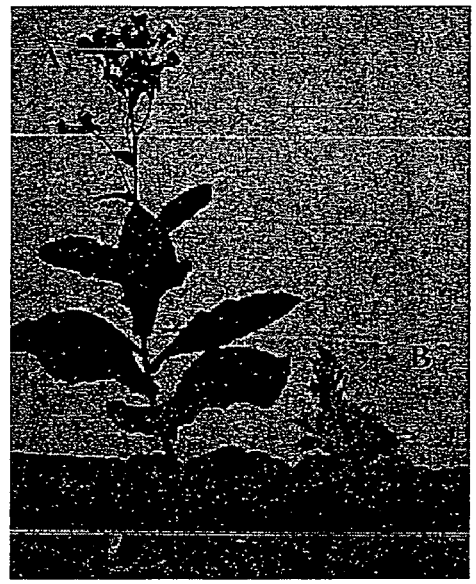
FIG. 6. Phenomic responses observed in tobacco plants containing the ipt gene under control of the $LEACO1_{0.821\ kb}$ promoter varied widely. Plant N1 (FIG. 6A) displayed normal growth habit with increased flower bud number when compared with wild-type plants. Plant N4 (FIG. 6B) is the more extreme phenotype observed when transgenic lines contained multiple copies of the transgene or overexpressed the ipt gene. In chrysanthemum, phenotype of $LEACO1_{0.821\ kb}$-ipt plants also varied widely but, unlike tobacco, many very highly desirable plant forms were observed.

PCR analysis confirmed the integration of the foreign gene into the genome of the putative transgenic tobacco plants (FIG. 4A-B). PCR amplifications produced the expected 0.918 kb fragment of 0.821 kb LEACO1 promoter plus the 97 bp UTR leader sequence (FIG. 4A) and a 0.52 kb fragment of the ipt gene (FIG. 4B) from both the putative transgenic lines and the plasmid DNA used as a positive control. DNA was not detected in non-transgenic wild type plants. Ten kanamycin-resistant LEACO1$_{0.821\ kb}$-gus plants were also confirmed positive for the presence of the LEACO1$_{0.821\ kb}$ promoter by PCR and stained positive in the gus histochemical assay. Over 50 transgenic lines of LEACO1$_{0.821\ kb}$-ipt chrysanthemum were also produced and tested for flowering and reproductive growth characteristics.

Example 5

GUS expression under the control of the LEACO1$_{0.821\ kb}$ promoter. LEACO1$_{0.821\ kb}$-gus tobacco seedlings were used to assess the effects of endogenous auxin and ethylene pathway activity on LEACO1$_{0.821\ kb}$-controlled gene regulation. Under glasshouse conditions, gus activity was found in leaves and stems of young LEACO1$_{0.821\ kb}$-gus (line N5) tobacco seedlings (FIG. 14A). No gus activity was observed in roots of plants from the same line.

To assess the involvement of auxin and ethylene in inducing the LEACO1$_{0.821\ kb}$ promoter, IAA, AOA, ACC, or ethephon was applied to plants with the apical buds either intact or removed (FIG. 14 B-D). Intact apical buds produce endogenous IAA but shoots with excised apical buds do not. With apical buds intact, plants showed increased gus gene expression while shoots with the apical bud removed showed reduced gus expression (FIG. 14). However, shoots with the apical bud removed showed evidence of gus gene expression when exposed to exogenously IAA applied in a lanolin paste but not when IAA was applied together with the auxin transport inhibitor TIBA.

The ethylene biosynthesis inhibitor AOA also inhibited gus gene expression. These results suggest involvement of both auxin and ethylene in stimulating LEACO1$_{0.821\ kb}$ promoter activity.

In an ensuing experiment, young LEACO1$_{0.821\ kb}$-gus seedlings (line N3 and line N5) were treated with a spray of either AOA, ethephon, or the ethylene precursor ACC, or lanolin containing TIBA (FIG. 14. C, D). In plants with intact apical buds, gus expression was inhibited by both TIBA and AOA. But intact shoots exposed to ethephon continued to show gene expression. Seedlings with apical buds removed showed a lower level of gus gene expression compare with plants with intact apical buds but gus expression in plants with excised apical buds was stimulated by the ethylene precursor ACC.

Example 6

Figure 8:
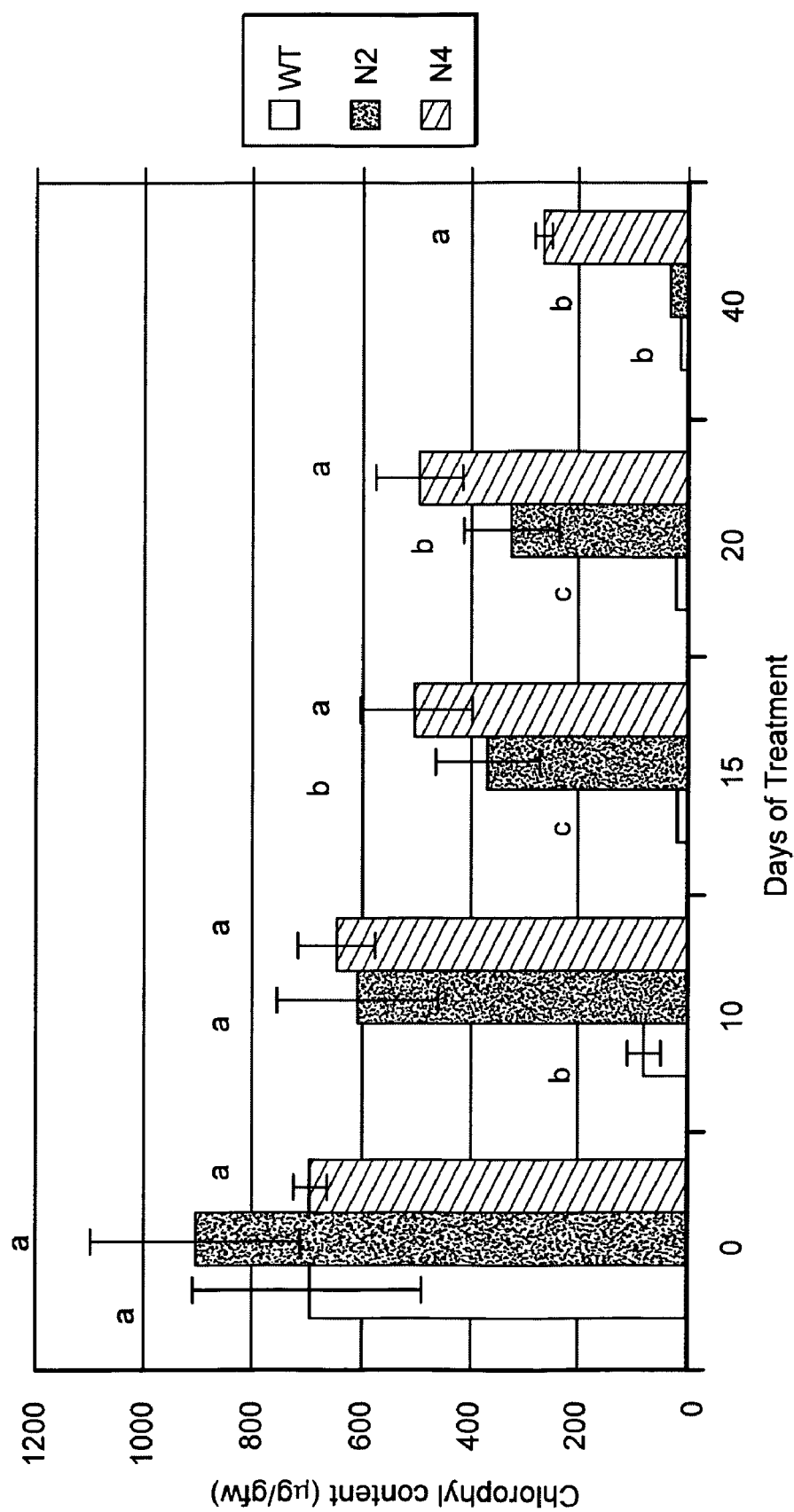
FIG. 8. Excised leaves of LEACO1$_{0.821\ kb}$-ipt tobacco lines showed delayed senescence under prolonged dark conditions. Leaves from wild type tobacco (cv. Havana) and LEACO1$_{0.821\ kb}$-ipt transgenic lines were detached, plated onto wet filter paper, and stored in the dark at 25° C. The chlorophyll content (□g/g FW) was measured immediately after leaves were detached and then periodically over a 40-day period. Chlorophyll in wild type leaves declined rapidly during the first 10-day period, but in leaves from LEACO1$_{0.821\ kb}$-ipt plants, 50% of the initial chlorophyll concentration remained after 20 days in the dark. Leaves from the LEACO1$_{0.821\ kb}$-ipt line that showed the highest ipt expression levels (N4) retained 30% of initial chlorophyll levels for up to 40 days. Means at each sample date labeled with the same letters are not significantly different according to Tukey's multiple comparison test with a family error rate of 0.05.
Figure 9:
FIG. 9. Branching and flower bud count differed markedly for wild-type and LEACO1$_{0.821\ kb}$-ipt chrysanthemum plants.
Figure 10:
FIG. 10. Bud count on LEACO1$_{0.821\ kb}$-ipt (#5 left) was nearly 7-times higher than on wild-type plants (right) grown under similar conditions. LEACO1$_{1.821\ kb}$-ipt (#1) and LEACO1$_{0.821\ kb}$-ipt (#14) are shown between the wild-type and LEACO1$_{0.821}$ kb-ipt (#5). In a following study that included additional transgenic lines, bud count on LEACO1$_{0.821\ kb}$-ipt (#16) averaged 10-times higher than the wild-type.

Leaf senescence in LEACO1$_{0.821\ kb}$-ipt transgenic tobacco. Leaf senescence was dramatically delayed in LEACO1$_{0.821\ kb}$-ipt transgenic plants compared to wild type tobacco plants (FIG. 8). Excised leaves from wild type tobacco and transgenic lines N2 and N4 were stored under dark conditions (25° C.) for up to 40 days. Chlorophyll content in non-transgenic wild type leaves declined to less than 5% of the initial concentration after the 10$^{th}$ day of dark storage and disappeared completely by the 15$^{th}$ day. Leaves of transgenic lines showed tolerance to dark storage and maintained approximately 50% of the initial chlorophyll concentrations after 20 days in the dark. Leaves from LEACO1$_{0.8218b}$-ipt line N4 retained approximately 25% of the initial chlorophyll concentrations for up to 40 days in the dark. Resistance to leaf senescence appeared to be positively correlated with differences in ipt gene expression.

REFERENCES

U.S. Pat. No. 6,204,437 (Mar. 20, 2001)

S. Gan and R. M. Amasino, Making sense of senescence: Molecular genetic regulation and manipulation of leaf senescence, *Plant Physiology.* 113 (1997) 313-319.

Coenen C, Christian M, Lüthen H, Lomax T L. (2003). Cytokinin Inhibits a Subset of Diageotropica-Dependent Primary Auxin Responses in Tomato. Plant Physiol. 131: 1692-1704

Coenen C, Lomax T L (1998) The DIAGEOTROPICA gene differentially affects auxin and cytokinin responses throughout development in tomato (*Lycopersicon esculentum* Mill.). Plant Physiol 117: 63-72

Vendrell M, McGlasson W B (1971) Inhibition of ethylene production in banana fruit tissue by ethylene treatment. Aust J Biol Sci 24:885-895

Riov J, Yang F (1982) Autoinhibition of ethylene production in citrus peel discs. Plant Physiol 69:687-690

Yoshii H, Imaseki H. (1982). Regulation of auxin-induced ethylene biosynthesis repression of inductive formation of 1-aminocyclopropane-1-carb oxylate synthase by ethylene. Plant Cell Physiol. 23:639-649.

Kim J H, Kim W T, Kang B G. (2001). *IAA and N$^6$-benzyladenine inhibit ethylene regulated expression of ACC oxidase and ACC synthase genes in mungbean hypocotyls.* Plant Cell Physiol. 42(10:1056-1061.

Zauberman G, Fuchs Y (1973). Ripening processes in avocado stored in ethylene atmosphere in cold storage. J Amer Soc Hort Sci 98: 477-480.

Zeroni M, Galil J (1976) Autoinhibition of ethylene formation in nonripening stages of the fruit of sycomore fig (*Ficus sycomorus* L.). Plant Physiol 57:645-650.

T. H. Boyle, BA influence flowering and dry-matter partitioning in shoots of 'Crimson Giant' Easter Cactus, *HortScience* 30 (1995) 289-291.

Mariya Khodakovskaya•Degang Zhao•William Smith•Yi Li••Richard McAvoy (2006). Expression of ipt gene controlled by an ethylene and auxin responsive fragment of the LEACO1 promoter increases flower number in transgenic *Nicotiana tabacum*. Plant Cell Reports: (In Press, accepted May 4, 2006).

Lau O L, John W W, Yang S F. (1977). Effect of different cytokinins on ethylene production in mung bean hypocotyls in the presence of indole-3-acetic acid or calcium ion. Plant Physiol. 39:1-3.

Liu J H, Lee-Tamon S H, Reid D M. (1997). Differential and wound-inducible expression of 1-aminocyclopropane-1-carboxylate oxidase genes in sunflower seedlings. Plant Mol. Biol. 34:923-933.

C. M. Smart, S. R. Scotfield, M. W. Bevan, and T. A. Dyer, Delayed senesce in tobacco plants transformed with tmr, a gene for cytokinin production in *Agrobacterium*. *Plant Cell.* 3 (1991) 646-656.

Y. Li, G. Gagen and T. J. Guilfoyle, Altered morphology in transgenic tobacco plants that overproduce cytokinins in specific tissues and organs. *Developmental Biology.* 153 (1992) 386-395.

A. Goldsgrough, H. Albrecht, and R. Stratford, Salicylic acid-inducible binding of a tobacco nuclear protein to a 10 bp sequence is highly conserved amongst stress-inducible genes. *Plant J.* 3 (1993) 583-571.

H. Itzhaki, J. M. Maxson, and W. R. Woodson, An ethylene-responsive enhancer element is involved in the senescence-related expression of the carnation glutathione-S-transferase (GST1) gene. *Proc. Natl. Acad. Sci.* 91 (1994) 8925-8929.

J. Montgomery, S. Goldman, J. Deikman, L. Margossian, and R. L. Fischer, Identification of an ethylene-responsive region in the promoter of a fruit ripening gene. *Proc. Natl. Acad. Sci.* 90 (1993) 5939-5943.

B. Blume, C. S. Barry, A. J. Hamilton, M. Bouzayen, D. Griegson, Identification of transposon-like elements in noncoding regions of tomato ACC oxidase genes. *Mol. Gen. Genet.* 254 (1997) 297-303.

X. Tang, A. M. T. R. Gomes, A. Bhatia, W. R. Woodson, Organization and structure of the 1-aminocyclopropane-1-carboxylate oxidase gene family from *Petunia hybrida*. *Plant. Mol. Biol.* 23 (1993) 1151-1164.

L. Alexander and D. Grierson. Ethylene biosynthesis and action in tomato: a model for climacteric fruit ripening. *J. Exp Bot.* 53 (2002) 377: 2039-2055.

Norcini, Jeffrey G., William G. Hudson, Melvin P. Garber, Ronald K. Jones, Ann R. Chase, and Kane Bondari. Pest management in the U.S. greenhouse and nursery industry: III. Plant Growth Regulation. *HortTechnology* 6 (1996) 3: 207-210.

Khodakovskaya, Mariya, Yi Li, Jisheng Li, Radomíra Vañková, Jiří Malbeck and Richard McAvoy. Effects of cor15a-IPT Gene Expression on Leaf Senescence in Transgenic *Petunia×hybrida* and *Dendranthema×grandiflorum*. *Journal of Experimental Botany.* 56 (2005) 414: 1165-1175.

D. E. Akiyoshi, H. Klee, R. M. Amasino, E. W. Nester, M. P. Gordon, T-DNA of *Agrobacterium tumefaciens* encodes an enzyme of cytokinin biosynthesis. *Proceedings of the National Academy of Sciences*, USA. (1984) 81: 5994-5998.

B. Blume, D. Grierson, Expression of ACC oxidase promoter-GUS fusions in tomato and *Nicotiana plumbaginifolia* regulated by developmental and environmental stimuli. *Plant J.* 12 (1997) 731-746.

R. W. Mercier, Apoplastic invertase: a dissection of its role in photosynthate translocation and partitioning, *Cell Biology Thesis, Ph.D.* University of Connecticut. (1998).

T. H. Boyle, BA influence flowering and dry-matter partitioning in shoots of 'Crimson Giant' Easter Cactus. *HortScience.* 30 (1995) 289-291.

S. Gan, R. M. Amasino, Making sense of senescence: Molecular genetic regulation and manipulation of leaf senescence. *Plant Physiology.* 113 (1997) 313-319.

W. M. Ainley, K. J. McNeil, J. W. Hill, W. L. Lingle, R. B. Simpson, M. L. Brenner, R. T. Nagao, J. L. Key, Regulatable endogenous production of cytokinins up to "toxic" levels in transgenic plants and plant tissues. *Plant. Mol. Biol.* 22 (1993) 13-24.

Y. Li, G. Hagen, T. J. Guilfoyle, Altered morphology in transgenic tobacco plants that overproduce cytokinins in specific tissues and organs, *Developmental Biology.* 153 (1992) 386-395.

C. S. Barry, B. Blume, M. Bouzayen, W. Cooper, A. Hamilton, D. Griegson, Differential expression of the 1-aminocyclopropane-1-carboxylate oxidase gene family of tomato. *Plant J.* 9 (1996) 525-535.

J. P. Vogel, K. E. Woeste, A. Thelogis, J. J. Kieber, Recessive and dominant mutations in the ethylene biosynthetic gene ACS5 of *Arabidopsis* confer cytokinin insensitivity and ethylene overproduction, respectively. *Proc. National Acad. Sci.* 95 (1998a) 4766-4771.

J. P. Vogel, P. Schuerman, K. Woeste, I. Brandstatter, J. L. Kieber, Isolation and characterization of *Arabidopsis* mutants defective in the induction of ethylene biosynthesis by cytokinin. *Genetics.* 149 (1998b) 417-427.

Gan S, Amasino R M, Inhibition of leaf senescence by autoregulated production of cytokinin. *Science.* 270 (1995) 1986-1988.

Guilfoyle, T J, Ulmasov T, and Hagen G. (1998) The ARF family of transcription factors and their role in plant hormone-responsive transcription. Cell. Mol. Life Sci. 54:619-627.

Hong J C, Cheong Y H, Nagao R T, Bahk J D, Key J L, Cho M J. (1995) Isolation of two soybean G-box binding factors which interact with a G-box sequence of the auxin responsive gene. The Plant J. 8(2): 199-211.

Murashige, F. and Skoog, A., A revised medium for rapid growth and bioassays with tobacco tissue cultures. *Physiol. Plant* 15 (1962) 473-497.

Remington D L, Vision T J, Guilfoyle, T J, Reed J W. (2004) Contrasting modes of diversification in the Aux/IAA and ARF gene families. Plant Physiol. 135:1738-1752.

G. An, B. D. Watson, C. C. Chiang, Transformation of tobacco, tomato, potato and *Arabidopsis thaliana* using a binary Ti vector system. *Plant Physiol.* 81 (1988) 301-305.

Ulmasov T, Liu Z-B, Hagen G, Guilfoyle T J. (1995) Composite structure of auxin response elements. The Plant Cell 7:1611-1623.

Ulmasov T, Hagen G, Guilfoyle T J. (1997) ARF1, a transcription factor that binds to auxin response elements. Science 276:1865-1868.

Ulmasov T, Hagen G, Guilfoyle T J. (1999a) Activation and repression of transcription by auxin-response factors. Proc. Natl. Acad. Sci. 96:5844-5849.

Ulmasov T, Hagen G, Guilfoyle T J. (1999b) Dimerization and DNA binding of auxin response factors. The Plant J. 19(3):309-319.

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer -continued

```
<400> SEQUENCE: 1
ggttgagttg tttccctctg                                                 20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtaaagtgt tttcctaagt g                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtccaactt gcacaggaaa g                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcttgccta ctggaagctt a                                               21

<210> SEQ ID NO 5
<211> LENGTH: 723
<212> TYPE: DNA
<213> ORGANISM: Agrobacterium tumefaciens

<400> SEQUENCE: 5
atggatctgc gtctaatttt cggtccaact tgcacaggaa agacgtcgac cgcggtagct      60
cttgcccagc agactgggct tccagtcctt tcgctcgatc gggtccaatg ttgtcctcag     120
ctgtcaaccg gaagcggacg accaacagtg gaagaactga aggaacgag ccgtctatac      180 cttgatgatc ggcctctggt gaagggtatc atcgcagcca agcaagctca tgaaaggctg     240 atggggagg tgtataatta tgaggcccac ggcgggctta ttcttgaggg aggatctatc     300
tcgttgctca agtgcatggc gcaaagcagt tattggagtg cggattttcg ttggcatatt     360
attcgccacg agttagcaca cgaggagacc ttcatgaacg tggccaaggc cagagttaag     420
cagatgttac gccccgcttc aggcctttct attatccaag agttggttga tctttggaaa     480
gagcctcggc tgaggcgcat actgaaagag atcgatggat atcgatatgc catgttgttt     540
gttagccaga accagatcac atccgatatg ctattgcagc ttgacgcaga tatggaggat     600
aagttgattc atgggatcgc tcaggagtat ctcatccatg cacgccgaca agaacagaaa     660
ttccctcgag ttaacgcagc cgcttacgac ggattcgaag gtcatccatt cggaatgtat     720
tag                                                                   723

<210> SEQ ID NO 6
```

<211> LENGTH: 821
<212> TYPE: DNA
<213> ORGANISM: Lycopersicon esculentum

<400> SEQUENCE: 6

```
gtgaacctct catgtattcc gagtgaattg gttgaggttg tttccctctg tattttgtac      60
tctcatgttt atagtggatt gctcatttcc tttgtggacg taggtcgatt gaccgaacca     120
cgttaaatct ttgtgtcttt tggtatattt ctcgttgtct tcttactcgt ggtctttcga     180
ggtttgcttt gctagcttcc gcgtttacac ctgcttattt gcggtcctaa cagagttcga     240
tgggttgaat ctataaaaag aaaaatatac tcgtgattca cgattattta tatgaaaata     300
taataaatat tgaatttcct ttgctatttc ttatgtttac gtctttatat ttcaaattat     360
tccaccaata ctgacaagcc ctaggccatc tctaggaaat tcatacaatt ttttttttgt     420
tgttaactag ttaaattggc agccttaaag attattgtaa aattcaaggc aacttcctca     480
agtactacaa ctacattgta acatcccagt caaagtgtcc taaaattta taaaatttga      540
cacatgaaac aatagcacaa taaattttag tactattgca gccatggccc ataagccatc     600
atgtattata gtcaaaatgg gtccttttcc aatttgtctt gatcccaaaa tcccttgta      660
ggtaagatgg ttcaacaagg aactatgact cttaaggtag acttggactc atagacttgt     720
cataactcat aaagacttgg aatataataa ttattcattt aaattataat tctctacttt     780
aatatcttct actataaata ccctttcaaa gcctcattat t                         821
```

<210> SEQ ID NO 7
<211> LENGTH: 918
<212> TYPE: DNA
<213> ORGANISM: Lycopersicon esculentum

<400> SEQUENCE: 7

```
gtgaacctct catgtattcc gagtgaattg gttgaggttg tttccctctg tattttgtac      60
tctcatgttt atagtggatt gctcatttcc tttgtggacg taggtcgatt gaccgaacca     120
cgttaaatct ttgtgtcttt tggtatattt ctcgttgtct tcttactcgt ggtctttcga     180
ggtttgcttt gctagcttcc gcgtttacac ctgcttattt gcggtcctaa cagagttcga     240
tgggttgaat ctataaaaag aaaaatatac tcgtgattca cgattattta tatgaaaata     300
taataaatat tgaatttcct ttgctatttc ttatgtttac gtctttatat ttcaaattat     360
tccaccaata ctgacaagcc ctaggccatc tctaggaaat tcatacaatt ttttttttgt     420
tgttaactag ttaaattggc agccttaaag attattgtaa aattcaaggc aacttcctca     480
agtactacaa ctacattgta acatcccagt caaagtgtcc taaaattta taaaatttga      540
cacatgaaac aatagcacaa taaattttag tactattgca gccatggccc ataagccatc     600
atgtattata gtcaaaatgg gtccttttcc aatttgtctt gatcccaaaa tcccttgta      660
ggtaagatgg ttcaacaagg aactatgact cttaaggtag acttggactc atagacttgt     720
cataactcat aaagacttgg aatataataa ttattcattt aaattataat tctctacttt     780
aatatcttct actataaata ccctttcaaa gcctcattat ttgtacatca acattgata      840
ttcatctctt caatcttttg tattcacata ttctatttat tcaatacact taggaaaaca     900
ctttaccaag aaattaag                                                   918
```

<210> SEQ ID NO 8
<211> LENGTH: 1921
<212> TYPE: DNA
<213> ORGANISM: Artificial Sequence
<220> FEATURE:
<223> OTHER INFORMATION: Description of Artificial Sequence: Synthetic
      gene construct

<400> SEQUENCE: 8

| | | | | | |
|---|---|---|---|---|---|
| aagcttgtga | acctctcatg | tattccgagt | gaattggttg | aggttgtttc | cctctgtatt | 60 |
| ttgtactctc | atgtttatag | tggattgctc | atttcctttg | tggacgtagg | tcgattgacc | 120 |
| gaaccacgtt | aaatctttgt | gtcttttggt | atatttctcg | ttgtcttctt | actcgtggtc | 180 |
| tttcgaggtt | tgctttgcta | gcttccgcgt | ttacacctgc | ttatttgcgg | tcctaacaga | 240 |
| gttcgatggg | ttgaatctat | aaaaagaaaa | atatactcgt | gattcacgat | tatttatatg | 300 |
| aaaatataat | aaatattgaa | tttcctttgc | tatttcttat | gtttacgtct | ttatatttca | 360 |
| aattattcca | ccaatactga | caagccctag | gccatctcta | ggaaattcat | acaatttttt | 420 |
| ttttgttgtt | aactagttaa | attggcagcc | ttaaagatta | ttgtaaaatt | caaggcaact | 480 |
| tcctcaagta | ctacaactac | attgtaacat | cccagtcaaa | gtgtcctaaa | attttataaa | 540 |
| atttgacaca | tgaaacaata | gcacaataaa | ttttagtact | attgcagcca | tggcccataa | 600 |
| gccatcatgt | attatagtca | aaatgggtcc | ttttccaatt | tgtcttgatc | ccaaaatccc | 660 |
| tttgtaggta | agatggttca | acaaggaact | atgactctta | aggtagactt | ggactcatag | 720 |
| acttgtcata | actcataaag | acttggaata | taataattat | tcatttaaat | tataattctc | 780 |
| tactttaata | tcttctacta | taaatacctt | ttcaaagcct | cattatttgt | acatcaaaca | 840 |
| ttgatattca | tctcttcaat | cttttgtatt | cacatattct | atttattcaa | tacacttagg | 900 |
| aaaacacttt | accaagaaat | taaggtcgac | atggatctgc | gtctaatttt | cggtccaact | 960 |
| tgcacaggaa | agacgtcgac | cgcggtagct | cttgcccagc | agactgggct | tccagtcctt | 1020 |
| tcgctcgatc | gggtccaatg | ttgtcctcag | ctgtcaaccg | gaagcggacg | accaacagtg | 1080 |
| gaagaactga | aaggaacgag | ccgtctatac | cttgatgatc | ggcctctggt | gaagggtatc | 1140 |
| atcgcagcca | agcaagctca | tgaaaggctg | atggggagg | tgtataatta | tgaggcccac | 1200 |
| ggcgggctta | ttcttgaggg | aggatctatc | tcgttgctca | agtgcatggc | gcaaagcagt | 1260 |
| tattggagtg | cggattttcg | ttggcatatt | attcgccacg | agttagcaca | cgaggagacc | 1320 |
| ttcatgaacg | tggccaaggc | cagagttaag | cagatgttac | gccccgcttc | aggccttttct | 1380 |
| attatccaag | agttggttga | tctttggaaa | gagcctcggc | tgaggcgcat | actgaaagag | 1440 |
| atcgatggat | atcgatatgc | catgttgttt | gttagccaga | accagatcac | atccgatatg | 1500 |
| ctattgcagc | ttgacgcaga | tatggaggat | aagttgattc | atgggatcgc | tcaggagtat | 1560 |
| ctcatccatg | cacgccgaca | agaacagaaa | ttccctcgag | ttaacgcagc | cgcttacgac | 1620 |
| ggattcgaag | gtcatccatt | cggaatgtat | taggagctcc | ccgatctagt | aacatagatg | 1680 |
| acaccgcgcg | cgataattta | tcctagtttg | cgcgctatat | tttgttttct | atcgcgtatt | 1740 |
| aaatgtataa | ttgcgggact | ctaatcataa | aaacccatct | cataaataac | gtcatgcatt | 1800 |
| acatgttaat | tattacatgc | ttaacgtaat | tcaacagaaa | ttatatgata | atcatcgcaa | 1860 |
| gaccggcaac | aggattcaat | cttaagaaac | tttattgcca | aatgtttgaa | cgatcgaatt | 1920 |
| c | | | | | | 1921 |

<210> SEQ ID NO 9
<211> LENGTH: 3681
<212> TYPE: DNA
<213> ORGANISM: Lycopersicon esculentum

<400> SEQUENCE: 9

-continued

```
aaatttgata gattcagttt ttatgttttt agtgctgatt acaacattga aattctaaat      60
ttagaattta atatttatta aatgttagtg catttataca aataacatat tacatctcaa     120
ataatattga gtttgttaga ttttatttgc cctgatttct tatcataaat aggttttcct     180
tttaggaaaa ggttttgaat tgactattct ttttttggta ggaaaaagtt taggactcta     240
taaatagagg catgttcctt ctaacttaat tagcattcac aatgtagttt taagggcttt     300
gagagttttg gttagaggga aatttgtga acctctcatg tattccgagt gaattggttg      360
aggttgtttc cctctgtatt ttgtactctc atgtttatag tggattgctc atttcctttg    420
tggacgtagg tcgattgacc gaaccacgtt aaattttgt gtcttttggt atatttcctg     480
ttcttcttac tcgtggtctt tcgaggtttg ctttgctagc ttccgcgttt acacctgctt    540
attttcggtc ctaacaagtg gtatcagagc cagattcaat aatggagtca ggtgtagtgg    600
ttcgataatc gatgattgaa ccaagttaga aagaggtgtt catcttgacg ggtgtagttc   660
tagccgcaac cttttttgaca gtaatgaaga ttttgatgga gaaattgttt cagagaggtt  720
ctctgtgttg agacataaat tttgtaaagg agattatgga gaggagaagc aagttgttga    780
agattaagta aagaaggtgg acaaatctat tttgtcagaa attcaggcca aggggggagat   840 ttgttgggtt ttatttgccc tgattttta ccataaatag gttttccttt aaggaaaagg    900
ttttgaattg actattcttt ttttggtagg aaaaggttta ggattctata aatagaggca    960
tgttccttct aacttaatta gcattcacaa tgtagtttta agggctttga gagttttggt   1020
tagagggaga atttgtgaac ctctcatgta ttccgagtga attggttgag gttgtttccc   1080
tctgtatttt gtactctcat gtttatagtg gattgctcat ttcctttgtg gacgtaggtc   1140
gattgaccga accacgttaa atctttgtgt cttttggtat atttctcgtt gtcttcttac    1200
tcgtggtctt tcgaggtttg ctttgctagc ttccgcgttt acacctgctt atttgcggtc    1260
ctaacagagt tcgatgggtt gaatctataa aaagaaaaat atactcgtga ttcacgatta    1320
tttatatgaa aatataataa atattgaatt tcctttgcta tttcttatgt ttacgtcttt    1380
atatttcaaa ttattccacc aatactgaca agccctaggc catctctagg aaattcatac    1440
aatttttttt ttgttgttaa ctagttaaat tggcagcctt aaagattatt gtaaaattca    1500
aggcaacttc ctcaagtact acaactcact tgtaacatcc cagtcaaagt gtcctaaaat   1560
tttataaaat ttgacacatg aaacaatagc acaataaatt ttagtactat tgcagccatg   1620
gcccataagc catcatgtat tatagtcaaa atgggtcctt ttccaatttg tcttgatccc    1680
aaaatccctt tgtaggtaag atggttcaac aaggaactat gactcttaag gtagacttgg    1740
actcatagac ttgtcataac tcataaagac ttggaatata ataattattc atttaaatta   1800
taattctcta ctttaatatc ttctactata aatacccttt caaagcctca ttatttgtac    1860
atcaaacatt gatattcatc tcttcaatct tttgtattca catattctat ttattcaata   1920
cacttaggaa aacactttac caagaaatta agatggagaa cttcccaatt attaacttgg    1980
aaaagctcaa tggagatgag agagccaaca ccatggaaat gatcaaagat gcttgtgaga   2040
attggggctt ctttgaggta atcataaatt acataaacat attaatatgt tgtttcaat    2100 ttatcagtca tactttctc tgttttaaaa ttaatgtcac tttcaatatt taataattcg    2160
catgacatgt ttataacaca acaagatata ggttacattt tgatacatta tatataactt   2220
ctgtcacacg actcaaaagt cttcttaat ttcttgaatt caatgatcga tcaaactaag    2280
acacgtaaaa tgaaacgggg aatagtaatt ctgtttgctt atgtgatcat tgtagttggt   2340
```

```
gaaccatgga attccacatg aagtaatgga cacagtagag aaaatgacaa agggacatta    2400
caagaagtgc atggaacaga ggtttaagga actagtggca agtaagggac ttgaggctgt    2460
tcaagctgag gttactgatt tagattggga aagcactttc ttcttgcgcc atcttcctac    2520
ttctaatatc tctcaagtac ccgatcttga cgaagaatac aggtacatac atgtgtccta    2580
catattgcgt atataataaa taaacacaaa atttaagtta tatacgctga cagtataact    2640
aattataatg ttgtaccaaa tgatgcagag aggtgatgag agattttgct aaaagattgg    2700
agaaattggc tgaggagtta cttgacttac tctgtgaaaa tcttggactt gaaaaaggtt    2760
acttgaaaaa tgccttttat ggatcaaaag gtcccaactt tggtactaaa gttagcaact    2820
atccaccatg tcctaagccc gatttgatca agggactccg cgctcataca gacgcaggag    2880
gcatcatact tctgttccaa gatgacaaag tgagtggcct tcaactcctc aaagacgagc    2940
aatggatcga tgttcctccc atgcgccact ctattgtggt taaccttggt gaccaacttg    3000
aggtacaaga ttcactaagt gtgtgtgttt ttatcactat aacttagaag tagtaactaa    3060
aaatggtatt aatgaaatgt tataaaaaca ggtgatcact aacgggaagt acaagagtgt    3120
gctgcacaga gtaattgcac aaacagacgg gacacgaatg tcattagcct cattttacaa    3180
tccaggaagt gatgcagtaa tatatccagc aaaaactttg gttgaaaaag aggcagagga    3240
aagtacacaa gtgtatccaa agtttgtgtt tgatgattac atgaagttat atgctggact    3300
caagtttcaa gccaaagagc aagatttgga agcaatgaag gcaatggaaa gtgatccaat    3360
tgcaagtgct tagatcccaa ttcaattaaa aaaattggtg tttgaaaaat atatttaaat    3420
atagcaatct atgtatacac attatttgct cttcttatgt atggtagaat aaagttagta    3480
ttaaaaaaga ttgtgatttg ctgcatatgt atcaaaaaga gtcctaatat ttgtatctat    3540
aaataaggtg ccttctagtg aaattataca aataataatt tggagtgtat tgttctttct    3600
catgtaattt aacttttaag tatcttactt tacaatatac tgttcactta ttgaacatat    3660
tgagtgatat attgactcaa t                                              3681
```

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 10 aatttcaaa                                                            9

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 11
tcatcttctt                                                           10

<210> SEQ ID NO 12
<211> LENGTH: 921
<212> TYPE: DNA
<213> ORGANISM: Lycopersicon esculentum

<400> SEQUENCE: 12

-continued

```
gtgaacctct catgtattcc gagtgaattg gttgaggttg tttccctctg tattttgtac    60
tctcatgttt atagtggatt gctcatttcc tttgtggacg taggtcgatt gaccgaacca   120
cgttaaatct ttgtgtcttt tggtatattt ctcgttgtct tcttactcgt ggtctttcga   180
ggtttgcttt gctagcttcc gcgtttacac ctgcttattt gcggtcctaa cagagttcga   240
tgggttgaat ctataaaaag aaaaatatac tcgtgattca cgattattta tatgaaaata   300
taataaatat tgaatttcct ttgctatttc ttatgtttac gtctttatat ttcaaattat   360
tccaccaata ctgacaagcc ctaggccatc tctaggaaat tcatacaatt ttttttttgt   420
tgttaactag ttaaattggc agccttaaag attattgtaa aattcaaggc aacttcctca   480
agtactacaa ctacattgta acatcccagt caaagtgtcc taaaatttta taaaatttga   540
cacatgaaac aatagcacaa taaattttag tactattgca gccatggccc ataagccatc   600
atgtattata gtcaaaatgg gtccttttcc aatttgtctt gatcccaaaa tcccttgta    660 ggtaagatgg ttcaacaagg aactatgact cttaaggtag acttggactc atagacttgt   720
cataactcat aaagacttgg aatataataa ttattcattt aaattataat tctctacttt   780
aatatcttct actataaata ccctttcaaa gcctcattat ttgtacatca acattgata    840 ttcatctctt caatcttttg tattcacata ttctatttat tcaatacact taggaaaaca   900
ctttaccaag aaattaagat g                                             921
```

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 13 tgtctc                                                                6

<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 14 gagaca                                                                6

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 15 tgtctt                                                                6

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic -continued
<210> SEQ ID NO 17
<211> LENGTH: 4
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 17 acgt                                                                      4

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 18
tcatttcctt                                                               10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide motif

<400> SEQUENCE: 19
ttgtcttctt                                                               10
```
(Note: SEQ 16 shown above as ctcgtg length 6)
```

What is claimed is:

1. An isolated polynucleotide, or a complement thereof, comprising a nucleic acid molecule that encodes an isopentenyl transferase (IPT) operably linked to a heterologous aminocyclopropane carboxylic acid oxidase (ACO) gene promoter, wherein said nucleic acid molecule that encodes said IPT is at least 80% identical to SEQ ID NO:5 and said heterologous ACO gene promoter comprises the nucleic acid sequence set forth in SEQ ID NO:6 or 7.

2. The isolated polynucleotide of claim 1, where said nucleic acid molecule that encodes said IPT is set forth as SEQ ID NO: 5.

3. The isolated polynucleotide of claim 1, wherein the nucleic acid molecule hybridizes under stringent conditions to the complement of a polynucleotide set forth as SEQ ID NO:8, wherein the stringent conditions are hybridizing in 0.5 M NaHPO$_4$, 7% sodium dodecylsulfate (SDS), 1 nM EDTA at 65° C. and washing in 0.1×SSC/0.1% SDS at 68° C.

4. A vector comprising the polynucleotide of claim 1.

5. The vector of claim 4, wherein the vector is an expression vector.

6. A host plant cell comprising the expression vector of claim 5.

7. The host plant cell of claim 6, wherein the plant cell is a cell from a plant selected from the group consisting of tobacco, chrysanthemum, petunia, tomato, melon, pea, poinsettia, rose, canola, flowering tobacco, watermelon and bent-grass.

8. A transgenic plant comprising a transgene which contains a nucleic acid sequence set forth as SEQ ID NO: 5 fused with a nucleic acid having the sequence of SEQ ID NO:6 or SEQ ID NO:7.

9. A transgenic chrysanthemum plant comprising the vector of claim 4.

10. A transgenic plant comprising the vector of claim 4, wherein the plant is selected from the group consisting of tobacco, petunia, tomato, melon, pea, poinsettia, rose, canola, flowering tobacco, watermelon and bent-grass.

11. A progeny of the transgenic plant of claim 10, wherein the progeny comprises said vector.

12. A seed of the transgenic plant of claim 10, wherein the seed comprises said vector.

13. A method for increasing number of lateral branches and flower buds in a plant, comprising transforming a plant with a transgene comprising a nucleic acid encoding isopentenyltransferase (IPT) operably linked to a heterologous aminocyclopropane carboxylic acid oxidase (ACO) gene promoter, wherein expression of said transgene in the transformed plant provides increased cytokinin levels in the transformed plant compared with a non-transformed plant of the same species.

14. The method of claim 13, wherein the plant is selected from the group consisting of tobacco, chrysanthemum, petunia, tomato, melon, pea, poinsettia, rose, canola, flowering tobacco, watermelon and bent-grass.

15. The method of claim 13, wherein the heterologous ACO gene promoter is a promoter from a tomato ACO gene.

16. The method of claim 13, wherein the ACO gene promoter comprises the sequence of SEQ ID NO:7.

17. The method of claim 13, wherein the ACO gene promoter comprises the sequence of SEQ ID NO:6.

18. The method of claim 13, wherein indoleacetic acid (IAA) production is increased in the plant.

19. The method of claim 13, wherein ethylene production is increased in the plant.

20. A kit comprising a $LEACO1_{0.918\ kb}$-ipt gene chimera comprised within a vector and instructions for use.

21. The kit of claim 20 for use in plant transformation.

* * * * *

UNITED STATES PATENT AND TRADEMARK OFFICE
CERTIFICATE OF CORRECTION

PATENT NO. : 7,741,548 B2
APPLICATION NO. : 11/432314
DATED : June 22, 2010
INVENTOR(S) : Richard McAvoy et al.

It is certified that error appears in the above-identified patent and that said Letters Patent is hereby corrected as shown below:

In the claims, in column 45, Claim 2, line 51, please delete "where" and insert --wherein--.

Signed and Sealed this

Thirtieth Day of November, 2010

David J. Kappos
*Director of the United States Patent and Trademark Office*